(12) United States Patent
Van Delft et al.

(10) Patent No.: US 9,987,373 B2
(45) Date of Patent: Jun. 5, 2018

(54) MODIFIED GLYCOPROTEIN, PROTEIN-CONJUGATE AND PROCESS FOR THE PREPARATION THEREOF

(71) Applicant: SynAffix B.V., Oss (NL)

(72) Inventors: Floris Louis Van Delft, Nijmegen (NL); Remon Van Geel, Lith-Oijen (NL); Maria Antonia Wijdeven, Lent (NL)

(73) Assignee: Synaffix B.V., Oss (NL)

( * ) Notice: Subject to any disclaimer, the term of this patent is extended or adjusted under 35 U.S.C. 154(b) by 0 days. days.

(21) Appl. No.: 15/028,874

(22) PCT Filed: Oct. 14, 2014

(86) PCT No.: PCT/NL2014/050715
§ 371 (c)(1),
(2) Date: Apr. 12, 2016

(87) PCT Pub. No.: WO2015/057064
PCT Pub. Date: Apr. 23, 2015

(65) Prior Publication Data
US 2016/0250347 A1 Sep. 1, 2016

(30) Foreign Application Priority Data

Oct. 14, 2013 (EP) ..................................... 13188537
Oct. 14, 2013 (EP) ..................................... 13188585
Apr. 23, 2014 (EP) ..................................... 14165548
Apr. 23, 2014 (EP) ..................................... 14165581

(51) Int. Cl.
| | | |
|---|---|---|
| *C12P 21/00* | (2006.01) |
| *A61K 47/48* | (2006.01) |
| *C07K 16/32* | (2006.01) |
| *C12P 19/18* | (2006.01) |
| *C12N 9/24* | (2006.01) |
| *A61K 31/702* | (2006.01) |
| *A61K 39/00* | (2006.01) |

(52) U.S. Cl.
CPC .. *A61K 47/48384* (2013.01); *A61K 47/48584* (2013.01); *C07K 16/32* (2013.01); *C12P 21/00* (2013.01); *C12P 21/005* (2013.01); *A61K 2039/505* (2013.01); *C07K 2317/41* (2013.01)

(58) Field of Classification Search
CPC ...... C12P 21/005; C12P 21/00; C12N 9/1051; A61K 2039/505; C12Y 204/01
USPC ..... 435/328, 200, 201, 72, 74; 530/395, 397
See application file for complete search history.

(56) References Cited

U.S. PATENT DOCUMENTS

| | | |
|---|---|---|
| 6,254,868 B1 | 7/2001 | Leung et al. |
| 2006/0034828 A1 | 2/2006 | Gerngross et al. |
| 2009/0068738 A1 | 3/2009 | Bertozzi et al. |
| 2011/0207147 A1 | 8/2011 | Jewett et al. |

FOREIGN PATENT DOCUMENTS

| | | |
|---|---|---|
| WO | WO-03/031464 A1 | 4/2003 |
| WO | WO-2004/063344 A2 | 7/2004 |
| WO | WO-2007/095506 A1 | 8/2007 |
| WO | WO-2007/133855 A2 | 11/2007 |
| WO | WO-2008/029281 A2 | 3/2008 |
| WO | WO-2009/025646 A1 | 2/2009 |
| WO | WO-2009/067663 A1 | 5/2009 |
| WO | WO-2009/102820 A2 | 8/2009 |
| WO | WO-2011/061629 A2 | 5/2011 |
| WO | WO-2011/136645 A1 | 11/2011 |
| WO | WO-2013/037824 A1 | 3/2013 |
| WO | WO-2014/065661 A1 | 5/2014 |

OTHER PUBLICATIONS

Bertozzi et al., "Rapid cu-free click chemistry with readily synthesized biarylazacyclooctynones" Journal of American Chemistry, 2010, vol. 132, pp. 3688-3690.
Bojarova et al., "Synthesis of LacdiNAc-terminated glycoconjugates by mutant galactosyltransferase—A way to new glycodrugs and materials", Glycobiology, 2009, vol. 19, No. 5, pp. 509-517.
Chuh et al., "Changes in metabolic chemical reporter structure yield a selective probe of O-GlcNAc modification", Journal of the American Chemical Society, 2014, vol. 136, pp. 12283-12295.

(Continued)

*Primary Examiner* — Robert B Mondesi
*Assistant Examiner* — Mohammad Y Meah
(74) *Attorney, Agent, or Firm* — Gilberto M. Villacorta; Sunit Talapatra; Foley & Lardner LLP

(57) ABSTRACT

Glycoproteins comprising a glycan of the formula (102) are disclosed; wherein b is 0 or 1; the GlcNAc residue optionally fucosylated; and $Su(A)_x$ is a sugar derivative comprising x functional groups A, wherein x is 1, 2, 3 or 4 and A is independently selected from the group consisting of an azido group, a keto group, an alkynyl group, a thiol group, a halogen, a sulfonyloxy group, a halogenated acetamido group, a mercaptoacetamido group and a sulfonylated hydroxyacetamido group.

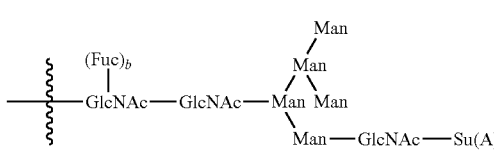

Protein-conjugates having glycoproteins according to the invention conjugated to a molecule of interest (e.g., an active substance) are also disclosed. Examples include modified antibodies, antibody-conjugates, and antibody-drug conjugates (ADCs). Processes for the preparation of the modified glycoproteins according to the invention and methods for the preparation of a protein-conjugate according to the invention are mentioned.

19 Claims, 18 Drawing Sheets

(56) References Cited

OTHER PUBLICATIONS

Davis et al., "An endoglycosidase with alternative glycan specificity allows broadened glycoprotein remodelling" Journal of the American Chemical Society, 2012, vol. 134, pp. 8030-8033.

De Pourcq et al., "Engineering of glycosylation in yeast and other fungi: current state and perspectives", Appl Microbiol Biotechnol, 2010, vol. 87, pp. 1617-1631.

Debets et al., "Aza-dibenzocyclooctynes for fast and efficient enzyme PEGylation via copper-free (3 2) cycloaddition", Chemistry Communication, 2010, vol. 46, pp. 97-99.

Debets et al., "Bioconjugation with strained alkenes and alkynes", Accounts of Chemical Research, 2011, vol. 44, No. 9, pp. 805-815.

Elling et al., "Chemoenzymatic synthesis of biotinylated nucleotide sugars as substrates for glycosyltransferases", Chembiochem, 2001, vol. 2, pp. 884-894.

International Search Report issued in International Patent Application No. PCT/NL2014/050715 dated Mar. 13, 2015.

Jawalekar et al., "Oligonucleotide tagging for copper-free click conjugation", Molecules, 2013, vol. 18, pp. 7346-7363.

Khidekel et al., "A chemoenzymatic approach toward the rapid and sensitive detection of O-GlcNAc posttranslational modifications", Journal of American Chemical Society, 2003, vol. 125, pp. 16162-16163.

Mercer et al., "Use of novel mutant Galactosyltransferase for the bioconjugation of terminal N-Acetylglucosamine (GlcNAc) residues on live cell surface", Bioconjugate Chemistry, 2013, vol. 24, pp. 144-152.

Oh-Eda et al., "Overexpression of the Golgi-localized enzyme alpha-mannosidase IIx in Chinese hamster ovary cells results in the conversion of hexamannosyl-N-acetylchitobiose to tetramannosyl-N-acetylchitobiose in the N-glycan-processing pathway", European Journal of Biochemistry, 2001, vol. 268, pp. 1280-1288.

Okeley et al., "Metabolic engineering of monoclonal antibody carbohydrates for antibody-drug conjugation", Bioconjugate Chemistry, 2013, vol. 24, pp. 1650-1655.

Pannecoucke et al., "6-Azido D-galactose transfer to N-acetyl-D-glucosamine derivative using commercially available beta-1, 4-galactosyltransferase", Tetrahedron Letters, 2009, vol. 49, pp. 2294-2297.

Piller et al., "Two-step enzymatic synthesis of UDP-N-acetylgalactosamine", Biorganic & Medicinal Chemistry Letters, 2005, vol. 15, pp. 5459-5462.

Pouilly et al., "Evaluation of analogues of GalNAc as substrates for enzymes of the mammalian GalNAc salvage pathway", ACS Chemical Biology, 2012, vol. 7, pp. 753-760.

Qasba et al., "Site specific conjugation of fluoroprobes to the remodeled Fc N-Glycans of monoclonal antibodies using mutant glycosyltransferases: Application for cell surface antigen detection", Bioconjugate Chemistry, 2009, vol. 20, pp. 1228-1236.

Qasba et al., "Structure-based design of beta-1, 4-galactosyltransferase I (beta-4Gal-T1) with equally efficient N-acetylgalactosaminylstransferase activity", The Journal of Biological Chemistry, Jun. 2002, vol. 277, No. 23, pp. 20833-20839.

Qasba et al., "Studies on the metal binding sites in the catalytic domain of beta-1, 4-galactosyltransferase", Glycobiology, 2002, vol. 12, No. 7, pp. 395-407.

Qasba et al., "The N-terminal stem region of bovine and human beta-1, 4-galactosyltransferase I increase the in vitro folding efficiency of their catalytic domain from inclusion bodies", Protein Expression and Purification, 2003, vol. 30, pp. 219-229.

Satoh et al., "Comparison of biological activity among nonfucosylated therapeutic IgG1 antibodies with three different N-linked Fc oligosaccharides: the high-mannose, hybrid, and complex types", Glycobiology, 2006, vol. 17, No. 1, pp. 104-118.

Shabat et al., "Self-immolative dendrimers: a distinctive approach to molecular amplification", Soft Matters, 2010, vol. 6, pp. 1073-1080.

Temming et al., Protein enrichment by capture-release based on strain-promoted cycloaddition of azide with bicyclononyne (BCN), Bioorganic & Medicinal Chemistry, 2012, vol. 20, pp. 655-661.

Tolbert et al., "Enzyme-catalyzed synthesis of a hybrid N-linked oligosaccharide using N-acetylglucosaminyltransferase I", Adv. Synth. Catal., 2008, vol. 350, pp. 1689-1695.

Van Berkel et al., "Metal-free bioconjugation reactions" Drug Discovery Today: Technologies, 2013, vol. 10, No. 1, pp. e45-e51.

Wang et al., "Chemoenzymatic glycoengineering of intact IgG antibodies for gain of functions", Journal of the American Chemical Society, 2012, vol. 134, pp. 12308-12318.

Wang et al., "Highly efficient synthesis of UDP-GalNAc/GlcNAc analogues with promiscuous recombinant human UDP-GalNAc pyrophosphorylase AGX1", Chemistry A European Journal, 2010, vol. 16, pp. 13343-13345.

Zeglis et al., "Enzyme-mediated methodology for the site-specific radiolabeling of antibodies based on catalyst-free click chemistry", Bioconjugate Chemistry, 2013, vol. 24, pp. 1057-1067.

Abbas et al., "Allenamides as orthogonal handles for selective modification of cysteine in peptides and proteins", Angew. Chem. Int. Ed., 2014, vol. 53, pp. 7491-7494.

Agnew et al., "Evaluating options for hard to label antibodies", Life Technologies/ ABRF ARG User's Study: 2012-2013, Apr. 2013, pp. 1-12, retrieved from the Internet: URL: http://www.abrf.org.Other/ABRFMeetings/ABRF2013/RG%20presentations/RG3_ARG_Agnew.pdf.

Alley et al., "Antibody-drug conjugates: targeted drug delivery for cancer", Current Opinion in Chemical Biology, 2010, vol. 14, pp. 529-537.

Ayoub et al., "Correct primary structure assessment and extensive glycol-profiling of cetuximab by a combination of intact, middle-up, middle-down and bottom-up ESI and MALDI mass spectrometry techniques", MABS, 2013, vol. 5, No. 5, pp. 699-710.

Baisch et al., "Convenient chemoenzymatic synthesis of beta-purine-diphosphate sugars (GDP-fucose-analogues)", Bioorganic & Medicinal Chemistry, 1997, vol. 5, No. 2, pp. 383-391.

Bourgeau, "Develpement d'un systeme de regeneration d'UDP-GA1NAc pour la glycosylation enzymatique d'oligosaccharides et de peptides d'interet therapeautique", HAL-archives ouvertes, 2007, pp. 32-58.

Brik et al., "Sugar-assisted ligation for the synthesis of glycopeptides", Chemistry—A European Journal, 2007, vol. 13, pp. 5670-5675.

Bross et al., "Approval summary: Gemtuzumab ozogamicin in relapsed acute myeloid leukemia", Clinical Cancer Research, Jun. 2001, vol. 7, pp. 1490-1496.

Clark et al., "Direct in-gel fluorescence detection and cellular imaging of O-GlcNAc-modified proteins", Journal of the American Chemical Society, 2008, vol. 130, pp. 11576-11577.

Finn et al., "Analysis and optimization of copper-catalyzed azide-slkyne cycloaddition for bioconjugation", Angew. Chem. Int. Ed., 2009, vol. 48, pp. 9879-9883.

Huang et al., "Chemoenzymatic Glycoengineering of intact IgG antibodies for gain of functions", Journal of the American Chemical Society, 2012, vol. 134, pp. 12308-12318.

International Search Report issued in International Patent Application No. PCT/NL2014/050714, dated Feb. 17, 2015.

International Search Report issued in International Patent Application No. PCT/NL2014/050716, dated Jan. 22, 2015.

International Search Report issued in International Patent Application No. PCT/NL2014/050717, dated Feb. 13, 2015.

Kim et al., "Chemical arsenal for the study of O-GlcNAc", Molecules, 2011, vol. 16, pp. 1987-2022.

Kunz et al., "Synthetic vaccines of tumor-associated glycopeptide antigens by immune-compatible thioether linkage to bovine serum albumin", Angew. Chem. Int. Ed., 2007, vol. 46, pp. 5226-5230.

Labrijn et al., "Therapeutic IgG4 antibodies engage in Fab-arm exchange with endogenous human IgG4 in vivo", Nature Biotechnology, Aug. 2009, vol. 27, No. 8, pp. 767-773.

N.N.: "A new site specific antibody conjugation using bacterial transglutaminase", Innate Pharma ADC Summit, San Francisco, Oct. 15, 2013, pp. 1-29.

Olsen et al., "EndoS, a novel secreted protein from *Streptococcus pyogenes* with endoglycosidase activity on human IgG", The EMBO Journal, 2001, vol. 20, No. 12, pp. 3046-3055.

(56) References Cited

OTHER PUBLICATIONS

Qasba et al., "Site-specific linking of biomolecules via glycan residues using glycosyltransferases", Biotechnology Progress, 2008, vol. 24, pp. 520-526.
Qu et al., "Carbohydrates engineered at antibody constant domains can be used for site-specific conjugation of drugs and chelates", Journal of Immunological Methods, 1998, vol. 213, pp. 131-144.
Rochefort et al., "Metabolic exploitation of the sialic acid biosynthetic pathway to generate site-specific labeled antibodies", Glycobiology, Oct. 2013, vol. 24, No. 1, pp. 62-69.
Sharma et al., "Design and synthesis of LNA based mercaptoacetamido-linked nucleoside dimmers", Carbohydrate News Letters (India), Dec. 2013, vol. 14, p. 15, poster abstract.
Wang et al., "Enrichment and site mapping of O-linked N-acetylglucosamine by a combination of chemical/enzymatic tagging, photochemical cleavage, and electron transfer dissociation mass spectrometry", Molecular & Cellular Proteomics, 2010, vol. 9, pp. 153-160.
Wong et al., "Enzymes in the synthesis of glycoconjugates", Chemical Reviews, 2011, vol. 111, pp. 4529-4307.
Wright et al., "Antibody variable region glycosylation: position effects on antigen binding and carbohydrate structure", The EMBO Journal, 1991, vol. 10, No. 10, pp. 2717-2723.

Fig. 4
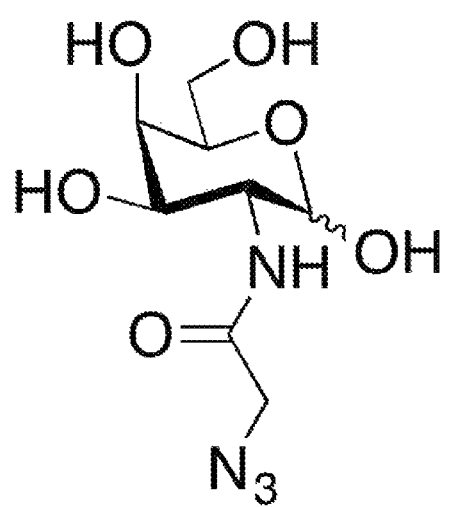
7
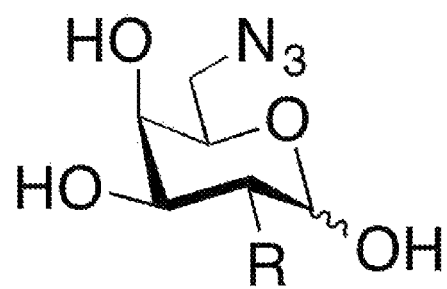
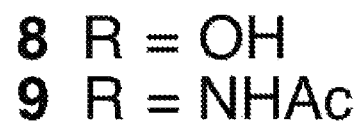
8 R = OH
9 R = NHAc

Fig. 7
(A)
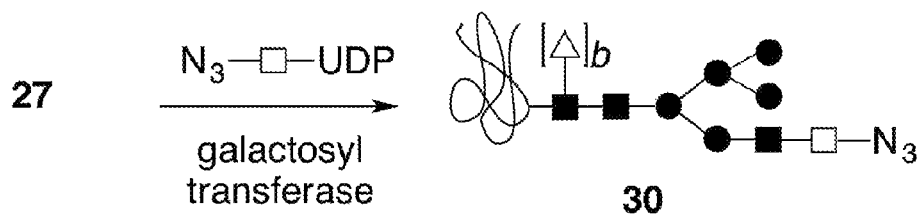
(B)
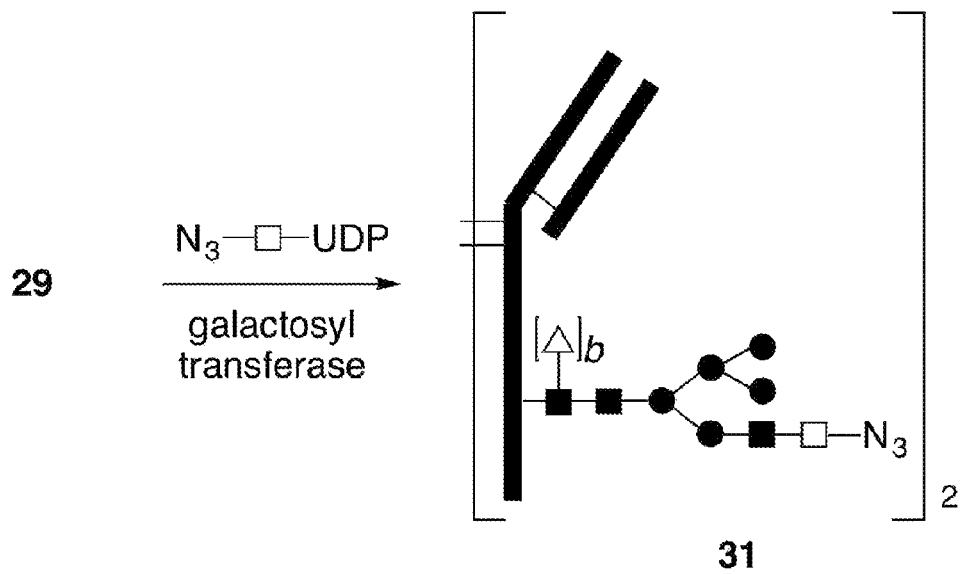

Fig. 10

35  vc-PABA-β-ala-maytansin  37

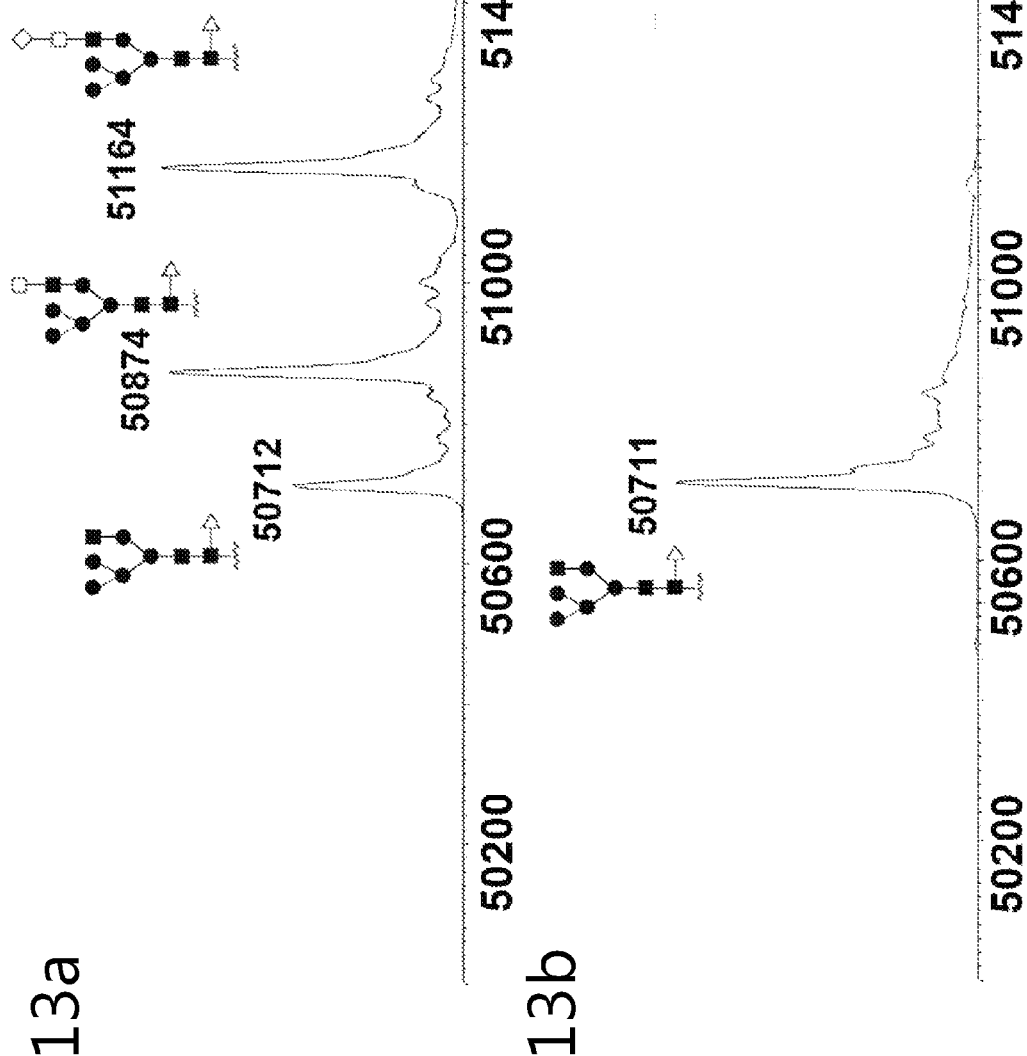

MODIFIED GLYCOPROTEIN, PROTEIN-CONJUGATE AND PROCESS FOR THE PREPARATION THEREOF

CROSS-REFERENCE TO RELATED APPLICATIONS

This application is the National Phase of International Patent Application No. PCT/NL2014/050715, filed Oct. 14, 2014, published on Apr. 23, 2015 as WO 2015/057064 A1, which claims priority to European Patent Application No. 13188537.8, filed Oct. 14, 2013, European Patent Application No. 13188585.7, filed Oct. 14, 2013, European Patent Application No. 14165548.0, filed Apr. 23, 2014, and European Patent Application No. 14165581.1, filed Apr. 23, 2014. The contents of these applications are herein incorporated by reference in their entirety.

SEQUENCE LISTING

The instant application contains a Sequence Listing which has been submitted in ASCII format via EFS-WEB and is hereby incorporated by reference in its entirety. Said ASCII copy, created on Apr. 11, 2016, is named 069818-3560SequenceListing.txt and is 32 KB.

TECHNICAL FIELD OF THE INVENTION

The present invention relates to modified glycoproteins, in particular to modified glycoproteins comprising a glycan with a modified sugar moiety. The invention also relates to a glycoprotein-conjugate wherein a glycoprotein according to the invention is conjugated to a molecule of interest. Said molecule of interest may for example be a an active substance. The invention further relates to a process for the preparation of a modified glycoprotein, and to a method for the preparation of a glycoprotein-conjugate. The invention particularly relates to modified antibodies, antibody-conjugates, antibody-drug conjugates and methods for the preparation thereof.

BACKGROUND OF THE INVENTION

Protein conjugates, i.e. proteins conjugated to a molecule of interest via a linker, are known in the art. For example, fluorescent labeling is a powerful technique for in vitro and in vivo visualisation, covalent immobilization of proteins is a useful strategy for industrial application and PEGylation of proteins leads to significantly enhanced circulation time. In addition, there is great interest in antibody-conjugates wherein the molecule of interest is a drug, for example a cytotoxic chemical. Antibody-drug-conjugates are known in the art, and consist of a recombinant antibody covalently bound to a cytotoxic chemical via a synthetic linker.

Protein conjugates known from the prior art are commonly prepared by conjugation of a functional group to the side chain of amino acid lysine or cysteine, by acylation or alkylation, respectively.

For lysines, conjugation takes place preferentially at lysine side chains with highest steric accessibility, the lowest pKa, or a combination thereof. Disadvantage of this method is that site-control of conjugation is low.

Better control of site-specificity is obtained by alkylation of cysteines, based on the fact that typically no or few free cysteines are present in a typical protein, thereby offering the option of alkylating only those cysteines that are already present in reduced form or selectively engineered into a protein. Alternatively, cysteines can be selectively liberated by a (partial) reductive step. For example, selective cysteine liberation by reduction is typically performed by treatment of a protein with a reducing agent (e.g. tris(2-carboxyethyl) phosphine (TCEP) or dithiothreitol (DTT)), leading to conversion of a disulfide bond into two free thiols. The liberated thiols are then alkylated with an electrophilic reagent, typically based on a maleimide chemistry, which generally proceeds fast and with high selectivity, or with haloacetamides, which also show strong preference for cysteine but side-reactions with lysine side-chains may be encountered.

One recent report (N. M. Okeley et al., *Bioconj. Chem.* 2013, 24, 1650, incorporated by reference herein) describes the metabolic incorporation of 6-thiofucose into the glycan of a monoclonal antibody, followed by reduction-oxidation, then maleimide conjugation. Interestingly, it was found that the 6-thiofucose maleimide conjugate described above was found to display enhanced stability with respect to cysteine maleimide conjugates. However, efficiency of incorporation of 6-thiofucose was found to be only 70%.

An alternative variant of maleimide conjugation, which was applied for the generation of an antibody-drug conjugate, involves a strategy where not the nucleophilic thiol is introduced in the monoclonal antibody, but rather the maleimide. For example, T-DM1 is prepared by first (random) conjugation of lysines with succinimidyl 4-(N-maleimidomethyl)cyclohexane-1-carboxylate (SMCC), thereby effectively charging the antibody with maleimides. In the next stage of the process, the maleimide-functionalized antibody is treated with thiol-functionalized maytansinoid, leading to the conjugate. Hence, this is an example where the antibody is converted into an electrophilic reaction partner (instead of the common use of nucleophilic amino acid side chains for conjugation), upon treatment with SMCC. However, also in this case, by nature of the approach, only random conjugation of antibody is achieved.

Notwithstanding the versatility of the above technologies, a general disadvantage of protein conjugates obtained via alkylation with maleimides is that in general the resulting conjugates can be unstable due to the reverse of alkylation, i.e. a retro-Michael reaction.

An alternative strategy to prepare conjugates of a glycoprotein, a subclass of all proteins, involves the selective attachment of functional moieties to one (or more) of the glycans present on the glycoprotein.

One example of conjugation to glycoproteins involves the generation of one or more aldehyde functions on the protein's glycan structure, either by chemical means (sodium periodate) or by enzymatic means (galactose oxidase). The latter aldehyde function can subsequently be employed for a selective conjugation process, for example by condensation with a functionalized hydroxylamine or hydrazine molecule, thereby generating an oxime-linked or hydrazone-linked protein conjugate, respectively. However, it is known that oximes and hydrazones, in particular derived from aliphatic aldehydes, also show limited stability over time in water or at lower pH. For example, gemtuzumab ozogamicin is an oxime-linked antibody-drug conjugate and is known to suffer from premature deconjugation in vivo.

Another example of glycoprotein conjugation involves the use of a glycosyltransferase for controlled modification of the glycan with a monosaccharide of choice.

Qasba et al. disclose in WO 2004/063344 and in *J. Biol. Chem.* 2002, 277, 20833, both incorporated by reference herein, that mutant galactosyltransferases GalT(Y289L), GalT(Y289I) and GalT(Y289N) can enzymatically attach GalNAc to a non-reducing GlcNAc sugar ((β-benzyl-Glc-NAc).

WO 2007/095506 and WO 2008/029281 (Invitrogen Corporation), incorporated by reference herein, disclose that the combination of GalT(Y289L) mutant with C2-substituted azidoacetamido-galactose UDP-derivative (UDP-GalNAz) leads to the incorporation of GalNAz at a terminal non-reducing GlcNAc of a glycan. Subsequent conjugation by Staudinger ligation or with copper-catalyzed click chemistry then provides the respective antibody conjugates wherein a fluorescent alkyne probe is conjugated to an antibody. WO 2007/095506 and WO 2008/029281 further disclose that trimming of the glycan can take place with endo H, thereby hydrolyzing a GlcNAc-GlcNAc glycosidic bond and liberating a GlcNAc for enzymatic introduction of GalNAz.

A disadvantage of the latter approach is the removal of most of the hydrophilic sugars, which may not only hamper conjugation because of the single sugar remaining in the linker, but may also increase protein aggregation due to decreased hydrophilicity of the linker connecting the protein and the functional molecule, in particular when the functional molecule is hydrophobic. It is desirable in such case to prepare protein conjugates with linkers that are both longer (more sugars) and more hydrophilic (better water-solubility).

Qasba et al. disclose in *Bioconjugate Chem.* 2009, 20, 1228, incorporated by reference herein, that β-galactosidase-treated monoclonal antibodies (e.g. Rituxan, Remicade, Herceptin) having a G0 glycoform (obtained by treatment of the crude mAbs with galactosidase) are fully regalactosylated to the G2 glycoform after transfer of GalNAz to the terminal GlcNAc residues of the glycan, leading to tetraazido-substituted antibodies, i.e. two GalNAz moieties per heavy chain. The transfer of a galactose moiety comprising a C2-substituted keto group (C2-keto-Gal) to the terminal GlcNAc residues of a G0 glycoform glycan, as well as the linking of C2-keto-Gal to aminooxy biotin, is also disclosed.

Based on the above, it is clear that galactose can be introduced to proteins featuring a terminal GlcNAc-moiety upon treatment with wild type Gal-T1/UDP-Gal (leading to Gal-GlcNAc-protein), while N-acetylgalactosamine can be introduced upon treatment with GalT1 mutant Y289L (affording GalNAc-GlcNAc-protein). It has also been shown by Elling et al. (*Chem Bio Chem* 2001, 2, 884, incorporated by reference herein) that a variety of human galactosyltransferases (β4-Gal-T1, β4-Gal-T4 and β3-Gal-T5), but not bovine β4-Gal-T1, can accommodate a 6-biotinylated modification of galactose in UDP-Gal, in the absence of $Mn^{2+}$, leading to effective transfer to model proteins BSA-(GlcNAc)$_{17}$ and ovalbumin. Similarly, Pannecoucke et al. (*Tetrahedron Lett.* 2008, 49, 2294, incorporated by reference herein) demonstrated that commercially available bovine β4-Gal-T1 under standard conditions is also able to transfer UDP-6-azidogalactose to a model GlcNAc-substrate, but the transfer to a GlcNAc-protein was not demonstrated.

In WO 2007/133855 (University of Maryland Biotechnology Institute), incorporated by reference herein, a chemoenzymatic method for the preparation of a homogeneous glycoprotein or glycopeptide is disclosed, involving a two-stage strategy entailing first trimming of the near-complete glycan tree (under the action of endo A, endo H or endo S) leaving only the core N-acetylglucosamine (GlcNAc) moiety (the so-called GlcNAc-protein), followed by a reglycosylation event wherein, in the presence of a catalyst comprising a mutant endoglycosidase (ENGase), an oligosaccharide moiety is transferred to the GlcNAc-protein to yield a homogeneous glycoprotein or glycopeptide. A strategy for azide-functionalized glycoproteins is disclosed, wherein a GlcNAc-protein is reacted in the presence of ENGase with a tetrasaccharide oxazoline containing two 6-azidomannose moieties, thereby introducing two azides simultaneously in the glycan. The azide-functionalized glycoprotein may then be catalytically reacted in a "click chemistry" cycloaddition reaction, in the presence of a catalyst (e.g. a Cu(I) catalyst) with a terminal alkyne bearing a functional moiety X of interest. No actual examples of said click chemistry are disclosed.

In *J. Am. Chem. Soc.* 2012, 134, 8030, incorporated by reference herein, Davis et al. disclose the transfer of oligosaccharide oxazolines on a core-fucosylated as well as nonfucosylated core-GlcNAc-Fc domain of intact antibodies, in the presence of glycosynthase EndoS.

In *J. Am. Chem. Soc.* 2012, 134, 12308, incorporated by reference herein, Wang et al. disclose the transfer of a tetrasaccharide oxazoline containing two 6-azidomannose moieties on core-fucosylated as well as nonfucosylated core-GlcNAc-Fc domain of intact antibodies (Rituximab) in the presence of glycosynthase mutants EndoS-D233A and EndoS-D233Q.

However, a disadvantage of the glycosynthase strategies disclosed in WO 2007/133855, *J. Am. Chem. Soc.* 2012, 134, 8030 and *J. Am. Chem. Soc.* 2012, 134, 12308 is the lengthy and complex synthesis of the required azido-containing oligosaccharide oxazolines. In addition, the azido-containing oligosaccharide oxazolines comprise two azido groups. To date, it has not been shown whether this process may be suitable for the introduction of only one azido group on an antibody glycan.

SUMMARY OF THE INVENTION

The present invention relates to a process for the preparation of a modified glycoprotein, the process comprising contacting a glycoprotein comprising a glycan of the formula GlcNAcMan$_5$GlcNAc$_2$ with Su(A)$_x$-P in the presence of a suitable catalyst; wherein the core GlcNAc residue of said glycan is optionally fucosylated; wherein a suitable catalyst is defined as a galactosyltransferase or a galactosyltransferase comprising a mutant catalytic domain, wherefore Su(A)$_x$-P is a substrate; wherein Su(A)$_x$ is a sugar derivative comprising x functional groups A wherein x is 1, 2, 3 or 4 and A is independently selected from the group consisting of an azido group, a keto group, an alkynyl group, a thiol group or a precursor thereof, a halogen, a sulfonyloxy group, a halogenated acetamido group, a mercaptoacetamido group and a sulfonylated hydroxyacetamido group; wherein P is a nucleotide; wherein a modified glycoprotein is defined as a glycoprotein comprising a glycan of the formula Su(A)$_x$(GlcNAcMan$_5$GlcNAc$_2$ wherein the core GlcNAc residue is optionally fucosylated; and wherein GlcNAcMan$_5$GlcNAc$_2$ is a glycan according to formula (101) and Su(A)$_x$(GlcNAcMan$_5$GlcNAc$_2$ is a glycan according to formula (102), wherein b is 0 or 1 and Su(A)$_x$ is as defined above.

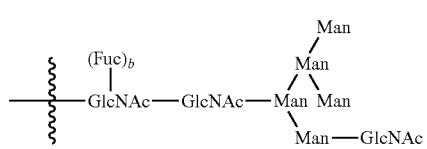

101

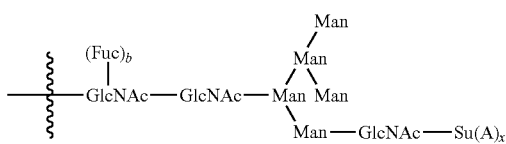

(102)

In particular, the invention relates to a process for the preparation of a modified glycoprotein, comprising contacting a glycoprotein comprising a GlcNAcMan$_5$GlcNAc$_2$ glycan with Su(A)$_x$-P in the presence of a catalyst selected from the group consisting of β(1,4)-galactosyltransferases, β(1,3)-N-galactosyltransferases, β(1,4)-galactosyltransferases comprising a mutant catalytic domain and β(1,3)-N-galactosyltransferases comprising a mutant catalytic domain; wherein the core GlcNAc residue of said glycan is optionally fucosylated; wherein Su(A)$_x$ is a monosaccharide sugar derivative comprising x functional groups A wherein x is 1, 2, 3 or 4 and A is independently selected from the group consisting of an azido group, a keto group, an alkynyl group, a thiol group or a precursor thereof, a halogen, a sulfonyloxy group, a halogenated acetamido group, a mercaptoacetamido group and a sulfonylated hydroxyacetamido group; wherein P is a nucleotide; wherein a modified glycoprotein is defined as a glycoprotein comprising a Su(A)$_x$GlcNAcMan$_5$GlcNAc$_2$ glycan wherein the core GlcNAc residue is optionally fucosylated; and wherein GlcNAcMan$_5$GlcNAc$_2$ is a glycan according to formula (101) and Su(A)$_x$GlcNAcMan$_5$GlcNAc$_2$ is a glycan according to formula (102), as defined above.

The invention also relates to a glycoprotein comprising a glycan of the formula Su(A)$_x$GlcNAcMan$_5$GlcNAc$_2$, wherein Su(A)$_x$GlcNAcMan$_5$GlcNAc$_2$ is as defined above; wherein Su(A)$_x$ is a sugar derivative comprising x functional groups A wherein x is 1, 2, 3 or 4 and A is independently selected from the group consisting of an azido group, a keto group, an alkynyl group, a thiol group, a halogen, a sulfonyloxy group, a halogenated acetamido group, a mercaptoacetamido group and a sulfonylated hydroxyacetamido group; and wherein the core GlcNAc residue of said glycan is optionally fucosylated.

The invention further relates to a process for the preparation of a protein-conjugate, said process comprising reacting a modified glycoprotein according to the invention with a linker-conjugate, wherein said linker-conjugate comprises a functional group B and one or more molecules of interest, wherein said functional group B is a functional group that is capable of reacting with a functional group A of a Su(A)$_x$GlcNAcMan$_5$GlcNAc$_2$ glycan on said glycoprotein, and wherein Su(A)$_x$ is as defined above.

The invention further relates to a protein-conjugate and to an antibody-conjugate obtainable by the process according to the invention.

BRIEF DESCRIPTION OF THE FIGURES

FIG. 4 shows the structures of azido-modified galactose derivatives (7-9) for transfer onto a GlcNAc-terminated sugar under the action of a galactosyl transferase (or a mutant thereof).

FIG. 7 shows the potential conversion of 27 and 29 into an azido-modified glycan upon the action of a galactosyltransferase in the presence of UDP-GalNAz.

FIG. 10 shows the reaction scheme for the synthesis of BCN-maytansinoid conjugate (37).

FIG. 13a shows the mass spectral profile of trastuzumab expressed in CHO in the presence of swainsonine (mixture of GnM$_5$, GalGnM$_5$ and SialGalGnM$_5$) and FIG. 13b shows the mass spectral profile of trastuzumab resulting from expression in CHO in the presence of swainsonine, after treatment with sialidase and galactosidase.

FIG. 16 shows the in vitro cytotoxicity of a range of ADCs against SK-OV-3 cell line.

DETAILED DESCRIPTION OF THE INVENTION

Definitions

Figure 1:
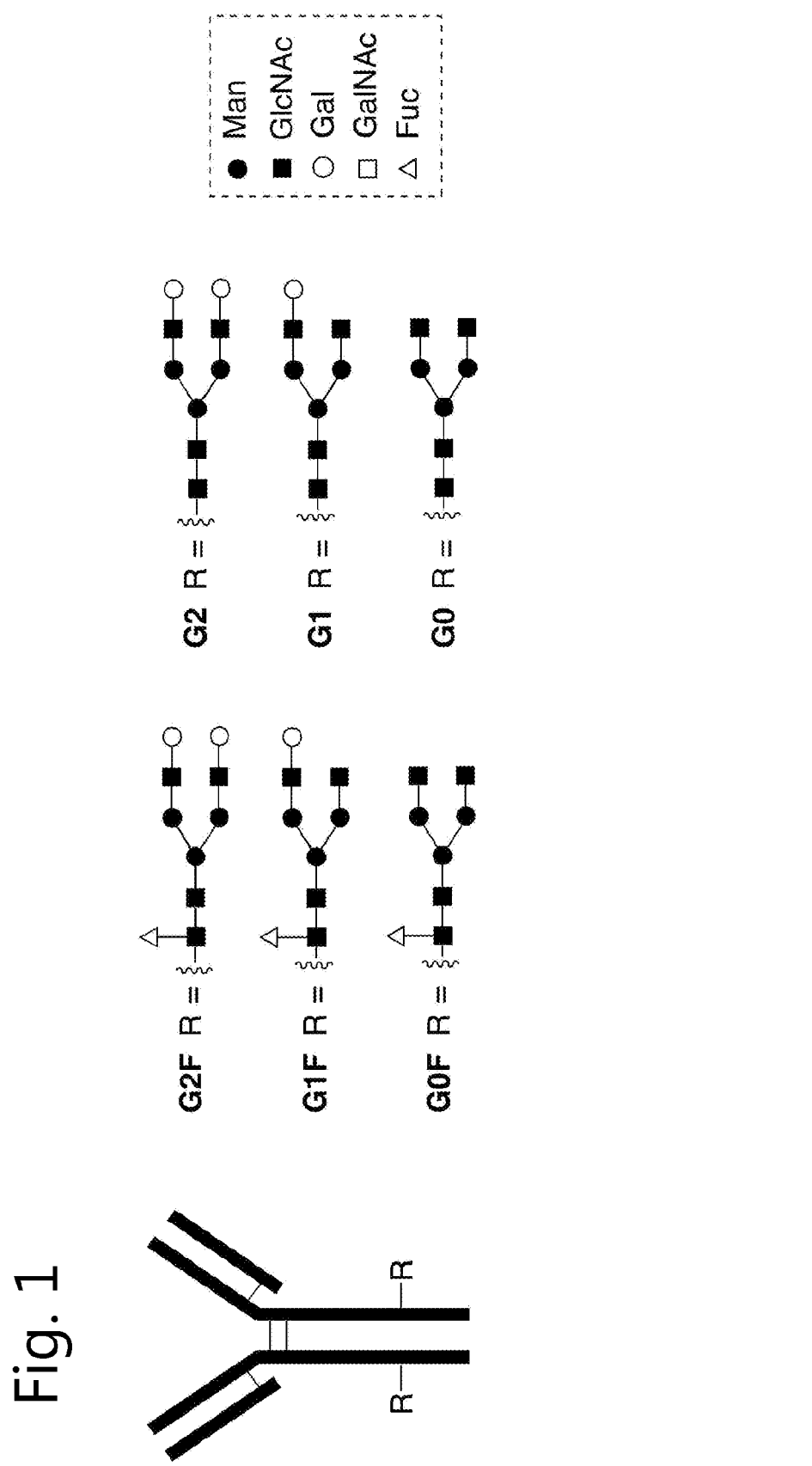
FIG. 1 shows examples of possible glycosylation profiles of monoclonal antibodies after typical expression in CHO. The glycoforms G0, G1, G2, G0F, G1F and G2F of a biantennary complex glycan are shown.

The verb "to comprise" as is used in this description and in the claims and its conjugations is used in its non-limiting sense to mean that items following the word are included, but items not specifically mentioned are not excluded.

In addition, reference to an element by the indefinite article "a" or "an" does not exclude the possibility that more than one of the element is present, unless the context clearly requires that there is one and only one of the elements. The indefinite article "a" or "an" thus usually means "at least one".

The compounds disclosed in this description and in the claims may comprise one or more asymmetric centres, and different diastereomers and/or enantiomers may exist of the compounds. The description of any compound in this description and in the claims is meant to include all diastereomers, and mixtures thereof, unless stated otherwise. In addition, the description of any compound in this description and in the claims is meant to include both the individual enantiomers, as well as any mixture, racemic or otherwise, of the enantiomers, unless stated otherwise. When the structure of a compound is depicted as a specific enantiomer, it is to be understood that the invention of the present application is not limited to that specific enantiomer.

The compounds may occur in different tautomeric forms. The compounds according to the invention are meant to include all tautomeric forms, unless stated otherwise. When the structure of a compound is depicted as a specific tautomer, it is to be understood that the invention of the present application is not limited to that specific tautomer.

The compounds disclosed in this description and in the claims may further exist as exo and endo diastereoisomers. Unless stated otherwise, the description of any compound in the description and in the claims is meant to include both the individual exo and the individual endo diastereoisomers of a compound, as well as mixtures thereof. When the structure of a compound is depicted as a specific endo or exo diastereomer, it is to be understood that the invention of the present application is not limited to that specific endo or exo diastereomer.

Furthermore, the compounds disclosed in this description and in the claims may exist as cis and trans isomers. Unless stated otherwise, the description of any compound in the description and in the claims is meant to include both the individual cis and the individual trans isomer of a compound, as well as mixtures thereof. As an example, when the structure of a compound is depicted as a cis isomer, it is to be understood that the corresponding trans isomer or mixtures of the cis and trans isomer are not excluded from the invention of the present application. When the structure of a compound is depicted as a specific cis or trans isomer, it is to be understood that the invention of the present application is not limited to that specific cis or trans isomer.

Unsubstituted alkyl groups have the general formula $C_nH_{2n+1}$ and may be linear or branched. Unsubstituted alkyl groups may also contain a cyclic moiety, and thus have the concomitant general formula $C_nH_{2n-1}$. Optionally, the alkyl groups are substituted by one or more substituents further specified in this document. Examples of alkyl groups include methyl, ethyl, propyl, 2-propyl, t-butyl, 1-hexyl, 1-dodecyl, etc.

An aryl group comprises six to twelve carbon atoms and may include monocyclic and bicyclic structures. Optionally, the aryl group may be substituted by one or more substituents further specified in this document. Examples of aryl groups are phenyl and naphthyl.

Arylalkyl groups and alkylaryl groups comprise at least seven carbon atoms and may include monocyclic and bicyclic structures. Optionally, the arylalkyl groups and alkylaryl may be substituted by one or more substituents further specified in this document. An arylalkyl group is for example benzyl. An alkylaryl group is for example 4-t-butylphenyl.

Heteroaryl groups comprise at least two carbon atoms (i.e. at least $C_2$) and one or more heteroatoms N, O, P or S. A heteroaryl group may have a monocyclic or a bicyclic structure. Optionally, the heteroaryl group may be substituted by one or more substituents further specified in this document. Examples of suitable heteroaryl groups include pyridinyl, quinolinyl, pyrimidinyl, pyrazinyl, pyrazolyl, imidazolyl, thiazolyl, pyrrolyl, furanyl, triazolyl, benzofuranyl, indolyl, purinyl, benzoxazolyl, thienyl, phospholyl and oxazolyl.

Heteroarylalkyl groups and alkylheteroaryl groups comprise at least three carbon atoms (i.e. at least $C_3$) and may include monocyclic and bicyclic structures. Optionally, the heteroaryl groups may be substituted by one or more substituents further specified in this document.

Where an aryl group is denoted as a (hetero)aryl group, the notation is meant to include an aryl group and a heteroaryl group. Similarly, an alkyl(hetero)aryl group is meant to include an alkylaryl group and a alkylheteroaryl group, and (hetero)arylalkyl is meant to include an arylalkyl group and a heteroarylalkyl group. A $C_2$-$C_{24}$ (hetero)aryl group is thus to be interpreted as including a $C_2$-$C_{24}$ heteroaryl group and a $C_6$-$C_{24}$ aryl group. Similarly, a $C_3$-$C_{24}$ alkyl(hetero)aryl group is meant to include a $C_7$-$C_{24}$ alkylaryl group and a $C_3$-$C_{24}$ alkylheteroaryl group, and a $C_3$-$C_{24}$ (hetero)arylalkyl is meant to include a $C_7$-$C_{24}$ arylalkyl group and a $C_3$-$C_{24}$ heteroarylalkyl group.

Unless stated otherwise, alkyl groups, alkenyl groups, alkenes, alkynes, (hetero)aryl groups, (hetero)arylalkyl groups and alkyl(hetero)aryl groups may be substituted with one or more substituents selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_5$-$C_{12}$ cycloalkenyl groups, $C_8$-$C_{12}$ cycloalkynyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens, amino groups, oxo and silyl groups, wherein the silyl groups can be represented by the formula $(R^{10})_3Si$—, wherein $R^{10}$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more heteroatoms selected from the group consisting of O, N and S.

An alkynyl group comprises a carbon-carbon triple bond. An unsubstituted alkynyl group comprising one triple bond has the general formula $C_nH_{2n-3}$. A terminal alkynyl is an alkynyl group wherein the triple bond is located at a terminal position of a carbon chain. Optionally, the alkynyl group is substituted by one or more substituents further specified in this document, and/or interrupted by heteroatoms selected from the group of oxygen, nitrogen and sulphur. Examples of alkynyl groups include ethynyl, propynyl, butynyl, octynyl, etc.

A cycloalkynyl group is a cyclic alkynyl group. An unsubstituted cycloalkynyl group comprising one triple bond has the general formula $C_nH_{2n-5}$. Optionally, a cycloalkynyl group is substituted by one or more substituents further specified in this document. An example of a cycloalkynyl group is cyclooctynyl.

A heterocycloalkynyl group is a cycloalkynyl group interrupted by heteroatoms selected from the group of oxygen, nitrogen and sulphur. Optionally, a heterocycloalkynyl group is substituted by one or more substituents further specified in this document. An example of a heterocycloalkynyl group is azacyclooctynyl.

A (hetero)aryl group comprises an aryl group and a heteroaryl group. An alkyl(hetero)aryl group comprises an alkylaryl group and an alkylheteroaryl group. A (hetero)arylalkyl group comprises a arylalkyl group and a heteroarylalkyl groups. A (hetero)alkynyl group comprises an alkynyl group and a heteroalkynyl group. A (hetero)cycloalkynyl group comprises an cycloalkynyl group and a heterocycloalkynyl group.

A (hetero)cycloalkyne compound is herein defined as a compound comprising a (hetero)cycloalkynyl group.

Several of the compounds disclosed in this description and in the claims may be described as fused (hetero)cycloalkyne compounds, i.e. (hetero)cycloalkyne compounds wherein a second ring structure is fused, i.e. annelated, to the (hetero)cycloalkynyl group. For example in a fused (hetero)cyclooctyne compound, a cycloalkyl (e.g. a cyclopropyl) or an arene (e.g. benzene) may be annelated to the (hetero)cyclooctynyl group. The triple bond of the (hetero)cyclooctynyl group in a fused (hetero)cyclooctyne compound may be located on either one of the three possible locations, i.e. on the 2, 3 or 4 position of the cyclooctyne moiety (numbering according to "IUPAC Nomenclature of Organic Chemistry", Rule A31.2). The description of any fused (hetero)cyclooctyne compound in this description and in the claims is meant to include all three individual regioisomers of the cyclooctyne moiety.

When an alkyl group, a (hetero)aryl group, alkyl(hetero)aryl group, a (hetero)arylalkyl group, a (hetero)cycloalkynyl group is optionally substituted, said groups are independently optionally substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens, amino groups, oxo groups and silyl groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N and S, wherein the silyl groups are represented by the formula $(R^6)_3Si$—, wherein $R^6$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N and S.

The general term "sugar" is herein used to indicate a monosaccharide, for example glucose (Glc), galactose (Gal), mannose (Man) and fucose (Fuc). The term "sugar derivative" is herein used to indicate a derivative of a monosaccharide sugar, i.e. a monosaccharide sugar comprising substituents and/or functional groups. Examples of a sugar derivative include amino sugars and sugar acids, e.g. glucosamine (GlcN), galactosamine (GalN) N-acetylglucosamine (GlcNAc), N-acetylgalactosamine (GalNAc), sialic acid (Sia) which is also referred to as N-acetylneuraminic acid (NeuNAc), and N-acetylmuramic acid (MurNAc), glucuronic acid (GlcA) and iduronic acid (IdoA). Examples of a sugar derivative also include compounds herein denoted $Su(A)_x$, wherein Su is a sugar or a sugar derivative, and wherein Su comprises x functional groups A.

The term "nucleotide" herein refers to a molecule that is composed of a nucleobase, a five-carbon sugar (either ribose or 2-deoxyribose), and one, two or three phosphate groups. Without the phosphate group, the nucleobase and sugar compose a nucleoside. A nucleotide can thus also be called a nucleoside monophosphate, a nucleoside diphosphate or a nucleoside triphosphate. The nucleobase may be adenine, guanine, cytosine, uracil or thymine. Examples of a nucleotide include uridine diphosphate (UDP), guanosine diphosphate (GDP), thymidine diphosphate (TDP), cytidine diphosphate (CDP) and cytidine monophosphate (CMP).

The term "protein" is herein used in its normal scientific meaning. Herein, polypeptides comprising about 10 or more amino acids are considered proteins. A protein may comprise natural, but also unnatural amino acids.

The term "glycoprotein" herein refers to a protein comprising one or more monosaccharide or oligosaccharide chains ("glycans") covalently bonded to the protein. A glycan may be attached to a hydroxyl group on the protein (O-linked-glycan), e.g. to the hydroxyl group of serine, threonine, tyrosine, hydroxylysine or hydroxyproline, or to an amide function on the protein (N-glycoprotein), e.g. asparagine or arginine, or to a carbon on the protein (C-glycoprotein), e.g. tryptophan. A glycoprotein may comprise more than one glycan, may comprise a combination of one or more monosaccharide and one or more oligosaccharide glycans, and may comprise a combination of N-linked, O-linked and C-linked glycans. It is estimated that more than 50% of all proteins have some form of glycosylation and therefore qualify as glycoprotein. Examples of glycoproteins include PSMA (prostate-specific membrane antigen), CAL (candida antartica lipase), gp41, gp120, EPO (erythropoietin), antifreeze protein and antibodies.

The term "glycan" herein refers to a monosaccharide or oligosaccharide chain that is linked to a protein. The term glycan thus refers to the carbohydrate-part of a glycoprotein. The glycan is attached to a protein via the C-1 carbon of one sugar, which may be without further substitution (monosaccharide) or may be further substituted at one or more of its hydroxyl groups (oligosaccharide). A naturally occurring glycan typically comprises 1 to about 10 saccharide moieties. However, when a longer saccharide chain is linked to a protein, said saccharide chain is herein also considered a glycan.

A glycan of a glycoprotein may be a monosaccharide. Typically, a monosaccharide glycan of a glycoprotein consists of a single N-acetylglucosamine (GlcNAc), glucose (Glc), mannose (Man) or fucose (Fuc) covalently attached to the protein.

A glycan may also be an oligosaccharide. An oligosaccharide chain of a glycoprotein may be linear or branched. In an oligosaccharide, the sugar that is directly attached to the protein is called the core sugar. In an oligosaccharide, a sugar that is not directly attached to the protein and is attached to at least two other sugars is called an internal sugar. In an oligosaccharide, a sugar that is not directly attached to the protein but to a single other sugar, i.e. carrying no further sugar substituents at one or more of its other hydroxyl groups, is called a terminal sugar. For the avoidance of doubt, there may exist multiple terminal sugars in an oligosaccharide of a glycoprotein, but only one core sugar.

A glycan may be an O-linked glycan, an N-linked glycan or a C-linked glycan. In an O-linked glycan a monosaccharide or oligosaccharide glycan is bonded to an O-atom in an amino acid of the protein, typically via a hydroxyl group of serine (Ser) or threonine (Thr). In an N-linked glycan a monosaccharide or oligosaccharide glycan is bonded to the protein via an N-atom in an amino acid of the protein, typically via an amide nitrogen in the side chain of asparagine (Asn) or arginine (Arg). In a C-linked glycan a monosaccharide or oligosaccharide glycan is bonded to a C-atom in an amino acid of the protein, typically to a C-atom of tryptophan (Trp).

The end of the oligosaccharide that is directly attached to the protein is called the reducing end. The other end of the oligosaccharide is called the non-reducing end of the glycan.

For O-linked glycans, a wide diversity of chains exist. Naturally occurring O-linked glycans typically feature a serine or threonine-linked α-O-GalNAc moiety, further substituted with galactose, sialic acid and/or fucose. The hydroxylated amino acid that carries the glycan substitution may be part of any amino acid sequence in the protein.

For N-linked glycans, a wide diversity of chains exist. Naturally occurring N-linked glycans typically feature an asparagine-linked β-N-GlcNAc moiety, in turn further substituted at its 4-OH with β-GlcNAc, in turn further substituted at its 4-OH with β-Man, in turn further substituted at its 3-OH and 6-OH with α-Man, leading to the glycan pentasaccharide $Man_3GlcNAc_2$. The core GlcNAc moiety may be further substituted at its 6-OH by α-Fuc. The pentasaccharide $Man_3GlcNAc_2$ is the common oligosaccharide scaffold of nearly all N-linked glycoproteins and may carry a wide variety of other sub stituents, including but not limited to Man, GlcNAc, Gal and sialic acid. The asparagine that is substituted with the glycan on its side-chain is typically part of the sequence Asn-X-Ser/Thr, with X being any amino acid but proline and Ser/Thr being either serine or threonine.

A glycan of the formula $GlcNAcMan_5GlcNAc_2$ is herein defined as a glycan having structure (101), and a glycan of the formula $Su(A)_xGlcNAcMan_5GlcNAc_2$ is herein defined as a glycan having structure (102), as shown below. $Su(A)_x$ is defined elsewhere in this document. $GlcNAcMan_5GlcNAc_2$ (101) may also be referred to as "$GnM_5$".

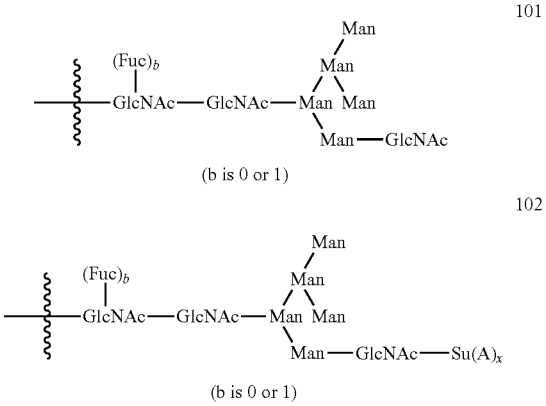

In glycan (102), the $Su(A)_x$-group is bonded to the GlcNAc-moiety at the non-reducing end of glycan (102).

The GlcNAc moiety via which glycan (101) or (102) is bonded to the protein is referred to as the core-GlcNAc moiety of (101) or (102). Optionally, the core-GlcNAc moiety of (101) and (102) is fucosylated, i.e. b is 0 (non-fucosylated) or 1 (fucosylated). In a glycoprotein, the (optionally fucosylated) core-GlcNAc moiety of glycan (101) and (102) is bonded to the protein via C1, preferably via an N-glycosidic bond to the amide nitrogen atom in the side chain of an asparagine amino acid of the protein. Glycan (101) and (102) may be present at a native glycosylation site of the protein, but may also be introduced on a different site on the protein.

If the core-GlcNAc moiety in glycan (101) or (102) is fucosylated, fucose is most commonly linked α-1,6 to C6 of the core-GlcNAc moiety. A fucosylated $GlcNAcMan_5GlcNAc_2$ glycan may be denoted $GlcNAcMan_5GlcNAcGlcNAc(Fuc)$, and a fucosylated $Su(A)_xGlcNAcMan_5GlcNAc_2$ glycan may be denoted $Su(A)_xGlcNAcMan_5GlcNAcGlcNAc(Fuc)$.

The terms "antibody" and "immunoglobulin (Ig)" are herein used in their normal scientific meaning. An antibody is a protein generated by the immune system that is capable of recognizing and binding to a specific antigen. An antibody is an example of a glycoprotein. The term antibody herein is used in its broadest sense and specifically includes monoclonal antibodies, polyclonal antibodies, dimers, multimers, multispecific antibodies (e.g. bispecific antibodies), antibody fragments, and double and single chain antibodies. The term "antibody" is herein also meant to include human antibodies, humanized antibodies, chimeric antibodies and antibodies specifically binding cancer antigen. The term "antibody" is meant to include whole antibodies, preferably of the G type, i.e. IgG antibodies, but also fragments of an antibody, for example an antibody Fab fragment, F(ab')₂, Fv fragment or Fc fragment from a cleaved antibody, a scFv-Fc fragment, a minibody, a diabody or a scFv. Furthermore, the term includes genetically engineered antibodies and derivatives of an antibody. Antibodies, fragments of antibodies and genetically engineered antibodies may be obtained by methods that are known in the art. Suitable marketed antibodies include, amongst others, abciximab, rituximab, basiliximab, palivizumab, infliximab, trastuzumab, alemtuzumab, adalimumab, tositumomab-I131, cetuximab, ibrituximab tiuxetan, omalizumab, bevacizumab, natalizumab, ranibizumab, panitumumab, eculizumab, certolizumab pegol, golimumab, canakinumab, catumaxomab, ustekinumab, tocilizumab, ofatumumab, denosumab, belimumab, ipilimumab and brentuximab.

The terms "treatment," "treating," and the like refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes preventing the disease from occurring in a subject which may be predisposed to the disease but has not yet been diagnosed as having it; inhibiting the disease, i.e., arresting its development; relieving the disease, i.e., causing regression of the disease.

Process for the Preparation of a Modified Glycoprotein

The present invention relates to a process for the preparation of a modified glycoprotein, the process comprising contacting a glycoprotein comprising a glycan of the formula GlcNAcMan$_5$GlcNAc$_2$ with Su(A)$_x$-P in the presence of a suitable catalyst; wherein the core GlcNAc residue of said glycan is optionally fucosylated; wherein a suitable catalyst is defined as a galactosyltransferase or a galactosyltransferase comprising a mutant catalytic domain, wherefore Su(A)$_x$-P is a substrate; wherein Su(A)$_x$ is a sugar derivative comprising x functional groups A wherein x is 1, 2, 3 or 4 and A is independently selected from the group consisting of an azido group, a keto group, an alkynyl group, a thiol group or a precursor thereof, a halogen, a sulfonyloxy group, a halogenated acetamido group, a mercaptoacetamido group and a sulfonylated hydroxyacetamido group; wherein P is a nucleotide; wherein a modified glycoprotein is defined as a glycoprotein comprising a glycan of the formula Su(A)$_x$GlcNAcMan$_5$GlcNAc$_2$ wherein the core GlcNAc residue is optionally fucosylated; and wherein GlcNAcMan$_5$GlcNAc$_2$ is a glycan according to formula (101) and Su(A)$_x$GlcNAcMan$_5$GlcNAc$_2$ is a glycan according to formula (102):

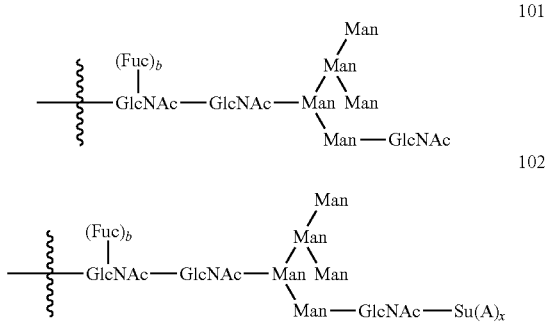

wherein b is 0 or 1 and Su(A)$_x$ is as defined above.

As described above, the term "sugar derivative" herein refers to a derivative of a monosaccharide sugar, i.e. a monosaccharide sugar comprising substituents and/or functional groups.

Preferably, the catalyst is selected from the group consisting of β(1,4)-galactosyltransferases, β(1,3)-N-galactosyltransferases, β(1,4)-galactosyltransferases comprising a mutant catalytic domain and β(1,3)-N-galactosyltransferases comprising a mutant catalytic domain.

The present invention therefore relates to a process for the preparation of a modified glycoprotein, comprising contacting a glycoprotein comprising a GlcNAcMan$_5$GlcNAc$_2$ glycan with Su(A)$_x$-P in the presence of a catalyst selected from the group consisting of β(1,4)-galactosyltransferases, β(1,3)-N-galactosyltransferases, β(1,4)-galactosyltransferases comprising a mutant catalytic domain and β(1,3)-N-galactosyltransferases comprising a mutant catalytic domain; wherein the core GlcNAc residue of said glycan is optionally fucosylated; wherein Su(A)$_x$ is a monosaccharide sugar derivative comprising x functional groups A wherein x is 1, 2, 3 or 4 and A is independently selected from the group consisting of an azido group, a keto group, an alkynyl group, a thiol group or a precursor thereof, a halogen, a sulfonyloxy group, a halogenated acetamido group, a mercaptoacetamido group and a sulfonylated hydroxyacetamido group; wherein P is a nucleotide; wherein a modified glycoprotein is defined as a glycoprotein comprising a Su(A)$_x$GlcNAcMan$_5$GlcNAc$_2$ glycan wherein the core GlcNAc residue is optionally fucosylated; and wherein GlcNAcMan$_5$GlcNAc$_2$ is a glycan according to formula (101) and Su(A)$_x$GlcNAcMan$_5$GlcNAc$_2$ is a glycan according to formula (102):

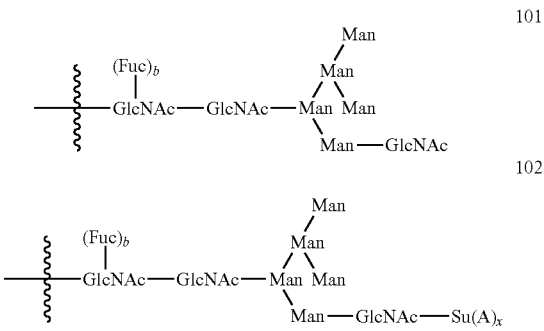

wherein b is 0 or 1 and Su(A)$_x$ is as defined above.

The protein comprising a glycan of the formula GlcNAcMan$_5$GlcNAc$_2$ may comprise one or more glycans (101). The one or more glycans (101) may be situated anywhere on the protein. Said one or more glycans may be present on a native glycosylation site of the protein, and/or may be introduced on a non-native site of the protein by glycoengineering techniques. The one or more glycans (101) are bonded to the protein via C1 of the, optionally fucosylated, core-GlcNAc moiety of glycan (101). The one or more glycans (101) may be bonded to the protein via an N-glycosidic bond and/or via an O-glycosidic bond. In a preferred embodiment, the one or more glycans (101) are bonded to the protein via an N-linked glycosidic bond, more preferably via an N-glycosidic bond to an amide nitrogen atom in the side chain of an asparagine amino acid present in the glycoprotein.

In a preferred embodiment, the glycoprotein to be modified is a glycoprotein according to formula (103), and the modified glycoprotein is a glycoprotein according to formula (104):

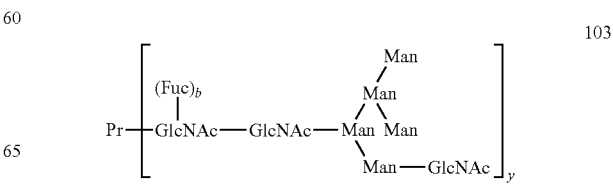

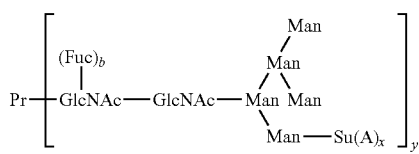

wherein Pr represents a protein, b is 0 or 1 and y is 1 to 20. The core-GlcNAc moiety of protein (103) or (104) is optionally fucosylated (b is 0 or 1).

Preferably, y is 1 to 10, more preferably y is 1, 2, 3, 4, 5, 6, 7 or 8, even more preferably y is 1, 2, 3 or 4. In the process according to the invention for the modification of a glycoprotein, a glycoprotein comprising a glycan (102) is obtained from a glycoprotein comprising a glycan (101) by introduction of a $Su(A)_x$-group to the terminal GlcNAc-moiety of a glycan (101).

$Su(A)_x$ and preferred embodiments thereof are described in more detail below.

In another preferred embodiment, the protein to be modified (103) is an antibody (Ab), i.e. in a preferred embodiment Pr in protein (103) is Ab. Therefore, in a preferred embodiment the glycoprotein comprising a glycan of the formula GlcNAcMan$_5$GlcNAc$_2$ is an antibody comprising a glycan of the formula GlcNAcMan$_5$GlcNAc$_2$. The antibody is described in more detail below.

The present invention therefore also relates to a process for the preparation of a modified antibody, the process comprising contacting an antibody comprising a glycan of the formula GlcNAcMan$_5$GlcNAc$_2$ with $Su(A)_x$-P in the presence of a suitable catalyst; wherein the core GlcNAc residue of said glycan is optionally fucosylated; wherein a suitable catalyst is defined as a galactosyltransferase or a galactosyltransferase comprising a mutant catalytic domain, wherefore $Su(A)_x$-P is a substrate; wherein $Su(A)_x$ is a sugar derivative comprising x functional groups A wherein x is 1, 2, 3 or 4 and A is independently selected from the group consisting of an azido group, a keto group, an alkynyl group, a thiol group or a precursor thereof, a halogen, a sulfonyloxy group, a halogenated acetamido group, a mercaptoacetamido group and a sulfonylated hydroxyacetamido group; wherein P is a nucleotide; wherein a modified antibody is defined as an antibody comprising a glycan of the formula $Su(A)_x$GlcNAcMan$_5$GlcNAc$_2$ wherein the core GlcNAc residue is optionally fucosylated; and wherein GlcNAcMan$_5$GlcNAc$_2$ is a glycan according to formula (101) and $Su(A)_x$GlcNAcMan$_5$GlcNAc$_2$ is a glycan according to formula (102); and wherein Ab represents an antibody, and b, y and $Su(A)x$ are as defined above. The modified antibody is according to formula (104), wherein Pr represents an antibody.

A preferred embodiment of the process according to the invention for the preparation of a modified antibody is shown in Scheme 1, wherein a modified antibody (104b) comprising a glycan according to formula (102) is prepared from an antibody (103b) comprising a glycan according to formula (101).

Scheme 1

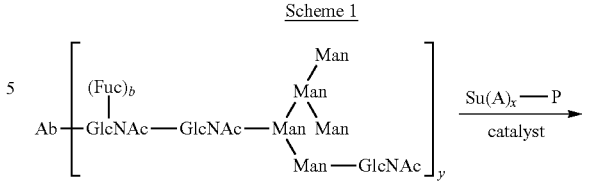

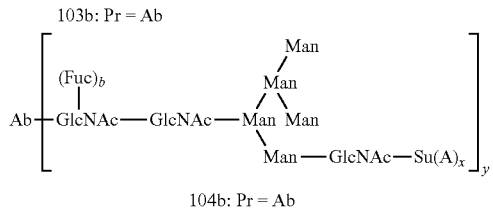

Figure 18:
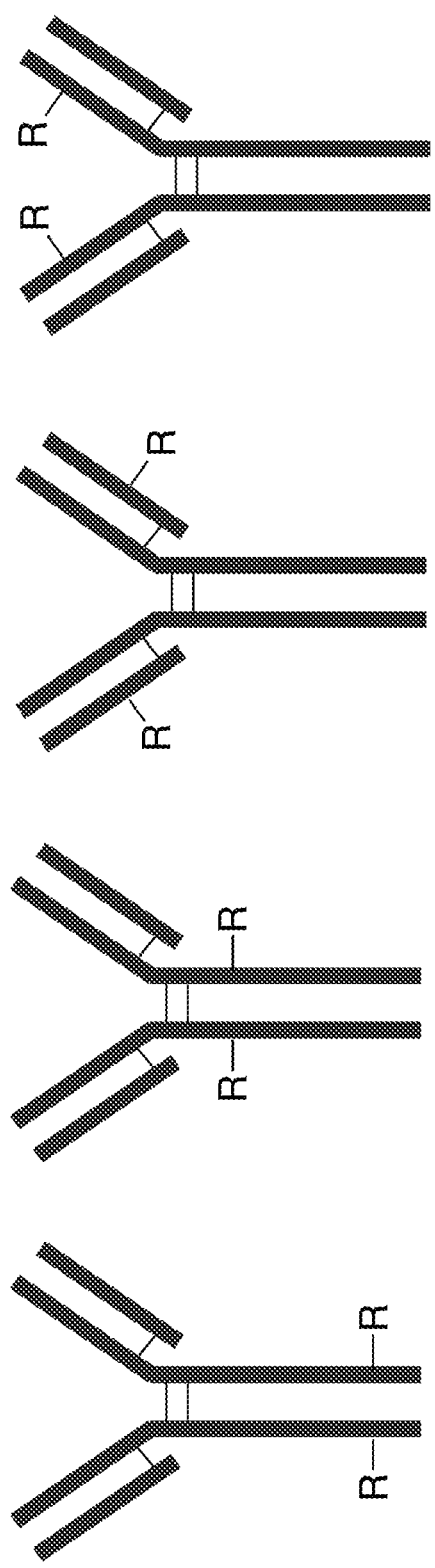
FIG. 18 shows different glycoforms of a monoclonal antibody, e.g. IgG, which can be obtained by removing the native glycosylation site of a mAb and engineering a glycosylation site (based on sequence N—X—S/T, with X is any amino acid except proline) at another position.

In this embodiment, preferably y is 1 to 10, more preferably y is 1, 2, 3, 4, 5, 6, 7 or 8, even more preferably y is 1, 2, 3 or 4. When the antibody is a whole antibody, it is further preferred that y is 2 or 4, preferably 2. When the antibody is an antibody fragment, it is further preferred that y is 1 or 2, preferably 1. $Su(A)_x$ and preferred embodiments thereof are described in more detail below The antibody comprising a glycan of the formula GlcNAcMan$_5$GlcNAc$_2$, i.e. the starting material of the process for preparation of a modified antibody, comprises one or more glycans (101). The one or more glycans (101) may be situated anywhere on the antibody, provided that said one or more glycans do not hinder the antigen-binding site of the antibody. In one embodiment, said one or more glycans (101) are situated in the Fc fragment of the antibody, more preferably in the $C_H2$ domain. In another embodiment, said one or more glycans (101) are situated on the Fab fragment of the antibody. As was described above, the one or more glycans (101) are bonded to the antibody via C1 of the, optionally fucosylated, core-GlcNAc moiety of the one or more glycans (101). In a preferred embodiment, the one or more glycans (101) are bonded to the antibody via an N-glycosidic bond, more preferably via an N-glycosidic bond to an amide nitrogen atom in the side chain of an asparagine amino acid present in the antibody. The one or more glycans (101) may be present on a conserved (i.e. native) glycosylation site of the antibody, and/or may be introduced on a non-native site of the antibody by glycoengineering techniques. Several examples of the position of a glycosylation site in an antibody are shown in FIG. 18.

In the process for the modification of an antibody according to the invention, an antibody mixture may be used as the starting antibody, said mixture comprising antibodies comprising one or more non-fucosylated glycans (101) and/or one or more fucosylated fucosylated glycans (101). Advantageously, removal of fucose prior to the process according to the invention is therefore not necessary, since an antibody mixture comprising both fucosylated and non-fucosylated glycans (101) may be used in the process.

In a preferred embodiment, said antibody is a monoclonal antibody (mAb). Preferably, said antibody is selected from the group consisting of IgA, IgD, IgE, IgG and IgM antibodies. More preferably, said antibody is an IgG antibody, and most preferably said antibody is an IgG1 antibody. When said antibody is a whole antibody, the antibody preferably comprises one or more, more preferably one, glycan (101) on each heavy chain. Said whole antibody thus preferably comprises two or more, preferably two, four, six or eight glycans (101), more preferably two or four, and most preferably two glycans (101). In other words, when said antibody is a whole antibody, y is preferably 2, 4, 6 or 8, more preferably y is 2 or 4, and most preferably y is 2. When said antibody is a single chain antibody or an antibody fragment, e.g. a Fab fragment, the antibody preferably comprises one or more glycan (101).

In a preferred embodiment, a glycan (101) in an antibody is attached to the conserved N-glycosylation site in the Fc-fragment of the antibody. In a further preferred embodiment, said glycan is attached to an asparagine amino acid in the region 290-305. In a further preferred embodiment, the antibody is an IgG type antibody, and, depending on the particular IgG type antibody, said glycan is preferably present on amino acid asparagine 297 (Asn297 or N297) of the antibody. In another preferred embodiment, the glycoprotein in an antibody is attached to a non-native glycosylation site in the antibody. It is further preferred that said non-native glycosylation site is a non-native N-glycosylation site. A non-native glycosylation site may be introduced into the antibody via glycoengineering techniques. Several examples of the position of a glycosylation site in an antibody are shown in FIG. 18.

In a further preferred embodiment of the process for the preparation of a modified antibody according to the invention, an antibody (103b, with y is 2) comprising an optionally fucosylated glycan according to formula (101), is reacted with Su(A)x-P in the presence of a catalyst to form a modified antibody (104b, with y is 2) comprising an optionally fucosylated glycan according to formula (102). Su(A)$_x$ and preferred embodiments thereof are described in more detail below.

The process for the preparation of a modified glycoprotein according to the invention is performed in the presence of a suitable catalyst. A suitable catalyst is defined as a galactosyltransferase, or a galactosyltransferase comprising a mutant catalytic domain, wherefore Su(A)$_x$-P is a substrate. When the catalyst is a galactosyltransferase, said galactosyltransferase preferably is a wild-type galactosyltransferase. When the catalyst is a galactosyltransferase comprising a mutant catalytic domain, said mutant GalT domain may be present within a full-length GalT enzyme, but it may also be present in a recombinant molecule comprising a catalytic domain.

Preferably, the process for the preparation of a modified glycoprotein according to the invention is performed in the presence of a catalyst selected from the group consisting of β(1,4)-galactosyltransferases, β(1,3)-N-galactosyltransferases, β(1,4)-galactosyltransferases comprising a mutant catalytic domain and β(1,3)-N-galactosyltransferases comprising a mutant catalytic domain.

In one embodiment, the catalyst is a wild-type galactosyltransferase, more preferably a wild-type β(1,4)-galactosyltransferase or a wild-type β(1,3)-N-galactosyltransferase, and even more preferably a wild-type β(1,4)-galactosyltransferase I. β(1,4)-Galactosyltransferase I is herein further referred to as GalT. Even more preferably, the β(1,4)-galactosyltransferase I is selected from the group consisting of a bovine β(1,4)-Gal-T1, a human β(1,4)-Gal-T1, a human β(1,4)-Gal-T2, a human β(1,4)-Gal-T3 and a human β(1,4)-Gal-T4. When the catalyst is a wild-type β(1,3)-N-galactosyltransferase, a human β(1,3)-Gal-T5 is preferred.

This embodiment wherein the catalyst is a wild-type galactosyltransferase is particularly preferred when a functional group A in sugar derivative Su(A)$_x$ is present on C6 of said sugar derivative. In this embodiment, it is further preferred that Su(A)$_x$ comprises one functional group A, i.e. preferably x is 1. Su(A)$_x$ and Su(A)$_x$-P are described in more detail below.

The present invention thus also relates to a process for the preparation of a modified glycoprotein, the process comprising contacting a glycoprotein comprising a glycan of the formula GlcNAcMan$_5$GlcNAc$_2$ with Su(A)$_x$-P in the presence of a suitable catalyst; wherein the core GlcNAc residue of said glycan is optionally fucosylated; wherein a suitable catalyst is defined as a galactosyltransferase or a galactosyltransferase comprising a mutant catalytic domain, wherefore Su(A)$_x$-P is a substrate; wherein Su(A)$_x$ is a sugar derivative comprising x functional groups A wherein x is 1, 2, 3 or 4 and A is independently selected from the group consisting of an azido group, a keto group, an alkynyl group, a thiol group or a precursor thereof, a halogen, a sulfonyloxy group, a halogenated acetamido group, a mercaptoacetamido group and a sulfonylated hydroxyacetamido group; wherein P is a nucleotide; wherein a modified glycoprotein is defined as a glycoprotein comprising a glycan of the formula Su(A)$_x$GlcNAcMan$_5$GlcNAc$_2$ wherein the core GlcNAc residue is optionally fucosylated; and wherein GlcNAcMan$_5$GlcNAc$_2$ is a glycan according to formula (101) and Su(A)$_x$GlcNAcMan$_5$GlcNAc$_2$ is a glycan according to formula (102):

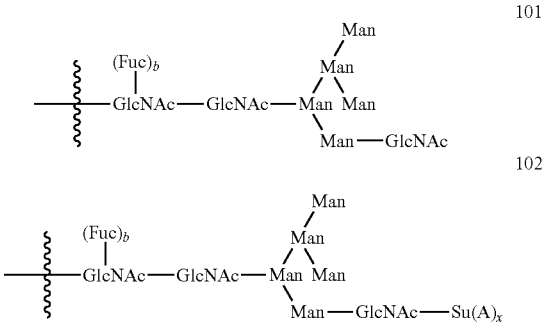

wherein b is 0 or 1 and Su(A)$_x$ is as defined above; with the proviso that when the catalyst is a wild-type galactosyltransferase, then Su(A)$_x$-P comprises one functional group A (i.e. x is 1), and said functional group A is present on C2 or C6, preferably C6 of Su(A)$_x$.

Accordingly, the invention therefore relates to a process for the preparation of a modified glycoprotein, the process comprising contacting a glycoprotein comprising a glycan of the formula GlcNAcMan$_5$GlcNAc$_2$ with Su(A)$_x$-P in the presence of a suitable catalyst; wherein the core GlcNAc residue of said glycan is optionally fucosylated; wherein a suitable catalyst is defined as a wild-type galactosyltransferase wherefore Su(A)$_x$-P is a substrate; wherein Su(A)$_x$ is a sugar derivative comprising x functional groups A wherein x is 1, A is present on C2 or C6, preferably C6, of sugar derivative Su and A is independently selected from the group consisting of an azido group, a keto group, an alkynyl group, a thiol group or a precursor thereof, a halogen, a sulfonyloxy group, a halogenated acetamido group, a mercaptoacetamido group and a sulfonylated hydroxyacetamido group; wherein P is a nucleotide; wherein a modified glycoprotein is defined as a glycoprotein comprising a glycan of the formula Su(A)$_x$GlcNAcMan$_5$GlcNAc$_2$ wherein the core GlcNAc residue is optionally fucosylated; and wherein GlcNAcMan$_5$GlcNAc$_2$ is a glycan according to formula (101) and Su(A)$_x$GlcNAcMan$_5$GlcNAc$_2$ is a glycan according to formula (102):

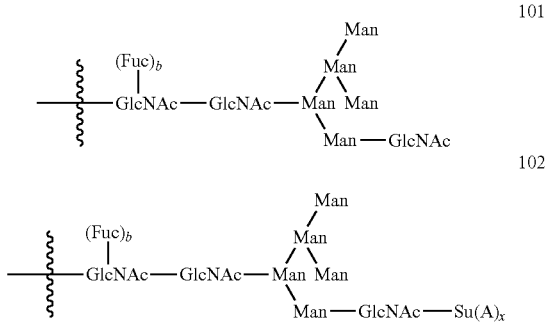

wherein b is 0 or 1 and Su(A)$_x$ is as defined above.

Preferably, the wild-type galactosyltransferase is a β(1,4)-galactosyltransferase or a β(1,3)-N-galactosyltransferase, more preferably a β(1,4)-galactosyltransferase. Even more preferably, the wild-type a β(1,4)-galactosyltransferase is a wild-type human GalT, more preferably a wild-type human GalT selected from the group consisting of a wild-type human β-Gal-T1, a wild-type human β(1,4)-Gal-T2, a wild-type human β(1,4)-Gal-T3 and a wild-type human β(1,4)-Gal-T4.

In another embodiment the catalyst is a galactosyltransferase comprising a mutant catalytic domain, preferably a β(1,4)-galactosyltransferase comprising a mutant catalytic domain or a β(1,3)-N-galactosyltransferase comprising a mutant catalytic domain, more preferably a β(1,4)-galactosyltransferase comprising a mutant catalytic domain. β(1,4)-Galactosyltransferase I is herein further referred to as GalT.

In a preferred embodiment the catalyst is a β(1,3)-N-galactosyltransferase comprising a mutant catalytic domain, and preferably said β(1,3)-N-galactosyltransferase is a human β(1-3)-Gal-T5.

More preferably, the catalyst is a β(1,4)-N-galactosyltransferase comprising a mutant catalytic domain, more preferably, a β(1,4)-galactosyltransferase I comprising a mutant catalytic domain, and even more preferably selected from the group consisting of a bovine β(1,4)-Gal-T1, a human β-Gal-T1, a human β(1,4)-Gal-T2, a human β(1,4)-Gal-T3 and a human β(1,4)-Gal-T4, all comprising a mutant catalytic domain.

Most preferably the catalyst is a bovine β(1,4)-Gal-T1 comprising a mutant catalytic domain.

In another embodiment, the catalyst is selected from the group consisting of a β(1,4)-Gal-T1, a β(1,4)-Gal-T1, a β(1,4)-Gal-T2, a β(1,4)-Gal-T4 and a human β(1,3)-Gal-T5. In a preferred embodiment, the catalyst is selected from the group consisting of a wild-type bovine β(1,4)-Gal-T1, a wild-type human β(1,4)4-Gal-T1, a wild-type human β(1,4)-Gal-T2, a wild-type human β(1,4)-Gal-T4 and a wild-type human β(1,3)-Gal-T5. In another preferred embodiment, the catalyst is selected from the group consisting of a bovine β(1,4)-Gal-T1, a human β(1,4)4-Gal-T1, a human β(1,4)-Gal-T2, a human β(1,4)-Gal-T4 and a human β(1,3)-Gal-T5, all comprising a mutant catalytic domain.

In a preferred embodiment of the process according to the invention, the catalyst is a galactosyltransferase comprising a mutant catalytic domain.

Several suitable catalysts for the process according to the invention are known in the art. A suitable catalyst is for example a catalyst that comprises a mutant catalytic domain from a β(1,4)-galactosyltransferase I. A catalytic domain herein refers to an amino acid segment that folds into a domain that is able to catalyze the linkage of the specific sugar derivative nucleotide Su(A)$_x$-P to the terminal non-reducing GlcNAc-glycan in a specific process according to the invention. β(1,4)-galactosyltransferase I is herein further referred to as GalT. Such mutant GalT catalytic domains are for example disclosed in *J. Biol. Chem.* 2002, 277, 20833 and WO 2004/063344 (National Institutes of Health), incorporated by reference herein. *J. Biol. Chem.* 2002, 277, 20833 and WO 2004/063344 disclose Tyr-289 mutants of bovine β(1,4)-Gal-T1, which are referred to as Y289L, Y289N and Y289I. The method of preparation of said mutant catalytic domains Y289L, Y289N and Y289I is disclosed in detail in WO 2004/063344, p. 34, 1. 6-p. 36, 1. 2, expressly incorporated by reference herein.

Mutant GalT domains that catalyze the formation of a glucose-β(1,4)-N-acetylglucosamine bond are disclosed in WO 2004/063344 on p. 10, 1, 25-p. 12, 1. 4 (expressly incorporated by reference herein). Mutant GalT domains that catalyze the formation of an N-acetylgalactosamine-β(1,4)-N-acetylglucosamine bond are disclosed in WO 2004/063344 on p. 12, 1, 6-p. 13, 1. 2 (expressly incorporated by reference herein). Mutant GalT domains that catalyze the formation of a N-acetylglucosamine-β(1,4)-N-acetylglucosamine bond and a mannose-β(1,4)-N-acetylglucosamine bond are disclosed in WO 2004/063344 on p. 12, 1, 19-p. 14, 1. 6 (expressly incorporated by reference herein).

The disclosed mutant GalT domains may be included within full-length GalT enzymes, or in recombinant molecules containing the catalytic domains, as is disclosed in WO 2004/063344 on p. 14, 1, 31-p. 16, 1. 28, expressly incorporated by reference herein.

Another mutant GalT domain is for example Y284L, disclosed by Bojarová et al., *Glycobiology* 2009, 19, 509, expressly incorporated by reference herein, wherein Tyr284 is replaced by leucine.

Another mutant GalT domain is for example R228K, disclosed by Qasba et al., *Glycobiology* 2002, 12, 691, expressly incorporated by reference herein, wherein Arg228 is replaced by lysine.

The catalyst may also comprise a mutant catalytic domain from a bovine β(1,4)-galactosyltransferase, selected from the group consisting of GalT Y289N, GalT Y289F, GalT Y289M, GalT Y289V, GalT Y289G, GalT Y289I and GalT Y289A, preferably selected from the group consisting of GalT Y289F and GalT Y289M, GalT Y289N, GalT Y289F, GalT Y289M, GalT Y289V, GalT Y289G, GalT Y289I and GalT Y289A may be provided via site-directed mutagenesis processes, in a similar manner as disclosed in WO 2004/063344, in Qasba et al., *Prot. Expr. Pur.* 2003, 30, 219 and in Qasba et al., *J. Biol. Chem.* 2002, 277, 20833 (all incorporated by reference) for Y289L, Y289N and Y289I. In GalT Y289N the tyrosine amino acid (Y) at position 289 is replaced by an asparagine (N) amino acid, in GalT Y289F the tyrosine amino acid (Y) at position 289 is replaced by a phenylalanine (F) amino acid, in GalT Y289M said tyrosine is replaced by a methionine (M) amino acid, in GalT Y289V by a valine (V) amino acid, in GalT Y289G by a glycine (G) amino acid, in GalT Y289I by an isoleucine (I) amino acid and in Y289A by an analine (A) amino acid.

In a preferred embodiment of the process for the preparation of a modified glycoprotein according to the invention, said catalyst is a catalyst comprising a mutant catalytic domain from a β(1,4)-galactosyltransferase, preferably from a bovine β(1,4)-Gal-T1.

Preferably, the catalyst is a catalyst comprising a mutant catalytic domain from a β(1,4)-galactosyltransferase, preferably selected from the group consisting of bovine β(1,4)-Gal-T1 GalT Y289L, GalT Y289N, GalT Y289I, GalT Y289F, GalT Y289M, GalT Y289V, GalT Y289G and GalT Y289A, more preferably selected from the group consisting of bovine β(1,4)-Gal-T1 GalT Y289L, GalT Y289N and GalT Y289I.

In a further preferred embodiment, said catalyst is a catalyst comprising a bovine β(1,4)-Gal-T1 mutant catalytic domain selected from the group consisting of Y289L, Y289N, Y289I, Y284L, Y290N, R228K, Y289F, Y289M, Y289V, Y289G and Y289A, preferably selected from the group consisting of Y289L, Y289N, Y289I, Y284L and R228K. In another preferred embodiment, said catalyst is a catalyst comprising a bovine β(1,4)-Gal-T1 mutant catalytic domain selected from the group consisting of Y289F, Y289M, Y289V, Y289G and Y289A. More preferably said catalyst is a catalyst comprising a bovine β(1,4)-Gal-T1 mutant catalytic domain selected from the group consisting of Y289L, Y289N, Y290N and Y289I, even more preferably of Y289L, Y289N and Y289I. Most preferably said catalyst is a catalyst comprising bovine β(1,4)-Gal-T1 mutant catalytic domain Y289L.

Another type of suitable catalysts is a catalyst based on α(1,3)-N-galactosyltransferase (further referred to as α3Gal-T), preferably α(1,3)-N-acetylgalactosaminyltransferase (further referred to as α3GalNAc-T), as disclosed in WO 2009/025646, incorporated by reference herein. Mutation of α3Gal-T can broaden donor specificity of the enzyme, and make it an α3GalNAc-T. Mutation of α3GalNAc-T can broaden donor specificity of the enzyme. Polypeptide fragments and catalytic domains of α(1,3)-N-acetylgalactosaminyltransferases are disclosed in WO 2009/025646 on p. 26, l. 18-p. 47, l. 15 and p. 77, l. 21-p. 82, l. 4 (both expressly incorporated by reference herein).

The process for the preparation of a modified glycoprotein according to the invention is preferably performed in a suitable buffer solution, such as for example phosphate, buffered saline (e.g. phosphate-buffered saline, tris-buffered saline), citrate, HEPES, tris and glycine. Suitable buffers are known in the art. Preferably, the buffer solution is phosphate-buffered saline (PBS) or tris buffer.

The process is preferably performed at a temperature in the range of about 4 to about 50° C., more preferably in the range of about 10 to about 45° C., even more preferably in the range of about 20 to about 40° C., and most preferably in the range of about 30 to about 37° C.

The process is preferably performed a pH in the range of about 5 to about 9, preferably in the range of about 5.5 to about 8.5, more preferably in the range of about 6 to about 8. Most preferably, the process is performed at a pH in the range of about 7 to about 8.

$Su(A)_x$ is defined as a sugar derivative comprising x functional groups A, wherein x is 1, 2, 3 or 4 and wherein A is independently selected from the group consisting of an azido group, a keto group an alkynyl group, a thiol group or a precursor thereof, a halogen, a sulfonyloxy group, a halogenated acetamido group, a mercaptoacetamido group and a sulfonylated hydroxyacetamido group. As described in more detail above, the general term "sugar" is herein used to indicate a monosaccharide, and the term "sugar derivative" is herein used to indicate a derivative of a monosaccharide sugar, i.e. a monosaccharide sugar comprising substituents and/or functional groups.

A $Su(A)_x$-moiety may also be referred to as a "modified sugar". A modified sugar is herein defined as a sugar or a sugar derivative, said sugar or sugar derivative comprising 1, 2, 3 or 4 functional groups A, wherein A is selected from the group consisting of an azido group, a keto group an alkynyl group, a thiol group or a precursor thereof, a halogen, a sulfonyloxy group, a halogenated acetamido group, a mercaptoacetamido group and a sulfonylated hydroxyacetamido group.

When a modified sugar or sugar derivative comprises e.g. an azido group, said sugar or sugar derivative may be referred to as an azido-modified sugar or sugar derivative. When a modified sugar or sugar derivative comprises e.g. a keto group, said sugar or sugar derivative may be referred to as a keto-modified sugar or sugar derivative. When a modified sugar or sugar derivative comprises e.g. an alkynyl group, said sugar or sugar derivative may be referred to as an alkynyl-modified sugar or sugar derivative. When a modified sugar or sugar derivative comprises e.g. a thiol group, said sugar or sugar derivative may be referred to as a thiol-modified sugar or sugar derivative. When a modified sugar or sugar derivative comprises e.g. a thiol-precursor group, said sugar or sugar derivative may be referred to as a thiol-precursor-modified sugar or sugar derivative. When a modified sugar or sugar derivative comprises e.g. a halogen, said sugar or sugar derivative may be referred to as a halogen-modified sugar or sugar derivative. When a modified sugar or sugar derivative comprises e.g. a sulfonyloxy group, said sugar or sugar derivative may be referred to as a sulfonate-modified sugar or sugar derivative.

An azido group is herein defined as a $—[C(R^7)_2]_oN_3$ group, wherein $R^7$ is independently selected from the group consisting of hydrogen, halogen and an (optionally substituted) $C_1$-$C_{24}$ alkyl group, and o is 0-24. Preferably $R^7$ is hydrogen or a $C_1$, $C_2$, $C_3$ or $C_4$ alkyl group, more preferably $R^7$ is hydrogen or —$CH_3$. Preferably o is 0-10, more preferably 0, 1, 2, 3, 4, 5 or 6. More preferably, $R^7$ is hydrogen, —$CH_3$ or a $C_2$ alkyl group and/or o is 0, 1, 2, 3 or 4. Even more preferably $R^7$ is hydrogen and o is 1 or 2. Most preferably o is 0.

A keto group is a $—[C(R^7)_2]_oC(O)R^6$ group, wherein $R^6$ is an optionally substituted methyl group or an optionally substituted $C_2$-$C_{24}$ alkyl group, $R^7$ is independently selected from the group consisting of hydrogen, halogen, methyl and $R^6$, and o is 0-24, preferably 0-10, and more preferably 0, 1, 2, 3, 4, 5 or 6. Preferably, $R^7$ is hydrogen. In a preferred embodiment, $R^6$ is an optionally substituted $C_2$-$C_{24}$ alkyl group. When $Su(A)_x$ is derived from an amino sugar, and A is a keto group bonded to the amino sugar N-atom and o is 0 (i.e. when Su(A) comprises an —NC(O)$R^6$ substituent), $R^6$ is an optionally substituted $C_2$-$C_{24}$ alkyl group.

An alkynyl group is preferably a terminal alkynyl group or a (hetero)cycloalkynyl group as defined above. In one embodiment the alkynyl group is a $—[C(R^7)_2]_oC≡C—R^7$ group, wherein $R^7$ and o are as defined above; $R^7$ is preferably hydrogen. More preferably, o is 0, 1, 2, 3, 4, 5 or 6 and $R^7$ is hydrogen. Most preferably o is 0.

A thiol group is herein defined as a $—[C(R^7)_2]_oSH$ group, wherein $R^7$ is independently selected from the group consisting of hydrogen, halogen and an (optionally substituted) $C_1$-$C_{24}$ alkyl group, and o is 0-24. Preferably $R^7$ is hydrogen or a $C_1$, $C_2$, $C_3$ or $C_4$ alkyl group, more preferably $R^7$ is hydrogen or —$CH_3$. Preferably o is 0-10, more preferably 0, 1, 2, 3, 4, 5 or 6. More preferably, $R^7$ is hydrogen, —$CH_3$ or a $C_2$ alkyl group and/or o is 0, 1, 2, 3 or 4. Even more preferably $R^7$ is hydrogen and o is 0, 1, 2 or 3, more preferably o is 1 or 2, most preferably o is 0 or 1. Most preferably o is 0. In a particularly preferred embodiment, $R^7$ is hydrogen and o is 0. In another particularly preferred embodiment, $R^7$ is hydrogen and o is 1. In another particularly preferred embodiment, $R^7$ is hydrogen and o is 2. In another particularly preferred embodiment, $R^7$ is hydrogen and o is 3.

A precursor of a thiol group is herein defined as a —[C($R^7$)$_2$]$_o$SC(O)CH$_3$ group, wherein $R^7$ and o, as well as their preferred embodiments, are as defined above for a thiol group. In a particularly preferred embodiment, $R^7$ is hydrogen and o is 0. In another particularly preferred embodiment, $R^7$ is hydrogen and o is 1. In another particularly preferred embodiment, $R^7$ is hydrogen and o is 2. In another particularly preferred embodiment, $R^7$ is hydrogen and o is 3. Most preferably, said thiol-precursor is —CH$_2$CH$_2$CH$_2$SC(O)CH$_3$, —CH$_2$CH$_2$SC(O)CH$_3$, —CH$_2$SC(O)CH$_3$ or —SC(O)CH$_3$, preferably —SC(O)CH$_3$. In the process for the preparation of a modified glycoprotein according to the invention, a sugar derivative Su(A)$_x$ wherein A is a precursor of a thiol group may be used. During said process, the thiol-precursor is converted to a thiol group.

A halogen is herein defined as F, Cl, Br or I. Preferably, said halogen is Cl or Br, more preferably Cl.

A sulfonyloxy group is herein defined as a —[C($R^7$)$_2$]$_o$OS(O)$_2$R$^8$ group, wherein $R^7$ and o are as defined above for a thiol group, and $R^8$ is selected from the group consisting of C$_1$-C$_{24}$ alkyl groups, C$_6$-C$_{24}$ aryl groups, C$_7$-C$_{24}$ alkylaryl groups and C$_7$-C$_{24}$ arylalkyl groups. $R^8$ is preferably a C$_1$-C$_4$ alkyl group, a C$_6$-C$_{12}$ aryl group, a C$_7$-C$_{12}$ alkylaryl group or a C$_7$-C$_{12}$ arylalkyl group. More preferably $R^8$ is —CH$_3$, —C$_2$H$_5$, a C$_3$ linear or branched alkyl group, a C$_6$-C$_{10}$ aryl group, or a C$_7$ alkylaryl group. $R^8$ is most preferably a methyl group, an ethyl group, a phenyl group or a p-tolyl group. Preferably $R^7$ is hydrogen or a C$_1$, C$_2$, C$_3$ or C$_4$ alkyl group, more preferably $R^7$ is hydrogen or —CH$_3$. Preferably o is 0-10, more preferably 0, 1, 2, 3, 4, 5 or 6. More preferably, $R^7$ is hydrogen, —CH$_3$ or a C$_2$ alkyl group and/or o is 0, 1, 2, 3 or 4. Even more preferably $R^7$ is hydrogen and o is 1 or 2, most preferably o is 0. $R^8$ is preferably a C$_1$-C$_4$ alkyl group, a C$_7$-C$_{12}$ alkylaryl group or a C$_7$-C$_{12}$ arylalkyl group, more preferably —CH$_3$, —C$_2$H$_5$, a C$_3$ linear or branched alkyl group or a C$_7$ alkylaryl group. It is also preferred that $R^8$ is a phenyl group. Most preferably the sulfonyloxy group is a mesylate group, —OS(O)$_2$CH$_3$, a benzenesulfonate group (—OS(O)$_2$(C$_6$H$_5$)) or a tosylate group (—OS(O)$_2$(C$_6$H$_4$CH$_3$)).

A halogenated acetamido group is herein defined as an —NHC(O)[C($R^7$)$_2$]$_o$X group, wherein $R^7$ is independently selected from the group consisting of hydrogen, halogen and an (optionally substituted) C$_1$-C$_{24}$ alkyl group, X is F, Cl, Br or I, and o is 0-24. Preferably $R^7$ is hydrogen or a C$_1$, C$_2$, C$_3$ or C$_4$ alkyl group, more preferably $R^7$ is hydrogen or —CH$_3$, most preferably hydrogen. Preferably o is 0 to 10, more preferably 1, 2, 3, 4, 5 or 6, even more preferably 1, 2, 3 or 4 and most preferably o is 1. More preferably, $R^7$ is hydrogen, —CH$_3$ or a C$_2$ alkyl group and/or o is 1, 2, 3 or 4 and most preferably $R^7$ is hydrogen and o is 1. Preferably, X is Cl or Br, more preferably X is Cl. Most preferably, $R^7$ is hydrogen, X is Cl and o is 1.

A mercaptoacetamido group is herein defined as an —NHC(O)[C($R^7$)$_2$]$_o$SH group, wherein $R^7$ is independently selected from the group consisting of hydrogen, halogen and an (optionally substituted) C$_1$-C$_{24}$ alkyl group and o is 0-24. Preferably $R^7$ is hydrogen or a C$_1$, C$_2$, C$_3$ or C$_4$ alkyl group, more preferably $R^7$ is hydrogen or —CH$_3$, most preferably hydrogen. Preferably o is 0 to 10, more preferably 1, 2, 3, 4, 5 or 6, even more preferably 1, 2, 3 or 4 and most preferably o is 2, 3 or 4. More preferably, $R^7$ is hydrogen, —CH$_3$ or a C$_2$ alkyl group and/or o is 1, 2, 3 or 4. More preferably, $R^7$ is hydrogen and o is 1, 2, 3 or 4. Most preferably, $R^7$ is hydrogen and o is 1, 2 or 3, preferably 1. Preferred examples include a mercaptoethanoylamido group, a mercaptopropanoylamido group, a mercaptobutanoylamido group and a mercapto-pentanoylamido group, preferably a mercaptopropanoylamido group.

A sulfonylated hydroxyacetamido group is herein defined as a —NHC(O)[C($R^7$)$_2$]$_o$OS(O)$_2$R$^8$ group, wherein $R^7$ is independently selected from the group consisting of hydrogen, halogen and an (optionally substituted) C$_1$-C$_{24}$ alkyl group, $R^8$ is selected from the group consisting of C$_1$-C$_{24}$ alkyl groups, C$_6$-C$_{24}$ aryl groups, C$_7$-C$_{24}$ alkylaryl groups and C$_7$-C$_{24}$ arylalkyl groups, and o is 0-24. $R^8$ is preferably a C$_1$-C$_4$ alkyl group, a C$_6$-C$_{12}$ aryl group, a C$_7$-C$_{12}$ alkylaryl group or a C$_7$-C$_{12}$ arylalkyl group, more preferably —CH$_3$, —C$_2$H$_5$, a C$_3$ linear or branched alkyl group or a C$_7$ alkylaryl group. Most preferably the sulfonyloxy group is a mesylate group —OS(O)$_2$CH$_3$, a benzenesulfonate group —OS(O)$_2$(C$_6$H$_5$) or a tosylate group —OS(O)$_2$(C$_6$H$_4$CH$_3$). Preferably $R^7$ is hydrogen or a C$_1$, C$_2$, C$_3$ or C$_4$ alkyl group, more preferably $R^7$ is hydrogen or —CH$_3$, most preferably hydrogen. Preferably o is 0 to 10, more preferably 1, 2, 3, 4, 5 or 6, even more preferably 1, 2, 3 or 4 and most preferably o is 1. More preferably, $R^7$ is hydrogen, —CH$_3$ or a C$_2$ alkyl group and/or o is 1, 2, 3 or 4. Even more preferably $R^7$ is hydrogen and o is 1, 2 or 3. Yet even more preferably, R7 is H, o is 1 and R8 is a mesylate group, a benzenesulfonate group or a tosylate group. Most preferably, $R^7$ is hydrogen, $R^8$ is —CH$_3$ and o is 1.

The sugar derivative Su(A)$_x$ may comprise one or more functional groups A. When Su(A)$_x$ comprises two or more functional groups A, each functional group A is independently selected, i.e. one Su(A)$_x$ may comprise different functional groups, e.g. an azido group and a keto group, etc. In a preferred embodiment, x is 1 or 2, more preferably x is 1. In another preferred embodiment, functional group A is an azido group or a keto group, more preferably an azido group. In another preferred embodiment, functional group A is a thiol or a halogen, more preferably a halogen.

Sugar derivative Su(A)$_x$ is derived from a sugar or a sugar derivative Su, e.g. an amino sugar or an otherwise derivatized sugar. Examples of sugars and sugar derivatives include galactose (Gal), mannose (Man), glucose (Glc), N-acetylneuraminic acid or sialic acid (Sial) and fucose (Fuc).

An amino sugar is a sugar wherein a hydroxyl (OH) group is replaced by an amine group and examples include glucosamine (GlcNH$_2$) and galactosamine (GalNH$_2$). Examples of an otherwise derivatized sugar include N-acetylneuraminic acid (sialic acid, Sia or NeuNAc) or fucose (Fuc).

Sugar derivative Su(A)$_x$ is preferably derived from galactose (Gal), mannose (Man), N-acetylglucosamine (GlcNAc), glucose (Glc), N-acetylgalactosamine (GalNAc), fucose (Fuc) and N-acetylneuraminic acid (sialic acid Sia or NeuNAc), preferably from the group consisting of GlcNAc, Glc, Gal and GalNAc. More preferably Su(A)$_x$ is derived from Gal or GalNAc, and most preferably Su(A)$_x$ is derived from GalNAc.

The one or more functional groups A in Su(A)$_x$ may be linked to the sugar or sugar derivative Su in several ways. The one or more functional groups A may be bonded to C2, C3, C4 and/or C6 of the sugar or sugar derivative, instead of a hydroxyl (OH) group. It should be noted that, since fucose lacks an OH-group on C6, if A is bonded to C6 of Fuc, then A takes the place of an H-atom.

Preferably, the one or more functional groups A in Su(A)$_x$ may be present on C2 and/or C6 of the sugar or sugar derivative Su. When a functional group A is present instead of an OH-group on C2 of a sugar or sugar derivative, A is preferably selected from the group consisting of an azido group, a halogenated acetamido group, a mercaptoacetamido group and a sulfonylated hydroxyacetamido group. However, when A is present on C2 of a 2-aminosugar derivative, e.g. GalNAc or GlcNAc, A is preferably selected from the group consisting of an azido group, a halogen, a thiol group or a derivative thereof and a sulfonyloxy group, preferably an azido group, a halogen, a thiol group and a sulfonyloxy group.

When A is an azido group, it is preferred that A is bonded to C2, C3, C4 or C6. As was described above, the one or more azide substituents in Su(A)$_x$ may be bonded to C2, C3, C4 or C6 of the sugar or sugar derivative S, instead of a hydroxyl (OH) group or, in case of 6-azidofucose (6-AzFuc), instead of a hydrogen atom. Alternatively or additionally, the N-acetyl substituent of an amino sugar derivative may be substituted by an azidoacetyl substituent. In a preferred embodiment Su(A)$_x$ is selected from the group consisting of 2-azidoacetamidogalactose (GalNAz), 6-azido-6-deoxygalactose (6-AzGal), 6-azido-6-deoxy-2-acetamidogalactose (6-AzGalNAc), 4-azido-4-deoxy-2-acetamidogalactose (4-AzGalNAc), 6-azido-6-deoxy-2-azidoacetamidogalactose (6-AzGalNAz), 2-azidoacetamidoglucose (GlcNAz), 6-azido-6-deoxyglucose (6-AzGlc), 6-azido-6-deoxy-2-acetamidoglucose (6-AzGlcNAc), 4-azido-4-deoxy-2-acetamidoglucose (4-AzGlcNAc) and 6-azido-6-deoxy-2-azidoacetamidoglucose (6-AzGlcNAz), more preferably from the group consisting of GalNAz, 4-AzGalNAc, GlcNAz and 6-AzGlcNAc. Examples of Su(A)$_x$-P wherein A is an azido group are shown below.

When A is a keto group, it is preferred that A is bonded to C2 instead of the OH-group of S. Alternatively A may be bonded to the N-atom of an amino sugar derivative, preferably a 2-amino sugar derivative. The sugar derivative then comprises an —NC(O)R$^6$ substituent. R$^6$ is preferably a C$_2$-C$_{24}$ alkyl group, optionally substituted. More preferably, R$^6$ is an ethyl group. In a preferred embodiment Su(A)$_x$ is selected from the group consisting of 2-deoxy-(2-oxopropyl)galactose (2-ketoGal), 2-N-propionylgalactosamine (2-N-propionylGalNAc), 2-N-(4-oxopentanoyl)galactosamine (2-N-LevGal) and 2-N-butyrylgalactosamine (2-N-butyrylGalNAc), more preferably 2-ketoGalNAc and 2-N-propionylGalNAc. Examples of Su(A)$_x$-P wherein A is a keto group are shown below.

When A is an alkynyl group, preferably a terminal alkynyl group or a (hetero)cycloalkynyl group, it is preferred that said alkynyl group is present on a 2-amino sugar derivative. An example of Su(A)$_x$ wherein A is an alkynyl group is 2-(but-3-yonic acid amido)-2-deoxy-galactose. An example of Su(A)$_x$-P wherein A is an alkynyl group is shown below.

When A is a thiol group, it is preferred that said thiol group is present on the 6-position of a sugar derivative or on a 2-amino sugar derivative. An example of Su(A)$_x$ wherein A is a thiol group is 2-(mercaptoacetamido)-2-deoxy-galactose. Another example of Su(A)$_x$ wherein A is a thiol group is 6-mercapto-6-deoxy-galactose.

When A is a halogen, it is preferred that said halogen is present on the 6-position of a sugar derivative or on a 2-amino sugar derivative. An example of Su(A)$_x$ wherein A is a halogen is 2-(chloroacetamido)-2-deoxy-galactose. Another example of Su(A)$_x$ wherein A is a halogen is 6-iodo-6-deoxy-galactose. Another example of Su(A)$_x$ wherein A is a halogen is 6-(chloroacetamido)-6-deoxy-galactose.

When A is a sulfonyloxy group, it is preferred that said sulfonyloxy group is present on the 6-position of a sugar derivative or on a 2-amino sugar derivative. An example of Su(A)$_x$ wherein A is a sulfonyloxy group is 2-(methylsulfonyloxyacetamido)-2-deoxy-galactose (2-GalNAcOMs). Another example of Su(A)$_x$ wherein A is a sulfonyloxy group is 2-(benzenesulfonyloxyacetamido)-2-deoxy-galactose (2-GalNAcOMs). Another example of Su(A)$_x$ wherein A is a sulfonyloxy group is 6-(methyl sulfonyl)-galactose.

When A is a halogenated acetamido group, a mercaptoacetamido group and a sulfonylated hydroxyacetamido group it is preferred that said groups are present on the 6-position of a sugar derivative.

P is herein defined as a nucleotide. P is preferably selected from the group consisting of a nucleoside monophosphate and a nucleoside diphosphate, more preferably from the group consisting of uridine diphosphate (UDP), guanosine diphosphate (GDP), thymidine diphosphate (TDP), cytidine diphosphate (CDP) and cytidine monophosphate (CMP), more preferably from the group consisting of uridine diphosphate (UDP), guanosine diphosphate (GDP), cytidine diphosphate and (CDP). Most preferably, P is UDP.

Several compounds of the formula Su(A)$_x$-P, wherein a nucleoside monophosphate or a nucleoside diphosphate P is linked to a sugar derivative Su(A)$_x$, are known in the art. For example Wang et al., *Chem. Eur. 1* 2010, 16, 13343-13345, Piller et al., *ACS Chem. Biol.* 2012, 7, 753, Piller et al., *Bioorg. Med. Chem. Lett.* 2005, 15, 5459-5462 and WO 2009/102820, all incorporated by reference herein, disclose a number of compounds Su(A)$_x$-P and their syntheses.

Figure 5:
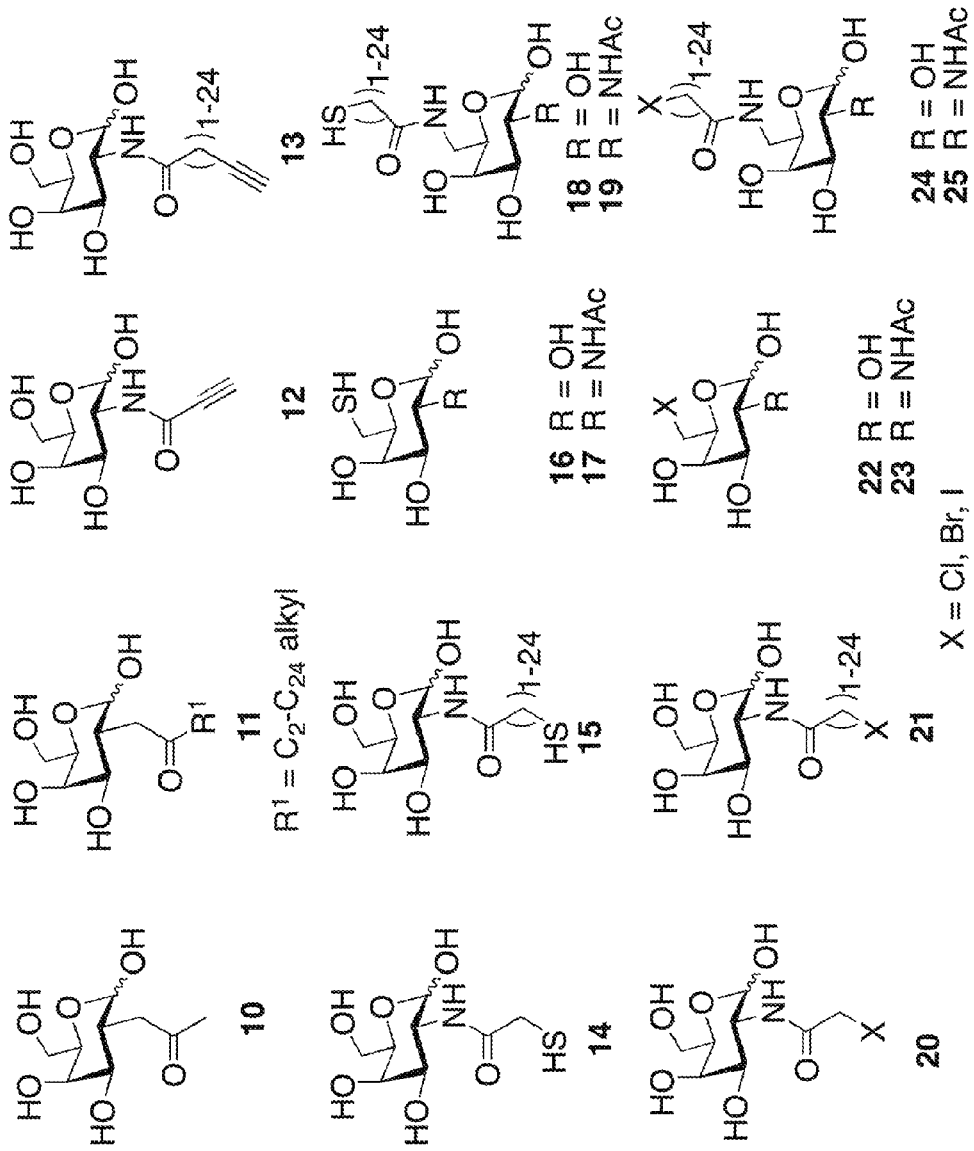
FIG. 5 shows the structures of other galactose derivatives (10-25) for transfer onto a GlcNAc-terminated sugar under the action of a galactosyl transferase (or a mutant thereof).

Several examples of azido-, keto-, alkynyl-, halogen, thiol, thiolated acetamid- and halogenated acetamido-substituted sugars and sugar derivatives (7-25) are shown in FIGS. 4 and 5, all of which may be converted into their corresponding UDP sugars Su(A)$_x$-UDP (7b-25b).

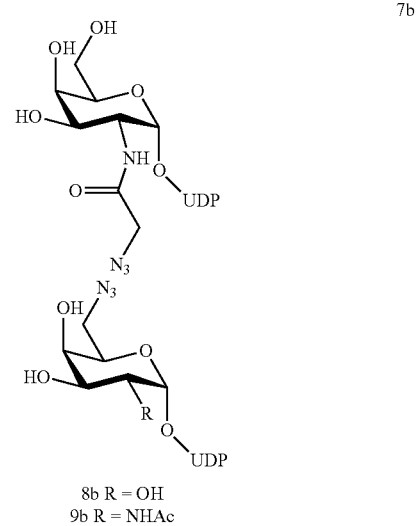

8b R = OH
9b R = NHAc

-continued
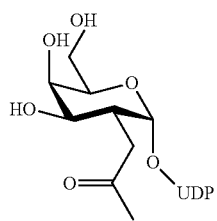
10b
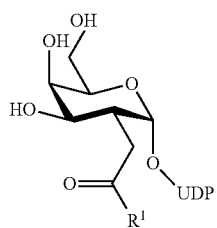
11b
$R^1 = C_2-C_{24}$ alkyl
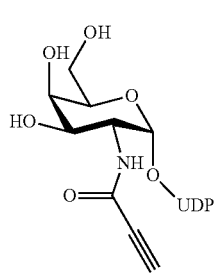
12b
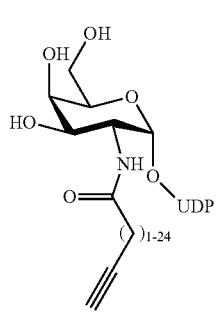
13b
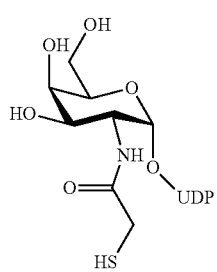
14b
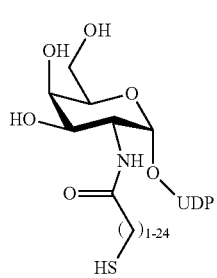
15b
-continued
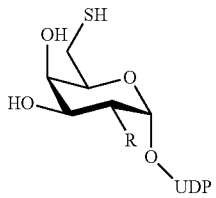
16b R = OH
17b R = NHAc
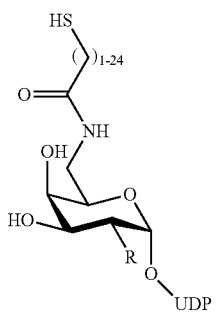
18b R = OH
19b R = NHAc
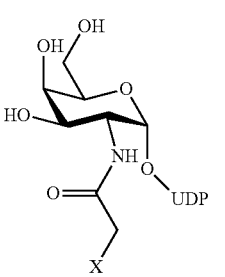
20b
X = Cl, Br, I
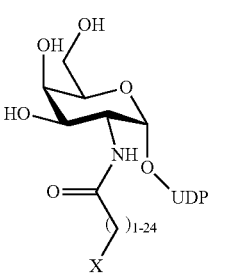
21b
X = Cl, Br, I
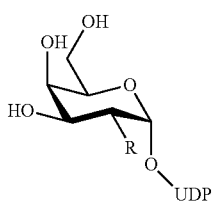
22b R = OH
23b R = NHAc
X = Cl, Br, I

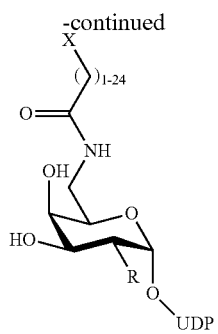

24b R = OH
25b R = NHAc
X = Cl, Br, I

Preferably, Su(A)$_x$-P is selected from the group consisting of GalNAz-UDP (7b), 6-AzGal-UDP (8b), 6-AzGalNAc-UDP (9b), 4-AzGalNAz-UDP, 6-AzGalNAz-UDP, 6-AzGlc-UDP, 6-AzGlcNAz-UDP, 2-ketoGal-UDP (10b), 2-N-propionylGalNAc-UDP (11b, wherein R$^1$ is ethyl) and 2-(but-3-yonic acid amido)-2-deoxy-galactose-UDP (13b with n=1).

Preferably, Su(A)$_x$-P is GalNAz-UDP (7b) or 6-AzGalNAc-UDP (9b). The syntheses of GalNAz-UDP (7b) and 6-AzGalNAc-UDP (9b) are disclosed in Piller et al., *Bioorg. Med. Chem. Lett.* 2005, 15, 5459-5462 and Wang et al., *Chem. Eur. J.* 2010, 16, 13343-13345, both incorporated by reference herein.

The synthesis of 2-ketoGal-UDP (10b) is disclosed in Qasba et al., *J. Am. Chem. Soc.* 2003, 125, 16162, in particular in the Supporting Information, both incorporated by reference herein.

The synthesis of 2-(but-3-yonic acid amido)-2-deoxy-galactose-UDP is disclosed in WO 2009/102820, incorporated by reference herein.

Further examples of Su(A)$_x$-P include 6-A-6-deoxygalactose-UDP (6-A-Gal-UDP), such as 6-chloro-6-deoxygalactose-UDP (6-ClGal-UDP, (22b) with X=Cl), 6-thio-6-deoxygalactose-UDP (6-HSGal-UDP, (16b)) or 2-A-2-deoxygalactose-UDP (2-A-Gal-UDP), such as 2-chloro-2-deoxygalactose-UDP (2-ClGal-UDP), 2-thio-2-deoxygalactose-UDP (2-HSGal-UDP). Alternatively, A may be indirectly substituted to the sugar derivative as part of an acetamido group that in turn is substituting a hydroxyl group. Examples include 6-A-acetamido-6-deoxygalactose-UDP (6-GalNAcA-UDP), such as 6-chloroacetamido-6-deoxygalactose-UDP (6-GalNAcCl-UDP, (24b) with 1 CH$_2$, R=OH and X=Cl), 6-thioacetamido-6-deoxygalactose-UDP (6-GalNAcSH-UDP, (18b) with 1 CH$_2$ and R=OH) or 2-A-acetamido-2-deoxygalactose-UDP (2-GalNAcA-UDP), such as 2-chloroacetamido-2-deoxygalactose-UDP (2-GalNAcCl-UDP, (20b) with X=Cl), 2-thioacetamido-2-deoxygalactose-UDP (2-GalNAcSH-UDP, (14b). Further examples include 3-thiopropanoylamido-2-deoxygalactose-UDP (2-GalNProSH-UDP) or 4-thiobutanoylamido-2-deoxygalactose-UDP (2-GalNBuSH-UDP)). Alternatively, A may be indirectly substituted to the sugar derivative as part of another functional group that in turn is substituting a hydroxyl group or is attached to a hydroxyl group. Examples of such other functional group include an (hetero)alkyl chain or a (hetero)aryl chain.

Additional examples of Su(A)$_x$ wherein Su is galactose are shown in FIGS. 4 and 5. FIG. 4 shows the structures of azido-modified galactose derivatives (7-9), for which the corresponding UDP sugar may be used for transfer onto a GlcNAc-terminated sugar under the action of a galactosyl transferase (or a mutant thereof). FIG. 5 shows the structures of other galactose derivatives (10-25), for which the corresponding UDP sugar may be used for transfer onto a GlcNAc-terminated sugar under the action of a galactosyl transferase (or a mutant thereof).

Preferably, Su(A)$_x$-P is selected from the group consisting of GalNAz-UDP (7b), 6-AzGalNAc-UDP (9b), 6-GalNAcCl-UDP ((24b) with 1 CH$_2$, R=OH and X=Cl), 6-GalNAcSH-UDP ((18b) with 1 CH$_2$ and R=OH), 2-GalNAcCl-UDP ((20b) with X=Cl), 2-GalNAcSH-UDP (14b), 6-ClGal-UDP (22b) with X=Cl), 2-ClGal-UDP, 2-HSGal-UDP and 6-HSGal-UDP (16b). Another preferred sugar derivative Su(A)$_x$-P is (15b), wherein o is 1, 2 or 3. Additional preferred sugar derivatives Su(A)$_x$-P are 2-GalNProSH-UDP and 2-GalNBuSH-UDP.

More preferably, Su(A)$_x$-P is selected from the group consisting of GalNAz-UDP (7b), 6-AzGalNAc-UDP (9b), 6-GalNAcCl-UDP ((24b) with 1 CH$_2$, R=OH and X=Cl), 6-GalNAcSH-UDP ((18b) with 1 CH$_2$ and R=OH), 2-GalNAcCl-UDP ((20b) with X=Cl), 2-GalNAcSH-UDP (14b), 6-ClGal-UDP (22b) with X=Cl) and 2-ClGal-UDP, or Su(A)$_x$-P is selected from the group consisting of 2-GalNProSH-UDP and 2-GalNBuSH-UDP.

Most preferably, Su(A)$_x$-P is selected from the group consisting of GalNAz-UDP (7b), 2-GalNAcCl-UDP ((20b) with X=Cl), or from the group consisting of 2-GalNAcSH-UDP (14b) and 2-GalNProSH-UDP and 2-GalNBuSH-UDP.

As described above, several of the sugar derivative nucleotides Su(A)$_x$-P that may be employed in the process for the preparation of a modified glycoprotein according to the invention are a substrate for a wild type galactosyltransferase. For these sugar derivative nucleotides Su(A)$_x$-P, the process according to the invention may be performed in the presence of a wild type galactosyltransferase, preferably a wild type β(1,4)-galactosyltransferase, more preferably a β(1,4)-galactosyltransferase I, as a catalyst.

When a wild type galactosyltransferase is used as a catalyst, it is preferred that Su(A)$_x$-P is selected from the group consisting of Su(A)$_x$-P wherein x is 1 and wherein A is present on C2 or C6, preferably C6, of the sugar derivative, and wherein A is selected from the group consisting of an azido group, a keto group, an alkynyl group, a thiol group or a precursor thereof, a halogen, a sulfonyloxy group, a halogenated acetamido group, a mercaptoacetamido group and a sulfonylated hydroxyacetamido group. A may be directly substituted to the sugar derivative instead of an hydroxyl group. Examples include 6-A-6-deoxygalactose-UDP (6-A-Gal-UDP), such as 6-azido-6-deoxygalactose-UDP (6-AzGal-UDP), 6-chloro-6-deoxygalactose-UDP (6-ClGal-UDP), 6-thio-6-deoxygalactose-UDP (6-HSGal-UDP) or 2-A-2-deoxygalactose-UDP (2-A-Gal-UDP), such as 2-azido-2-deoxygalactose-UDP (2-AzGal-UDP), 2-chloro-2-deoxygalactose-UDP (2-ClGal-UDP), 2-thio-2-deoxygalactose-UDP (2-HSGal-UDP). Alternatively, A may be indirectly substituted to the sugar derivative as part of an acetamido group that in turn is substituting a hydroxyl group. Examples include 6-A-acetamido-6-deoxygalactose-UDP (6-GalNAcA-UDP), such as 6-azidoacetamido-6-deoxygalactose-UDP (6-GalNAcN$_3$-UDP), 6-chloroacetamido-6-deoxygalactose-UDP (6-GalNAcCl-UDP), 6-thioacetamido-6-deoxygalactose-UDP (6-GalNAcSH-UDP) or 2-A-acetamido-2-deoxygalactose-UDP (2-GalNAcA-UDP), such as 2-azidoacetamido-2-deoxygalactose-UDP (2-GalNAcN$_3$-UDP), 2-chloroacetamido-2- deoxygalactose-UDP (2-GalNAcCl-UDP), 2-thioacetamido-2-deoxygalactose-UDP (2-GalNAcSH-UDP). Further examples include 3-thiopropanoylamido-2-deoxygalactose-UDP (2-GalNProSH-UDP) and 4-thiobutanoylamido-2-deoxygalactose-UDP (2-GalNBuSH-UDP). Alternatively, A may be indirectly substituted to the sugar derivative as part of another functional group that in turn is substituting a hydroxyl group or is attached to a hydroxyl group. Examples of such other functional group include an (hetero)alkyl chain or a (hetero)aryl chain.

In a particularly preferred embodiment of the process for the preparation of a modified glycoprotein according to the invention, $Su(A)_x$-P is selected from the group consisting of GalNAz-UDP (7b), 6-AzGalNAc-UDP (9b), 2-GalNAcSH-UDP, 2-GalNProSH-UDP, 2-GalNBuSH-UDP, 2-GalNAcX-UDP, 2-GalNAcOS(O)$_2$R$^8$-UDP, 6-GalNAcSH-UDP, 6-GalNAcX-UDP and 6-GalNAcOS(O)$_2$R$^8$-UDP, and the catalyst is bovine β(1,4)-Gal-T1 comprising a mutant catalytic domain GalT (Y289L); wherein X is Cl, Br or I; and wherein R$^8$ is a methyl group, an ethyl group, a phenyl group or a p-tolyl group. In another particularly preferred embodiment of the process for the preparation of a modified glycoprotein according to the invention, $Su(A)_x$-P is selected from the group consisting of 2-GalNProSH-UDP and 2-GalNBuSH-UDP, and the catalyst is bovine β(1,4)-Gal-T1 comprising a mutant catalytic domain GalT (Y289L).

In a further preferred embodiment 2-GalNAcX-UDP is 2-GalNAcCl-UDP or 2-GalNAcBr-UDP, more preferably 2-GalNAcCl-UDP, and 6-GalNAcX-UDP is 6-GalNAcCl-UDP or 6-GalNAcBr-UDP, more preferably 6-GalNAcCl-UDP. In another preferred embodiment, R$^8$ in 2-GalNAcOS(O)$_2$R$^8$-UDP is methyl, phenyl or p-tolyl, most preferably methyl, and R$^8$ in 6-GalNAcOS(O)$_2$R$^8$-UDP is methyl, phenyl or p-tolyl, most preferably R$^8$ is methyl.

In another particularly preferred embodiment of the process for the preparation of a modified glycoprotein according to the invention, $Su(A)_x$-P is selected from the group consisting of 6-AzGalNAc-UDP (9b), 6-HSGal-UDP, 6-XGal-UDP, 6-R$^8$S(O)$_2$OGal-UDP, and the catalyst is a wild-type human GalT; wherein X is Cl, Br or I; and wherein R$^8$ is a methyl group, an ethyl group, a phenyl group or a p-tolyl group. X is more preferably Cl or Br, most preferably Cl. R$^8$ is more preferably methyl, phenyl or p-tolyl, most preferably methyl. The human GalT is preferably a human β4-Gal-T1, a human β(1,4)-Gal-T2, a human β(1,4)-Gal-T3 and a human β(1,4)-Gal-T4.

As was described above, in the process for the modification of a glycoprotein according to the invention, $Su(A)_x$-P may be any sugar derivative nucleotide that is a substrate for a suitable galactosyltransferase catalyst.

In a preferred embodiment of the process for the preparation of a modified glycoprotein, $Su(A)_x$ comprises 1 or 2 functional groups A, i.e. preferably x is 1 or 2. More preferably, x is 1. In a preferred embodiment, Su is galactose (Gal). In a further embodiment, x is 1 or 2 and Su is Gal, and most preferably, x is 1 and Su is Gal.

In a preferred embodiment, $Su(A)_x$ is selected from the group consisting of GalNAz, 6-AzGalNAc, 6-GalNAcCl, 6-GalNAcSH, 2-GalNAcCl, 2-GalNAcSH, 6-ClGal, 2-ClGal, 2-HSGal and 6-HSGal, more preferably form the group consisting of GalNAz, 6-AzGalNAc, 6-GalNAcCl, 6-GalNAcSH, 2-GalNAcCl, 2-GalNAcSH, 2-GalNProSH, 2-GalNBuSH, 6-ClGal- and 2-ClGal. In another preferred embodiment, $Su(A)_x$ is selected from the group consisting of 2-GalNProSH and 2-GalNBuSH.

In a further preferred embodiment, x is 1 and $Su(A)_x$ is selected from the group consisting of GalNAz, 6-AzGalNAc, 6-GalNAcCl, 6-GalNAcSH, 2-GalNAcCl, 2-GalNAcSH, 6-ClGal, 2-ClGal, 2-HSGal and 6-HSGal, more preferably from the group consisting of GalNAz, 6-AzGalNAc, 6-GalNAcCl, 6-GalNAcSH, 2-GalNAcCl, 2-GalNAcSH, 6-ClGal- and 2-ClGal. In another further preferred embodiment, x is 1 and $Su(A)_x$ is selected from the group consisting of 2-GalNProSH and 2-GalNBuSH.

In a preferred embodiment, A is an azide group, a thiol group or a halogen.

In a preferred embodiment wherein A is an azide group, $Su(A)_x$ is preferably selected from the group consisting of 2-azidoacetamidogalactose (GalNAz), 6-azido-6-deoxygalactose (6-AzGal), 6-azido-6-deoxy-2-acetamidogalactose (6-AzGalNAc), 4-azido-4-deoxy-2-acetamidogalactose (4-AzGalNAc), 6-azido-6-deoxy-2-azidoacetamidogalactose (6-AzGalNAz), 2-azidoacetamidoglucose (GlcNAz), 6-azido-6-deoxyglucose (6-AzGlc), 6-azido-6-deoxy-2-acetamidoglucose (6-AzGlcNAc), 4-azido-4-deoxy-2-acetamidoglucose (4-AzGlcNAc) and 6-azido-6-deoxy-2-azidoacetamidoglucose (6-AzGlcNAz).

In a further preferred embodiment $Su(A)_x$ is selected from the group consisting of GalNAz, 6-AzGal, 4-AzGalNAc, GlcNAz and 6-AzGlcNAc. More preferably, x is 1 and $Su(A)_x$ is selected from the group consisting of 2-azidoacetamidogalactose (GalNAz), 6-azido-6-deoxygalactose (6-AzGal), 6-azido-6-deoxy-2-acetamidogalactose (6-AzGalNAc), 4-azido-4-deoxy-2-acetamidogalactose (4-AzGalNAc), 6-azido-6-deoxy-2-azidoacetamidogalactose (6-AzGalNAz), 2-azidoacetamidoglucose (GlcNAz), 6-azido-6-deoxyglucose (6-AzGlc), 6-azido-6-deoxy-2-acetamidoglucose (6-AzGlcNAc), 4-azido-4-deoxy-2-acetamidoglucose (4-AzGlcNAc) and 6-azido-6-deoxy-2-azidoacetamidoglucose (6-AzGlcNAz). More preferably, x is 1 and $Su(A)_x$ is selected from the group consisting of GalNAz, 6-AzGal, 4-AzGalNAc, GlcNAz and 6-AzGlcNAc.

In a particularly preferred embodiment of the process for the modification of a modified glycoprotein according to the invention, $Su(A)_x$ is selected from the group consisting of GalNAz, 6-AzGalNAc, 2-GalNAcSH, 2-GalNAcX, 2-GalNAcOS(O)$_2$R$^8$, 6-GalNAcSH, 6-GalNAcX and 6-GalNAcOS(O)$_2$R$^8$. In another particularly preferred embodiment of the process for the modification of a modified glycoprotein according to the invention, $Su(A)_x$ is selected from the group consisting of 2-GalNProSH and 2-GalNBuSH.

In an even more preferred embodiment, x is 1 or 2 and $Su(A)_x$ is selected from the group consisting of GalNAz, 6-AzGalNAc, 2-GalNAcSH, 2-GalNAcX, 2-GalNAcOS(O)$_2$R$^8$, 6-GalNAcSH, 6-GalNAcX and 6-GalNAcOS(O)$_2$R$^8$. In another even more preferred embodiment, x is 1 or 2 and $Su(A)_x$ is selected from the group consisting of 2-GalNProSH and 2-GalNBuSH.

In a most preferred embodiment, x is 1 and $Su(A)_x$ is selected from the group consisting of GalNAz, 6-AzGalNAc, 2-GalNAcSH, 2-GalNAcX, 2-GalNAcOS(O)$_2$R$^8$, 6-GalNAcSH, 6-GalNAcX and 6-GalNAcOS(O)$_2$R$^8$. In another most preferred embodiment, x is 1 and $Su(A)_x$ is selected from the group consisting of 2-GalNProSH and 2-GalNBuSH.

The present invention generally relates to a process for the preparation of a modified glycoprotein, the process comprising:
(a) providing a glycoprotein comprising a glycan of the formula GlcNAcMan$_5$GlcNAc$_2$ wherein the core-GlcNAc residue is optionally fucosylated; followed by
(b) contacting said glycoprotein with a compound of the formula $Su(A)_x$-P in the presence of a suitable catalyst; wherein a suitable catalyst is defined as a galactosyltransferase or a galactosyltransferase comprising a mutant catalytic domain, wherefore Su(A)$_x$-P is a substrate; wherein Su(A)$_x$ is a sugar derivative comprising x functional groups A wherein x is 1, 2, 3 or 4 and wherein A is independently selected from the group consisting of an azido group, a keto group, an alkynyl group, a thiol group or a precursor thereof, a halogen, a sulfonyloxy group, a halogenated acetamido group, a mercaptoacetamido group and a sulfonylated hydroxyacetamido group; wherein P is a nucleotide; and wherein a modified glycoprotein is defined as protein comprising a glycan of the formula Su(A)$_x$GlcNAcMan$_5$GlcNAc$_2$ wherein the core-GlcNAc residue is optionally fucosylated;
wherein GlcNAcMan$_5$GlcNAc$_2$ is a glycan according to formula (101) and Su(A)$_x$GlcNAcMan$_5$GlcNAc$_2$ is a glycan according to formula (102):

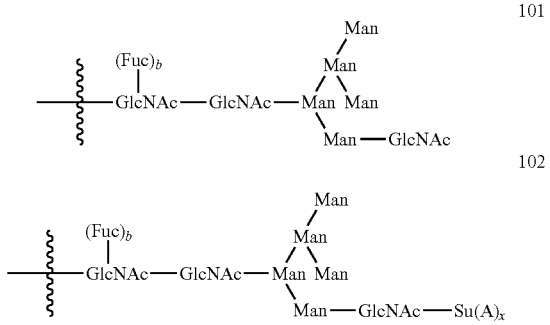

wherein b is 0 or 1 and Su(A)$_x$ is as defined above.

Step (b) of this process is described in detail above, as well as preferred embodiments thereof.

Preferably, the catalyst is selected from the group consisting of β(1,4)-galactosyltransferases, β(1,3)-N-galactosyltransferases, β(1,4)-galactosyltransferases comprising a mutant catalytic domain and β(1,3)-N-galactosyltransferases comprising a mutant catalytic domain. Consequently, in a preferred embodiment, the invention relates to a process for the preparation of a modified glycoprotein, the process comprising:
  (a) providing a glycoprotein comprising a glycan of the formula GlcNAcMan$_5$GlcNAc$_2$ wherein the core-GlcNAc residue is optionally fucosylated; followed by
  (b) contacting said glycoprotein with Su(A)$_x$-P in the presence of a catalyst selected from the group consisting of β(1,4)-galactosyltransferases, β(1,3)-N-galactosyltransferases, β(1,4)-galactosyltransferases comprising a mutant catalytic domain and β(1,3)-N-galactosyltransferases comprising a mutant catalytic domain; wherein the core GlcNAc residue of said glycan is optionally fucosylated; wherein Su(A)$_x$ is a monosaccharide sugar derivative comprising x functional groups A wherein x is 1, 2, 3 or 4 and A is independently selected from the group consisting of an azido group, a keto group, an alkynyl group, a thiol group or a precursor thereof, a halogen, a sulfonyloxy group, a halogenated acetamido group, a mercaptoacetamido group and a sulfonylated hydroxyacetamido group; wherein P is a nucleotide; wherein a modified glycoprotein is defined as a glycoprotein comprising a Su(A)$_x$GlcNAcMan$_5$GlcNAc$_2$ glycan wherein the core GlcNAc residue is optionally fucosylated; and wherein GlcNAcMan$_5$GlcNAc$_2$ is a glycan according to formula (101) and Su(A)$_x$GlcNAcMan$_5$GlcNAc$_2$ is a glycan according to formula (102) as defined above.

The glycoprotein comprising an optionally fucosylated glycan of the formula GlcNAcMan$_5$GlcNAc$_2$ may be provided in various ways.

Mammalian cells harbor extensive glycosylation machinery that is capable of producing a wide array of glycan structures in accord with the functional needs of the cell. While this complexity makes mammalian cells a poor host for the production of homogeneous glycoproteins, the capability of these cells to perform the proper post-translational modification, folding, and function of many recombinant glycoproteins necessitates their use. In fact, the manufacture of glycoprotein biologics is predominantly performed in mammalian systems, and mainly in Chinese hamster ovary (CHO) cell lines, wherein glycoform heterogeneity is monitored as a "glycan profile" that must be reliably reproduced using carefully controlled bioprocessing conditions.

All cells, including mammalian cells, have endogenous machinery for the synthesis of carbohydrates and glycoconjugates. The glycomodifying infrastructure within cells includes glycosidases, GTases, mechanisms for activated-sugar synthesis and transport, and supporting functions.

The goal of glycoengineering approaches is to simplify, control, and/or enhance glycosylation in mammalian cell lines, thereby manipulating the biosynthetic power of cells to produce specific desired glycan structures on glycoproteins.

One way to control glycan structures in mammalian cells is to temporarily block particular glycosylation pathways using RNA interference or small-molecule inhibitors, thereby producing simplified glycan structures. Several inhibitors of early N-glycosylation steps in the endoplasmatic reticulum (ER) and Golgi are known in the art. An example of such an inhibitor is swainsonine.

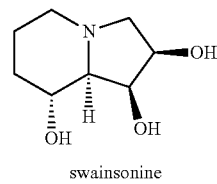 [SMILES: O[C@H]1[C@H]2[C@H](O)CCCN2C[C@H]1O]

swainsonine

Swainsonine, a plant-derived indolizidine alkaloid, is a potent inhibitor of Golgi α-mannosidase II (Msn-II, also called GMII), with a Ki of 40 nM against the Drosophila melanogaster enzyme (dGMII). Msn-II is a glycosyl hydrolase that resides in the Golgi apparatus of eukaryotes. Msn-II plays a key role in the N-linked glycosylation of proteins. It catalyzes the removal of two different mannosyl linkages of GlcNAcMan$_5$GlcNAc$_2$, which is the committed step in complex N-glycan synthesis, as is illustrated in Scheme 2 (GlcNAcMan$_5$GlcNAc$_2$ is also referred to as GnM$_5$).

Scheme 2

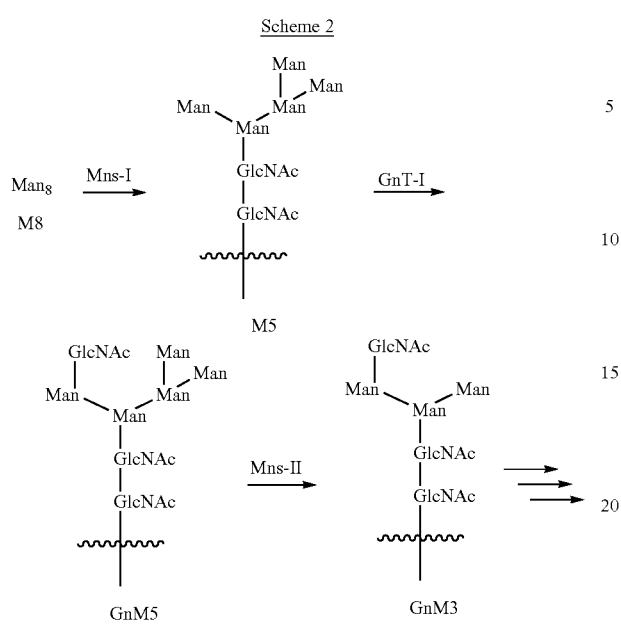

Inhibition of Msn-II during the expression of a particular glycoprotein in a host organism such as HEK293 (Human Embryonic Kidney 293 cells) or CHO-cells therefore leads to the clean production of a glycoprotein consisting of only the fucosylated $GnM_5$-type and the fucosylated $Gal-GnM_5$-type, as disclosed in Kanda et al., *Glycobiology* 2006, 17, 104-118 (incorporated by reference herein) for production of rituximab in Lec13 cell line in the presence of L-fucose (because Lec13 is lacking the ability to synthesize UDP-fucose) and swainsonine.

An alternative approach to nihilate the bioprocessing of $GnM_5$ into $GnM_3$ includes the genetic engineering of a host organism. For example, Lec1 CHO is a knock-out CHO cell-line lacking the gene for expression of Mns-II. As a consequence, biosynthesis of the N-glycan inevitable stops at the $GnM_5$-stage of the glycan, which can be isolated pure from the supernatant. A more extensive approach entails the engineering of host organisms not normally programmed to produce hybrid or complex N-glycans, such as yeast or insect cells. However, it has been amply demonstrated that these non-mammalian host cells (e.g. Glycoswitch™) can also be employed for the selective expression of a single glycoform of a particular N-glycoprotein, including glycans of the $GnM_5$-type and of the $M_5$-type.

In a preferred embodiment of the process for the preparation of a modified glycoprotein according to the invention, the glycoprotein comprising an optionally fucosylated glycan of the formula $GlcNAcMan_5GlcNAc_2$ is provided by a process comprising expression of the protein in a host organism, in the presence of swainsonine. Preferably, said host organism is a mammalian cell line, e.g. HEK293 or NS0 or a CHO-cell line.

The resulting glycoproteins may be obtained as a mixture of proteins comprising a glycan of the formula $GlcNAcMan_5GlcNAc_2$ (glycan (101), also referred to as $GnM_5$), a glycan of structure $GalGlcNAcMan_5GlcNAc_2$ (also referred to as GalGnM5), a sialiated glycan of formula $SiaGalGlcNAcMan_5GlcNAc_2$ (also referred to as SiaGalGnM5) and/or a mixture thereof.

The non-reducing sialic acid and/or galactose moiety, if present, may be removed by processing of the glycoprotein with sialidase (removal of the sialic acid moiety) and/or β-galactosidase (removal of galactose moiety), whereby a glycoprotein comprising a glycan of the formula $GlcNAcMan_5GlcNAc_2$ (101) is obtained. This process is illustrated in Scheme 3. The glycans described here are optionally fucosylated.

Scheme 3

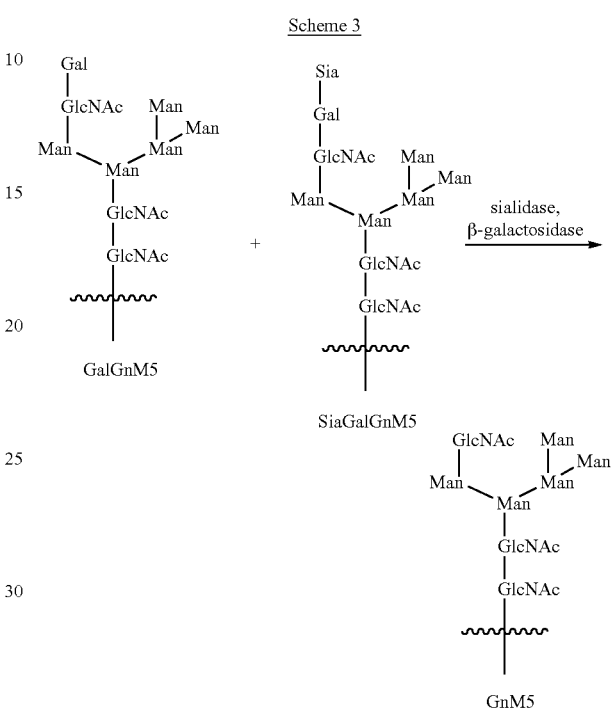

The present invention thus also relates to a process for the preparation of a modified glycoprotein, the process comprising:
(a) providing a glycoprotein comprising a glycan of the formula $GlcNAcMan_5GlcNAc_2$ wherein the core-GlcNAc residue is optionally fucosylated by a process comprising expression of said protein in a host organism in the presence of swainsonine; and
(b) contacting said glycoprotein with a compound of the formula $Su(A)_x$-P in the presence of a suitable catalyst; wherein a suitable catalyst is defined as a galactosyltransferase or a galactosyltransferase comprising a mutant catalytic domain, wherefore $Su(A)_x$-P is a substrate; wherein $Su(A)_x$ is a sugar derivative comprising x functional groups A wherein x is 1, 2, 3 or 4 and wherein A is independently selected from the group consisting of an azido group, a keto group, an alkynyl group, a thiol group or a precursor thereof, a halogen, a sulfonyloxy group, a halogenated acetamido group, a mercaptoacetamido group and a sulfonylated hydroxyacetamido group; wherein P is a nucleotide; and wherein a modified glycoprotein is defined as protein comprising a glycan of the formula $Su(A)_xGlcNAcMan_5GlcNAc_2$ wherein the core-GlcNAc residue is optionally fucosylated;
wherein $GlcNAcMan_5GlcNAc_2$ is a glycan according to formula (101) and $Su(A)_xGlcNAcMan_5GlcNAc_2$ is a glycan according to formula (102), and wherein glycans (101) and (102) are as defined above.

The present invention thus also relates to a process for the preparation of a modified glycoprotein, the process comprising:

(a) providing a glycoprotein comprising a glycan of the formula GlcNAcMan$_5$GlcNAc$_2$ wherein the core-GlcNAc residue is optionally fucosylated by a process comprising:
  (a1) expression of said protein in a host organism in the presence of swainsonine; and
  (a2) treatment of the obtained protein with sialidase and/or β-galactosidase in order to obtain a glycoprotein comprising said glycan of formula (101); and
(b) contacting said glycoprotein comprising a glycan of formula (101) with a compound of the formula Su(A)$_x$-P in the presence of a suitable catalyst; wherein a suitable catalyst is defined as a galactosyltransferase or a galactosyltransferase comprising a mutant catalytic domain, wherefore Su(A)$_x$-P is a substrate; wherein Su(A)$_x$ is a sugar derivative comprising x functional groups A wherein x is 1, 2, 3 or 4 and wherein A is independently selected from the group consisting of an azido group, a keto group, an alkynyl group, a thiol group or a precursor thereof, a halogen, a sulfonyloxy group, a halogenated acetamido group, a mercaptoacetamido group and a sulfonylated hydroxyacetamido group; wherein P is a nucleotide; and wherein a modified glycoprotein is defined as protein comprising a glycan of the formula Su(A)$_x$GlcNAcMan$_5$GlcNAc$_2$ wherein the core-GlcNAc residue is optionally fucosylated;
wherein GlcNAcMan$_5$GlcNAc$_2$ is a glycan according to formula (101) and Su(A)$_x$GlcNAcMan$_5$GlcNAc$_2$ is a glycan according to formula (102), and wherein glycans (101) and (102) are as defined above.

As described above, preferably, the catalyst in step (ii) is selected from the group consisting of β(1,4)-galactosyltransferases, β(1,3)-N-galactosyltransferases, β(1,4)-galactosyltransferases comprising a mutant catalytic domain and β(1,3)-N-galactosyltransferases comprising a mutant catalytic domain. Galactosyltransferases are described in more detail above.

Preferably, said glycoprotein is treated with sialidase and β-galactosidase in a single step (a2).

Figure 6:
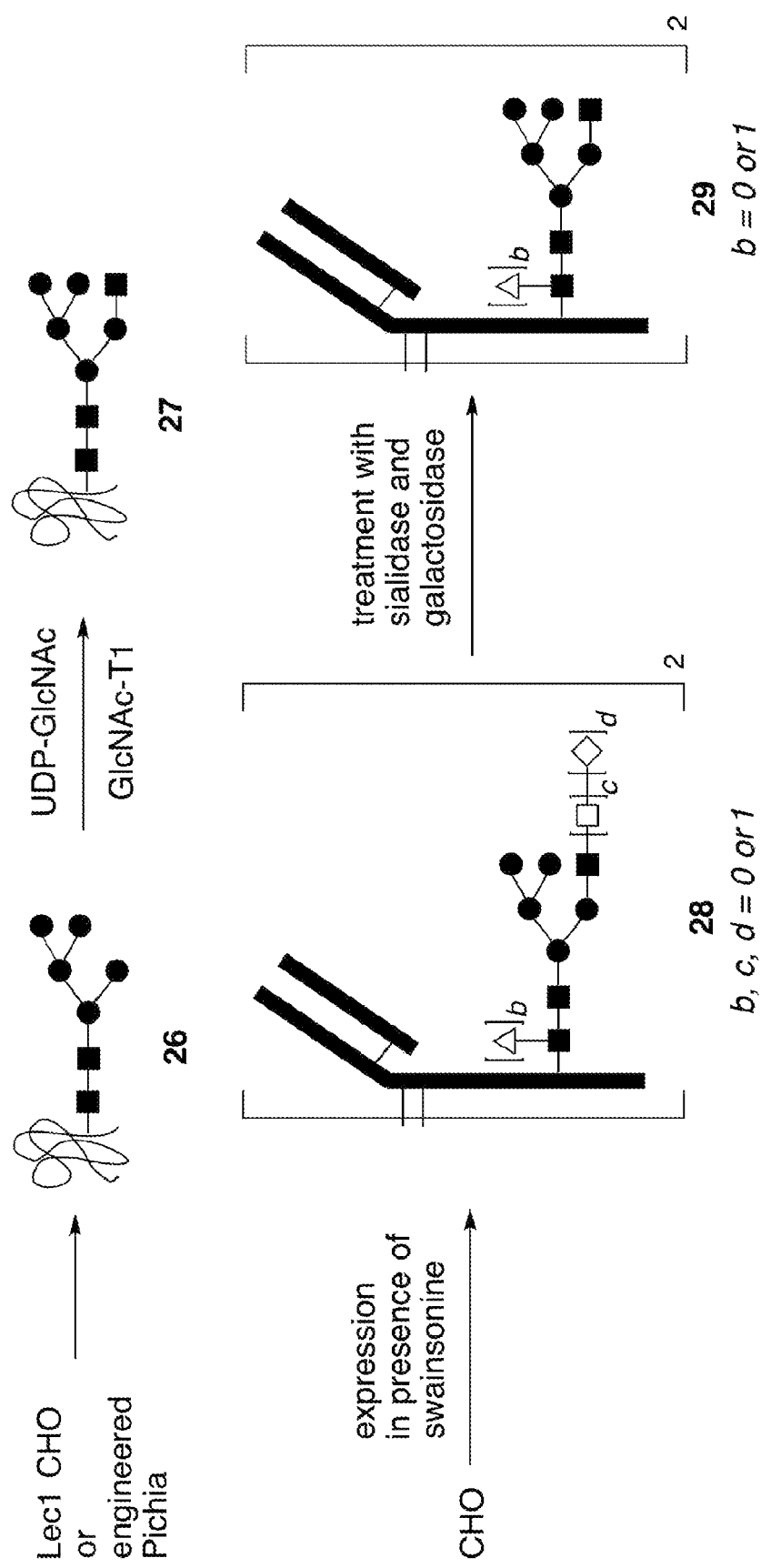
FIG. 6 shows the typical glycan structure of a protein expressed in Lec1 CHO cell-line (lacking GlcNAc-T1) or in engineered Pichia, leading to Man$_5$-protein 26, which may be converted into a GlcNAc-terminated glycan upon the action of GlcNAc-T1 and UDP-GlcNAc. Alternatively, a protein such as for example a monoclonal antibody may be expressed in a mammalian host (e.g. CHO cell) in the presence of swainsonine, giving 28, and the subsequent processing thereof under the combined action of sialidase and galactosidase leads to 29. In both cases a GlcNAc-Man$_5$-glycoprotein is obtained.

In a preferred embodiment, said glycoprotein is an antibody, and a preferred embodiment of the process for the preparation of a modified antibody is shown in FIG. 6. FIG. 6 shows a preferred embodiment for the process for the preparation of a modified glycoprotein according to the invention, wherein the glycoprotein is an antibody. A protein comprising a glycan according to formula (26) is provided by expression of the protein in a Lec1 CHO cell line, or in an engineered Pichia cell line as described below. Treatment of protein 26 with UDP-GlcNAc in the presence of β-1,4-GlcNAc-transferase leads to a protein comprising the glycan of formula (27). An antibody comprising a glycan according to formula (28) is provided by expression of the antibody in the methods described for the glycoprotein or in a CHO cell line in the presence of swainsonine. Treatment of the resulting antibody with sialidase and/or β-galactosidase provides an antibody comprising said glycan of formula (29).

In another embodiment, the glycoprotein comprising an optionally fucosylated glycan of the formula GlcNAcMan$_5$GlcNAc$_2$ is provided by expression in other expression systems than mammalian cells, which are engineered to provide alternative glycosylation patterns. Examples of such engineered systems include insect cells, yeast cells or bacterial cells. In all eukaryotes, N-linked glycosylation leads to the formation of an oligosaccharide unit Man$_8$GlcNAc$_2$. In humans, however, this core is trimmed down mainly to Man$_{5-6}$GlcNAc$_2$ (high mannose type), whereas the typical outer chain of *P. pastoris* (yeast)-secreted proteins is Man$_{8-9}$GlcNAc$_2$. This core can then be further extended (hyperglycosylated, typically with mannose) by P. pastori Golgi mannosyltransferases. To alleviate this problem, a strain was constructed that expressed an endoplasmic reticulum targeted *Trichoderma reesei* 1,2-α-D-mannosidase (FEBS Lett 2001, 503, 173, incorporated by reference). The mannosidase successfully converted the yeast-type Man$_8$GlcNAc$_2$ structures on a reporter protein to more humantype Man$_5$GlcNAc$_2$ structures, which are not substrates for hyperglycosylation in the Golgi. The Man$_5$GlcNAc$_2$ was the major N-glycan of a secreted protein, suggesting that N-glycan engineering can be effectively accomplished in *P. pastoris*. Other variants of glycosylation are also possible by further engineering of *P. pastoris*, which may yield glycoproteins GlcNAcMan$_5$GlcNAc$_2$ or Man$_3$GlcNAc$_2$ or other variants, as for example described in *Appl. Microbiol. Biotechnol.* 2010, 87, 1617 (incorporated by reference).

Modified Glycoprotein

The present invention also relates to a modified glycoprotein, obtainable by the process for the modification of a glycoprotein according to the invention. Said process for the modification of a glycoprotein, and preferred embodiments thereof, are described in more detail above.

In particular, the invention relates to a protein comprising a glycan of the formula Su(A)$_x$GlcNAcMan$_5$GlcNAc$_2$, wherein Su(A)$_x$GlcNAcMan$_5$GlcNAc$_2$ is as defined above; wherein Su(A)$_x$ is a sugar derivative comprising x functional groups A wherein x is 1, 2, 3 or 4 and A is independently selected from the group consisting of an azido group, a keto group, an alkynyl group, a thiol group, a halogen, a sulfonyloxy group, a halogenated acetamido group, a mercaptoacetamido group and a sulfonylated hydroxyacetamido group; and wherein the core GlcNAc residue of said glycan is optionally fucosylated.

As described above, when in the process for the preparation of a modified glycoprotein according the invention a functional group A is a precursor for a thiol group, said precursor is transformed into a thiol group during said process. As a consequence, when the process is performed with a sugar derivative Su(A)$_x$ comprising a precursor for a thiol group as a functional group A, a modified glycoprotein comprising a thiol group as a functional group A is obtained.

The modified glycoprotein according the invention preferably has the structure 104a, wherein Pr represents a protein, Su(A)$_x$ and b are as defined above and y is 1 to 20. The core-GlcNAc moiety is optionally fucosylated (b is 0 or 1).

In a preferred embodiment, the protein is an antibody (Pr is Ab), and thus in a preferred embodiment the glycoprotein according to the invention, i.e. the glycoprotein comprising a glycan of the formula Su(A)$_x$GlcNAcMan$_5$GlcNAc$_2$, is an antibody comprising a glycan of the formula Su(A)$_x$GlcNAcMan$_5$GlcNAc$_2$, wherein the core GlcNAc residue of said glycan is optionally fucosylated. Said antibody preferably has the structure (104b), wherein Ab represents an antibody, and Su(A)$_x$, b and y are as defined above for a protein comprising a glycan of the formula Su(A)$_x$GlcNAcMan$_5$GlcNAc$_2$.

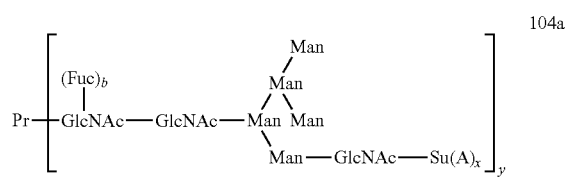

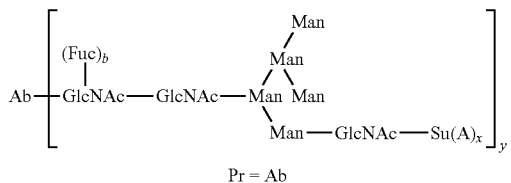

Pr = Ab

Preferably, in (104a), y is 1 to 10, more preferably y is 1, 2, 3, 4, 5, 6, 7 or 8, even more preferably y is 1, 2, 3 or 4, even more preferably y is 1 or 2, most preferably y is 1.

Preferably, in (104b), y is 1 to 10, more preferably y is 1, 2, 3, 4, 5, 6, 7 or 8. When the antibody is a whole antibody, it is preferred that y is 2, 4, 6 or 8, preferably 2 or 4, more preferably 2. When the antibody is an antibody fragment, it is preferred that y is 1 or 2, preferably 1.

In the modified glycoprotein according to the invention, A is independently selected from the group consisting of an azido group, a keto group, an alkynyl group, a thiol group, a halogen, a sulfonyloxy group, a halogenated acetamido group, a mercaptoacetamido group and a sulfonylated hydroxyacetamido group. These groups A are described in more detail above. In a further preferred embodiment, in (104a) and (104b) A is independently selected from the group consisting of an azido group, a halogen and a thiol group, and most preferably A is an azido group or a halogen group.

The sugar derivative $Su(A)_x$ in the $Su(A)_x GlcNAcMan_5 GlcNAc_2$ glycan of the modified glycoprotein or antibody may for example be bonded to C4 of the terminal GlcNAc-moiety via a β(1,4)-glycosidic bond or to C3 of said GlcNAc-moiety via an α(1,3)-glycosidic bond. The core-GlcNAc-moiety of the $Su(A)_x GlcNAcMan_5 GlcNAc_2$ glycan is bonded via C1 to the protein or antibody, preferably via an N-glycosidic bond to the amide nitrogen atom in the side chain of an asparagine amino acid of the protein or antibody. The core-GlcNAc-moiety in said $Su(A)_x GlcNAcMan_5 GlcNAc_2$ glycan is optionally fucosylated. Whether the sugar derivative $Su(A)_x$ in the $Su(A)_x GlcNAcMan_5 GlcNAc_2$ glycan of the modified glycoprotein or antibody is bonded to C4 of the terminal GlcNAc-moiety via a β(1,4)-glycosidic bond or to C3 of said terminal GlcNAc-moiety via an α(1,3)-glycosidic bond depends on the catalyst that was used in the process for the preparation of the modified glycoprotein or antibody. When the process is performed in the presence of a β(1,4)-galactosyltransferase catalyst then binding occurs via Cl of $Su(A)_x$ and C4 of the terminal GlcNAc via a β(1,4)-glycosidic bond. When the process is performed in the presence of a α(1,3)-galactosyltransferase catalyst then binding occurs via C1 of $Su(A)_x$ and C3 of the terminal GlcNAc via an α(1,3)-glycosidic bond.

When A is an azido functional group, the modified glycoprotein according to the invention is referred to as an azido-modified glycoprotein. When A is a keto functional group, the modified glycoprotein is referred to as a keto-modified glycoprotein. When A is an alkynyl functional group, the modified glycoprotein is referred to as an alkyne-modified glycoprotein. When A is a thiol group, the modified glycoprotein is referred to as a thiol-modified glycoprotein. When A is a halogen group, the modified glycoprotein is referred to as a halogen-modified protein. When A is a sulfonyloxy group, the modified glycoprotein is referred to as a sulfonyloxy-modified protein. When A is a mercaptoac-etamido group, the modified glycoprotein is referred to as a mercaptoacetamido-modified protein. When A is a halogenated acetamido group, the modified glycoprotein is referred to as a halogenated acetamido-modified protein. When A is a sulfonylated hydroxyacetamido group, the modified glycoprotein is referred to as a sulfonylated hydroxyacetamido-modified protein.

Preferably, the modified glycoprotein is an azide-, a halogen- or a thiol-modified glycoprotein, more preferably an azide- or a halogen-modified glycoprotein, even more preferably an azide- or a halogen-modified antibody. Even more preferably the modified glycoprotein is an azide-modified glycoprotein, more preferably an azide-modified antibody.

In a preferred embodiment, said $Su(A)_x$ is derived from a sugar or sugar derivative selected from the group consisting of galactose (Gal), mannose (Man), N-acetylglucosamine (GlcNAc), glucose (Glc), N-acetylgalactosamine (GalNAc), glucuronic acid (Gcu), fucose (Fuc) and N-acetylneuraminic acid (sialic acid), preferably Gal, GlcNAc, glucose and GalNAc.

In another preferred embodiment $Su(A)_x$ is selected from the group consisting of GalNAz, 6-AzGal, 6-AzGalNAc, 4-AzGalNAz, 6-AzGalNAz, 6-AzGlc, 6-AzGlcNAz, 2-ketoGal, 2-N-propionylGalNAc and 2-(but-3-yonic acid amido)-2-deoxy-galactose. Most preferably, $Su(A)_x$ is GalNAz or 4-AzGalNAc.

In a preferred embodiment, $Su(A)_x$ comprises 1 or 2 functional groups A, i.e. preferably x is 1 or 2. More preferably, x is 1. In another preferred embodiment, Su is galactose (Gal). In a further preferred embodiment, x is 1 or 2 and Su is Gal, and most preferably, x is 1 and Su is Gal.

In a preferred embodiment, $Su(A)_x$ is selected from the group consisting of GalNAz, 6-AzGalNAc, 6-GalNAcCl, 6-GalNAcSH, 2-GalNAcCl, 2-GalNAcSH, 6-ClGal, 2-Cl-Gal, 2-HSGal and 6-HSGal, more preferably form the group consisting of GalNAz, 6-AzGalNAc, 6-GalNAcCl, 6-GalNAcSH, 2-GalNAcCl, 2-GalNAcSH, 6-ClGal- and 2-ClGal. In another preferred embodiment, $Su(A)_x$ is selected from the group consisting of 2-GalNProSH and 2-GalNBuSH.

In a further preferred embodiment, x is 1 and $Su(A)_x$ is selected from the group consisting of GalNAz, 6-AzGal-NAc, 6-GalNAcCl, 6-GalNAcSH, 2-GalNAcCl, 2-Gal-NAcSH, 6-ClGal, 2-ClGal, 2-HSGal and 6-HSGal, more preferably from the group consisting of GalNAz, 6-AzGal-NAc, 6-GalNAcCl, 6-GalNAcSH, 2-GalNAcCl, 2-Gal-NAcSH, 6-ClGal- and 2-ClGal. In another further preferred embodiment, x is 1 and $Su(A)_x$ is selected from the group consisting of 2-GalNProSH and 2-GalNBuSH.

In a preferred embodiment of the modified glycoprotein according to the invention, A is an azide group, a thiol group or a halogen. The modified glycoprotein is preferably an azide-modified glycoprotein, a thiol-modified glycoprotein or a halogen-modified glycoprotein. When the glycoprotein is a halogen-modified glycoprotein, it is preferably a chloride-modified glycoprotein, a bromide-modified glycoprotein or an iodide-modified glycoprotein, more preferably a chloride-modified glycoprotein or a bromide-modified glycoprotein, and most preferably a chloride-modified glycoprotein. More preferably, x is 1 and the modified glycoprotein is preferably an azide-modified glycoprotein, a thiol-modified glycoprotein or a halogen-modified glycoprotein (preferably a chloride- or a bromide-modified glycoprotein, most preferably a chloride-modified glycoprotein).

In a preferred embodiment wherein A is an azide group, $Su(A)_x$ is preferably selected from the group consisting of 2-azidoacetamidogalactose (GalNAz), 6-azido-6-deoxygalactose (6-AzGal), 6-azido-6-deoxy-2-acetamidogalactose (6-AzGalNAc), 4-azido-4-deoxy-2-acetamidogalactose (4-AzGalNAc), 6-azido-6-deoxy-2-azidoacetamidogalactose (6-AzGalNAz), 2-azidoacetamidoglucose (GlcNAz), 6-azido-6-deoxyglucose (6-AzGlc), 6-azido-6-deoxy-2-acetamidoglucose (6-AzGlcNAc), 4-azido-4-deoxy-2-acetamidoglucose (4-AzGlcNAc) and 6-azido-6-deoxy-2-azidoacetamidoglucose (6-AzGlcNAz). In a further preferred embodiment $Su(A)_x$ is selected from the group consisting of GalNAz, 6-AzGal, 4-AzGalNAc, GlcNAz and 6-AzGlcNAc. More preferably, x is 1 and $Su(A)_x$ is selected from the group consisting of 2-azidoacetamidogalactose (GalNAz), 6-azido-6-deoxygalactose (6-AzGal), 6-azido-6-deoxy-2-acetamidogalactose (6-AzGalNAc), 4-azido-4-deoxy-2-acetamidogalactose (4-AzGalNAc), 6-azido-6-deoxy-2-azidoacetamidogalactose (6-AzGalNAz), 2-azidoacetamidoglucose (GlcNAz), 6-azido-6-deoxyglucose (6-AzGlc), 6-azido-6-deoxy-2-acetamidoglucose (6-AzGlcNAc), 4-azido-4-deoxy-2-acetamidoglucose (4-AzGlcNAc) and 6-azido-6-deoxy-2-azidoacetamidoglucose (6-AzGlcNAz). More preferably, x is 1 and $Su(A)_x$ is selected from the group consisting of GalNAz, 6-AzGal, 4-AzGalNAc, GlcNAz and 6-AzGlcNAc.

In a particularly preferred embodiment of the modified glycoprotein according to the invention, $Su(A)_x$ is selected from the group consisting of GalNAz, 6-AzGalNAc, 2-GalNAcSH, 2-GalNAcX, 2-GalNAcOS(O)$_2$R$^8$, 6-GalNAcSH, 6-GalNAcX and 6-GalNAcOS(O)$_2$R$^8$. In another particularly preferred embodiment of the modified glycoprotein according to the invention, $Su(A)_x$ is selected from the group consisting of 2-GalNProSH and 2-GalNBuSH. In an even more preferred embodiment, x is 1 or 2 and $Su(A)_x$ is selected from the group consisting of GalNAz, 6-AzGalNAc, 2-GalNAcSH, 2-GalNAcX, 2-GalNAcOS(O)$_2$R$^8$, 6-GalNAcSH, 6-GalNAcX and 6-GalNAcOS(O)$_2$R$^8$. In another even more preferred embodiment, x is 1 or 2 and $Su(A)_x$ is selected from the group consisting of 2-GalNProSH and 2-GalNBuSH. In a most preferred embodiment, x is 1 and $Su(A)_x$ is selected from the group consisting of GalNAz, 6-AzGalNAc, 2-GalNAcSH, 2-GalNAcX, 2-GalNAcOS(O)$_2$R$^8$, 6-GalNAcSH, 6-GalNAcX and 6-GalNAcOS(O)$_2$R$^8$. In another most preferred embodiment, x is 1 and $Su(A)_x$ is selected from the group consisting of 2-GalNProSH and 2-GalNBuSH. R$^8$, and preferred embodiments thereof, are as defined above.

The process for conversion of a glycoprotein containing a terminal GlcNAc is graphically depicted in FIG. 7, where it is shown that either glycoprotein 27 or glycosylated monoclonal antibody 29 can be converted into azidomodified glycoprotein 30 or antibody 31, respectively.

In a preferred embodiment, the modified glycoprotein according to the invention is an azide-modified glycoprotein, i.e. a functional group A in $Su(A)_x$ is an azido group. An azide-modified glycoprotein may have the structure (111) shown below, wherein $Su(A)_x$, with A is azido, is depicted as $Su[(Q)_p\text{-}N_3]x$:

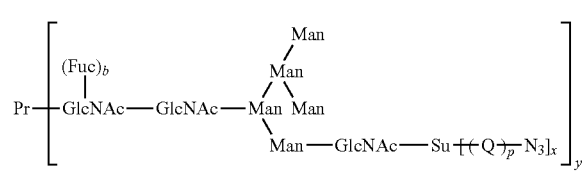

111 wherein:
Pr is protein;
b is 0 or 1;
x is 1, 2, 3 or 4;
Su is a sugar derivative;
p is 0 or 1;
Q is —N(H)C(O)CH$_2$— or —CH$_2$—;
y is 1-20;

The azide-modified glycoprotein may comprise 1 to 20 optionally fucosylated glycans (2), i.e. y is 1 to 20. Preferably, y is 1 to 10, more preferably y is 1, 2, 3, 4, 5, 6, 7 or 8, even more preferably y is 1, 2, 3 or 4 and most preferably y is 1 or 2.

Each sugar derivative may comprise 1 to 4 independently selected groups A (x is 1, 2, 3 or 4). Preferably, x is 1 or 2, and more preferably x is 1.

In a preferred embodiment, y is 1, 2, 3 or 4 and x is 1 or 2. More preferably, y is 1 or 2 and x is 1 or 2. Even more preferably, y is 1 or 2 and x is 1. When the glycoprotein is an antibody, it is preferred that y is 2, 4, 6 or 8 and x is 1 or 2. More preferably, y is 2 or 4 and x is 1 or 2. More preferably, y is 2 and x is 1.

The value of p and the nature of Q depend on the azide-substituted sugar derivative $Su(A)_x$ that is present in the azide-modified glycoprotein. If an azido group in $Su(A)_x$ is present on the C2, C3, or C4 position of the sugar or the sugar derivative, i.e. instead of the sugar-OH-group, then p is 0. If an azido group in $Su(A)_x$ is a 2-azidoacetamido group, i.e. $Su(A)_x$ is e.g. GalNAz or GlcNAz, then p is 1 and Q is —N(H)C(O)CH$_2$—. If an azido group in $Su(A)_x$ is present on the C6 position of the sugar or the sugar derivative, i.e. instead of a sugar-OH-group or, in case of 6-AzFuc, instead of a H-atom, then p is 1 and Q is —CH$_2$—.

Preferably the modified glycoprotein according to the invention is an N-glycoprotein containing a defined and limited number (1-4) of N-glycosylation sites. More preferably the modified glycoprotein according to the invention is a modified antibody (Pr is Ab), more preferably a monoclonal antibody, even more preferably selected from the group consisting of IgA, IgD, IgE, IgG and IgM antibodies, most preferably said antibody is an IgG antibody. When the modified antibody is a whole antibody, the antibody preferably comprises two or more, more preferably two, $Su(A)_x$GlcNAcMan$_5$GlcNAc$_2$ glycans (102), said glycans (102) being optionally fucosylated. In other words, in this case y is preferably 2 or more, more preferably y is 2, 4, 6 or 8, even more preferably y is 2 or 4 and more preferably y is 2. However, if the modified antibody is an antibody fragment, e.g. a Fab or Fc fragment, the antibody may have one or more, and more preferably one $Su(A)_x$GlcNAcMan$_5$GlcNAc$_2$glycan (102), which is optionally fucosylated. In this case, y is preferably 1 or more, more preferably y is 1 or 2, and most preferably, y is 1.

In the modified antibody according to the invention, a $Su(A)_x$GlcNAcMan$_5$GlcNAc$_2$ glycan may be situated anywhere on the antibody, provided that said substituent does not hinder the binding of an antigen the antigen-binding site of the antibody. In one embodiment, said $Su(A)_x$GlcNAcMan$_5$GlcNAc$_2$ glycan is situated in the Fc domain of the antibody, more preferably in the $C_H2$ domain. In another embodiment, said $Su(A)_x$GlcNAcMan$_5$GlcNAc$_2$ glycan is situated on the Fab domain of the antibody. In another embodiment, said $Su(A)_x$GlcNAcMan$_5$GlcNAc$_2$ glycan is situated on an antibody Fab or Fc fragment.

As was described above, the process for the preparation of the modified antibody may provide modified antibodies comprising more than one $Su(A)_x$GlcNAcMan$_5$GlcNAc$_2$ glycan. The number of substituents on the antibodies depends not only on the nature of the antibody to be modified (e.g. whole antibody, single chain, fragment, etc.) but also on the number of GlcNAcMan$_5$GlcNAc$_2$ glycans that is present on the antibody to be modified.

Process for the Preparation of a Protein-Conjugate

The present invention also relates to the use of a modified glycoprotein according to the invention in the preparation of a protein-conjugate. A protein-conjugate is herein defined as a protein that is conjugated to a molecule of interest (D) via a linker (L). The protein-conjugate according to the invention may be conjugated to one or to more than one molecule of interest (D) via said linker (L).

The invention also relates to the use of a modified antibody according to the invention in the preparation of an antibody-conjugate, wherein an antibody-conjugate is defined as an antibody that is conjugated to a molecule of interest (D) via a linker (L).

A molecule of interest may for example be a reporter molecule, a diagnostic compound, an active substance, an enzyme, an amino acid (including an unnatural amino acid), a (non-catalytic) protein, a peptide, a polypeptide, an oligonucleotide, a glycan, a (poly)ethylene glycol diamine (e.g. 1,8-diamino-3,6-dioxaoctane or equivalents comprising longer ethylene glycol chains), a polyethylene glycol chain, a polyethylene oxide chain, a polypropylene glycol chain, a polypropylene oxide chain, 1,x-diaminoalkane (wherein x is the number of carbon atoms in the alkane), an azide or a (hetero)cycloalkynyl moiety, preferably a bivalent or bifunctional (hetero)cycloalkynyl moiety. In a preferred embodiment, the molecule of interest is selected from the group consisting of an amino acid (in particular lysine), an active substance, a reporter molecule, an azide and a (hetero)cycloalkynyl moiety.

An active substance is a pharmacological and/or biological substance, i.e. a substance that is biologically and/or pharmaceutically active, for example a drug or a prodrug, a diagnostic agent, an amino acid, a protein, a peptide, a polypeptide, a glycan, a lipid, a vitamin, a steroid, a nucleotide, a nucleoside, a polynucleotide, RNA or DNA. Examples of suitable peptide tags include cell-penetrating peptides like human lactoferrin or polyarginine. An example of a suitable glycan is oligomannose.

In a preferred embodiment, the active substance is selected from the group consisting of drugs and prodrugs. More preferably, the active substance is selected from the group consisting of pharmaceutically active compounds, in particular low to medium molecular weight compounds (e.g. about 200 to about 1500 Da, preferably about 300 to about 1000 Da), such as for example cytotoxins, antiviral agents, antibacterial agents, peptides and oligonucleotides. Examples of cytotoxins include colchicine, vinca alkaloids, camptothecins, doxorubicin, daunorubicin, taxanes, calicheamycins, tubulysins, irinotecans, an inhibitory peptide, amanitin, deBouganin, duocarmycins, maytansines, auristatins or pyrrolobenzodiazepines (PBDs), preferably camptothecins, doxorubicin, daunorubicin, taxanes, calicheamycins, duocarmycins, maytansines, auristatins or pyrrolobenzodiazepines (PBDs). In a preferred embodiment, the cytotoxin is selected from the group consisting of camptothecins, doxorubicin, daunorubicin, taxanes, calicheamycins, duocarmycins, maytansines, auristatins and pyrrolobenzodiazepines (PBDs). In another preferred embodiment, the cytotoxin is selected from the group consisting of colchicine, vinca alkaloids, tubulysins, irinotecans, an inhibitory peptide, amanitin and deBouganin.

A reporter molecule is a molecule whose presence is readily detected, for example a diagnostic agent, a dye, a fluorophore, a radioactive isotope label, a contrast agent, a magnetic resonance imaging agent or a mass label. Examples of a fluorophore include all kinds of Alexa Fluor (e.g. Alexa Fluor 555), cyanine dyes (e.g. Cy3 or Cy5), coumarin derivatives, fluorescein, rhodamine, allophycocyanin and chromomycin.

Examples of radioactive isotope label include $^{99m}$Tc, $^{111}$In, $^{18}$F, $^{14}$C, $^{64}$Cu, $^{131}$I or $^{123}$I, which may or may not be connected via a chelating moiety such as DTPA, DOTA, NOTA or HYNIC.

In the protein-conjugate according to the invention, the molecule of interest (D) is conjugated to the antibody via a linker (L). Linkers or linking units are well known in the art, and are described in more detail below.

The present invention also relates to a process for the preparation of a protein-conjugate, said process comprising reacting a modified glycoprotein according to the invention with a linker-conjugate, wherein said linker-conjugate comprises a functional group B and one or more molecules of interest (D), wherein said functional group B is a functional group that is capable of reacting with a functional group A of a Su(A)$_x$GlcNAcMan$_5$GlcNAc$_2$ substituent on said modified glycoprotein, and wherein Su(A)$_x$ is a sugar derivative comprising x functional groups A wherein x is 1, 2, 3 or 4 and A is independently selected from the group consisting of an azido group, a keto group, an alkynyl group, a thiol group, a halogen, a sulfonyloxy group, a halogenated acetamido group, a mercaptoacetamido group and a sulfonylated hydroxyacetamido group; wherein P is a nucleotide.

In a preferred embodiment of the process for the preparation of a glycoprotein-conjugate, Su(A)$_x$ comprises 1 or 2 functional groups A, i.e. preferably x is 1 or 2. More preferably, x is 1. In another preferred embodiment, Su is galactose (Gal). In a further preferred embodiment, x is 1 or 2 and Su is Gal, and most preferably, x is 1 and Su is Gal. In these preferred embodiments it is further preferred that the linker-conjugate comprises 1 or 2, and most preferably 1, molecules of interest.

In a preferred embodiment, Su(A)$_x$ is selected from the group consisting of GalNAz, 6-AzGalNAc, 6-GalNAcCl, 6-GalNAcSH, 2-GalNAcCl, 2-GalNAcSH, 6-ClGal, 2-ClGal, 2-HSGal and 6-HSGal, more preferably form the group consisting of GalNAz, 6-AzGalNAc, 6-GalNAcCl, 6-GalNAcSH, 2-GalNAcCl, 2-GalNAcSH, 6-ClGal- and 2-ClGal. In another preferred embodiment, Su(A)$_x$ is selected from the group consisting of 2-GalNProSH and 2-GalNBuSH. In these preferred embodiments it is further preferred that the linker-conjugate comprises 1 or 2, and most preferably 1, molecules of interest.

In a further preferred embodiment, x is 1 and Su(A)$_x$ is selected from the group consisting of GalNAz, 6-AzGalNAc, 6-GalNAcCl, 6-GalNAcSH, 2-GalNAcCl, 2-GalNAcSH, 6-ClGal, 2-ClGal, 2-HSGal and 6-HSGal, more preferably from the group consisting of GalNAz, 6-AzGalNAc, 6-GalNAcCl, 6-GalNAcSH, 2-GalNAcCl, 2-GalNAcSH, 6-ClGal- and 2-ClGal. In another further preferred embodiment, x is 1 and Su(A)$_x$ is selected from the group consisting of 2-GalNProSH and 2-GalNBuSH. In these preferred embodiments it is further preferred that the linker-conjugate comprises 1 or 2, and most preferably 1, molecules of interest.

In a preferred embodiment wherein A is an azide group, Su(A)$_x$ is preferably selected from the group consisting of 2-azidoacetamidogalactose (GalNAz), 6-azido-6-deoxygalactose (6-AzGal), 6-azido-6-deoxy-2-acetamidogalactose (6-AzGalNAc), 4-azido-4-deoxy-2-acetamidogalactose (4-AzGalNAc), 6-azido-6-deoxy-2-azidoacetamidogalactose (6-AzGalNAz), 2-azidoacetamidoglucose (GlcNAz), 6-azido-6-deoxyglucose (6-AzGlc), 6-azido-6-deoxy-2-acetamidoglucose (6-AzGlcNAc), 4-azido-4-deoxy-2-acetamidoglucose (4-AzGlcNAc) and 6-azido-6-deoxy-2-azidoacetamidoglucose (6-AzGlcNAz). In a further preferred embodiment $Su(A)_x$ is selected from the group consisting of GalNAz, 6-AzGal, 4-AzGalNAc, GlcNAz and 6-AzGlcNAc. More preferably, x is 1 and $Su(A)_x$ is selected from the group consisting of 2-azidoacetamidogalactose (GalNAz), 6-azido-6-deoxygalactose (6-AzGal), 6-azido-6-deoxy-2-acetamidogalactose (6-AzGalNAc), 4-azido-4-deoxy-2-acetamidogalactose (4-AzGalNAc), 6-azido-6-deoxy-2-azidoacetamidogalactose (6-AzGalNAz), 2-azidoacetamidoglucose (GlcNAz), 6-azido-6-deoxyglucose (6-AzGlc), 6-azido-6-deoxy-2-acetamidoglucose (6-AzGlcNAc), 4-azido-4-deoxy-2-acetamidoglucose (4-AzGlcNAc) and 6-azido-6-deoxy-2-azidoacetamidoglucose (6-AzGlcNAz). More preferably, x is 1 and $Su(A)_x$ is selected from the group consisting of GalNAz, 6-AzGal, 4-AzGalNAc, GlcNAz and 6-AzGlcNAc. In these preferred embodiments it is further preferred that the linker-conjugate comprises 1 or 2, and most preferably 1, molecules of interest.

In a particularly preferred embodiment of the modified antibody according to the invention, $Su(A)_x$ is selected from the group consisting of GalNAz, 6-AzGalNAc, 2-GalNAcSH, 2-GalNAcX, 2-GalNAcOS(O)$_2$R$^8$, 6-GalNAcSH, 6-GalNAcX and 6-GalNAcOS(O)$_2$R$^8$. In another particularly preferred embodiment of the modified antibody according to the invention, $Su(A)_x$ is selected from the group consisting of 2-GalNProSH and 2-GalNBuSH. In an even more preferred embodiment, x is 1 or 2 and $Su(A)_x$ is selected from the group consisting of GalNAz, 6-AzGalNAc, 2-GalNAcSH, 2-GalNAcX, 2-GalNAcOS(O)$_2$R$^8$, 6-GalNAcSH, 6-GalNAcX and 6-GalNAcOS(O)$_2$R$^8$. In another even more preferred embodiment, x is 1 or 2 and $Su(A)_x$ is selected from the group consisting of 2-GalNProSH and 2-GalNBuSH. In a most preferred embodiment, x is 1 and $Su(A)_x$ is selected from the group consisting of GalNAz, 6-AzGalNAc, 2-GalNAcSH, 2-GalNAcX, 2-GalNAcOS(O)$_2$R$^8$, 6-GalNAcSH, 6-GalNAcX and 6-GalNAcOS(O)$_2$R$^8$. In another most preferred embodiment, x is 1 and $Su(A)_x$ is selected from the group consisting of 2-GalNProSH and 2-GalNBuSH. In these preferred embodiments it is further preferred that the linker-conjugate comprises 1 or 2, and most preferably 1, molecules of interest.

Preferably, the modified glycoprotein that is reacted with a linker-conjugate in the process according to the invention is a modified antibody. The invention therefore also relates to a process for the preparation of an antibody-conjugate, said process comprising reacting a modified antibody according to the invention with a linker-conjugate, wherein said linker-conjugate comprises a functional group B and one or more molecules of interest (D), wherein said functional group B is a functional group that is capable of reacting with a functional group A of a $Su(A)_x$GlcNAcMan$_5$GlcNAc$_2$ substituent on said modified antibody, and wherein $Su(A)_x$ is a sugar derivative comprising x functional groups A wherein x is 1, 2, 3 or 4 and A is independently selected from the group consisting of an azido group, a keto group, an alkynyl group, a thiol group, a halogen, a sulfonyloxy group, a halogenated acetamido group, a mercaptoacetamido group and a sulfonylated hydroxyacetamido group; wherein P is a nucleotide.

The linker-conjugate preferably is of the formula B-L(D)$_r$, wherein D is as defined above, and B and L are as defined below, and r is 1-20. Preferably r is 1-10, more preferably r is 1-8, even more preferably r is 1, 2, 3, 4, 5 or 6, even more preferably r is 1, 2, 3 or 4 yet even more preferably r is 1 or 2, and most preferably r is 1.

Complementary functional groups B for the functional group A on the modified glycoprotein (A is an azido group, a keto group, an alkynyl group, a thiol group, a halogen, a sulfonyloxy group, a halogenated acetamido group, a mercaptoacetamido group and a sulfonylated hydroxyacetamido group) are known in the art.

When A is an azido group, linking of the azide-modified glycoprotein and the linker-conjugate preferably takes place via a cycloaddition reaction. Functional group B is then preferably selected from the group consisting of alkynyl groups, preferably terminal alkynyl groups, and (hetero) cycloalkynyl groups.

When A is a keto group, linking of the keto-modified glycoprotein with the linker-conjugate preferably takes place via selective conjugation with hydroxylamine derivatives or hydrazines, resulting in respectively oximes or hydrazones. Functional group B is then preferably a primary amino group, e.g. an —NH$_2$ group, an aminooxy group, e.g. —O—NH$_2$, or a hydrazinyl group, e.g. —N(H)NH$_2$. The linker-conjugate is then preferably H$_2$N-L(D)$_r$, H$_2$N—O-L(D)$_r$ or H$_2$N—N(H)-L(D)$_r$ respectively, wherein L, D and r are as defined above.

When A is an alkynyl group, linking of the alkyne-modified glycoprotein with the linker-conjugate preferably takes place via a cycloaddition reaction, preferably a 1,3-dipolar cycloaddition. Functional group B is then preferably a 1,3-dipole, such as an azide, a nitrone or a nitrile oxide. The linker-conjugate is then preferably N$_3$-L(D)$_r$, wherein L, D and r are as defined above.

When A is a thiol group, linking of the thiol-modified glycoprotein with the linker-conjugate preferably takes place via a Michael-type addition reaction. Functional group B is then preferably an N-maleimidyl group for the Michael-type addition, a halogenated acetamido group for the nucleophilic substitution reaction, or a terminal alkene for the thiol-ene reaction. The linker-conjugate is then preferably X—CH$_2$C(O)NHL(D)$_r$ or X—CH$_2$C(O)N[L(D)$_r$]$_2$ wherein X is F, Cl, Br or I, or a maleimide-linker-conjugate (112) as illustrated below.

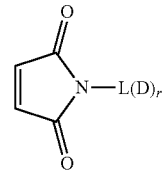

112

When A is halogen-modified glycoprotein, a halogenated acetamide-modified glycoprotein, a sulfonyloxy-modified glycoprotein or a sulfonylated hydroxy acetamide-modified glycoprotein, linking of the modified glycoprotein with the linker-conjugate preferably takes place via reaction with a thiol to form a thioether. Functional group B comprises then preferably a thiol group, and a preferred linker-conjugate is HS-L(D)$_r$. When A is halogen, a halogenated acetamido group, a sulfonyloxy group or a sulfonylated hydroxy acetamido group, linking of the modified glycoprotein with the linker-conjugate preferably takes place via reaction with a thiol to form a thioether. Functional group B comprises then preferably a thiol group, and a preferred linker-conjugate is HS-L(D)$_r$. In other words, when the modified antibody is a halogen-modified antibody, a halogenated acetamide-modified antibody, a sulfonyloxy-modified antibody or a mercaptoacetamide-modified antibody, linking of the modified antibody with the linker-conjugate preferably takes place via reaction with a thiol to form a thioether. Functional group B comprises then preferably a thiol group, and a preferred linker-conjugate is HS-L(D)$_r$.

However, functional group B may also comprise an alcohol group or an amine group.

The invention thus also relates to a process for the preparation of a protein-conjugate, comprising reacting the modified glycoprotein according to the invention with a linker-conjugate, wherein:

(a) when the modified glycoprotein is an azide-modified glycoprotein, said linker-conjugate comprises a (hetero)cycloalkynyl group or an alkynyl group, and one or more molecules of interest; or (b) when the modified glycoprotein is a keto-modified glycoprotein, said linker-conjugate comprises a primary amine group, an aminooxy group or a hydrazinyl group, and one or more molecules of interest; or (c) when the modified glycoprotein is an alkyne-modified glycoprotein, said linker-conjugate comprises an azido group, a nitrone or a nitrile oxide, and one or more molecules of interest; or (d) when the modified glycoprotein is a halogen-modified glycoprotein or a halogenated acetamido-modified glycoprotein, functional group B comprises a thiol group, an alcohol group or an amine group; or (e) when the modified glycoprotein is a thiol-modified glycoprotein or a mercaptoacetamido-modified glycoprotein, functional group B comprises an N-maleimide group or a halogenated acetamido group or an alkene; or (f) when the modified glycoprotein is a sulfonyloxy-modified glycoprotein or a sulfonylated hydroxyacetamido-modified glycoprotein, functional group B comprises thiol group, an alcohol group or an amine group.

When said modified glycoprotein is a halogen-modified glycoprotein and functional group B comprises a thiol group, said thiol group may be an aliphatic or an aromatic thiol group. In a preferred embodiment said thiol group is an aromatic thiol group.

In a preferred embodiment, the modified glycoprotein is a thiol-modified glycoprotein and functional group B comprises an N-maleimide group or a halogenated acetamido group.

In a preferred embodiment of the process for the preparation of a protein-conjugate according to the invention, linker-conjugate B-L(D), is selected from the group consisting of linker-conjugates of formula (113a), (113b), (114), (115), (116) or (117):

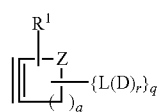

113a

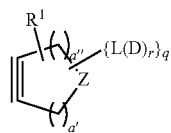

113b

N$_3$—L(D)$_r$   114

HS—L(D)$_r$   115

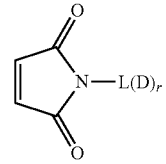

116

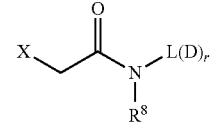

117 wherein:
L is a linker;
D is a molecule of interest;
r is 1-20;
$R^1$ is independently selected from the group consisting of hydrogen, halogen, —OR$^5$, —NO$_2$, —CN, —S(O)$_2$R$^5$, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups and wherein the alkyl groups, (hetero)aryl groups, alkyl(hetero)aryl groups and (hetero)arylalkyl groups are optionally substituted, wherein two substituents $R^1$ may be linked together to form an annelated cycloalkyl or an annelated (hetero)arene substituent, and wherein $R^5$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)aryl alkyl groups;
Z is C(R$^1$)$_2$, O, S or NR$^2$, wherein R$^2$ is R$^1$ or L(D)$_r$, and wherein L, D and r are as defined above;
q is 0 or 1, with the proviso that if q is 0 then Z is N-L(D)$_r$;
a is 1, 2, 3, 4, 5, 6, 7, 8, 9 or 10;
a' is 0, 1, 2, 3, 4, 5, 6, 7 or 8;
a" is 0, 1, 2, 3, 4, 5, 6, 7 or 8;
a'+a"<10;
X is F, Cl, Br or I; and
R$^8$ is R$^1$ or -L(D)$_r$, preferably hydrogen, -L(D)$_r$ or a $C_1$-$C_{24}$ alkyl group, more preferably hydrogen, -L(D)$_r$ or a $C_1$-$C_6$ alkyl group, even more preferably hydrogen, -L(D)$_r$ or a $C_1$, $C_2$, $C_3$ or $C_4$ alkyl group, most preferably hydrogen, methyl, ethyl, linear or branched C3 or C4 alkyl.

In another preferred embodiment of the process for the preparation of a protein-conjugate according to the invention, linker-conjugate B-L(D), is selected from the group consisting of linker-conjugates of formula (113a), (114), (115), (116) or (117), as defined above.

In a preferred embodiment, the modified glycoprotein according to the invention is an azide-modified glycoprotein, an alkyne-modified glycoprotein, a halogen-modified glycoprotein or a thiol-modified glycoprotein.

A suitable linker-conjugate for the preparation of a protein-conjugate according to the invention is a linker-conjugate comprising a functional group B and a molecule of interest. Linkers (L), also referred to as linking units, are well known in the art. In a linker-conjugate as described herein, L is linked to a molecule of interest (D) as well as to a functional group (B), as was described above. Numerous methods for linking said functional group (B) and said molecule of interest (D) to L are known in the art. As will be clear to a person skilled in the art, the choice of a suitable method for linking a functional group (B) to one end and a molecule of interest (D) to another end of a linker depends on the exact nature of the functional group (B), the linker (L) and the molecule of interest (D).

A linker may have the general structure $F^1$-L$(F^2)_r$, wherein $F^1$ represents either a functional group B or a functional group that is able to react with a functional group F on the functional group B as described above, e.g. a (hetero)cycloalkynyl group, a terminal alkynyl group, a primary amine, an aminooxy group, a hydrazyl group, an azido group, an N-maleimidyl group, an acetamido group or a thiol group. $F^2$ represents a functional group that is able to react with a functional group F on the molecule of interest.

Since more than one molecule of interest may be bonded to a linker, more than one functional group $F^2$ may be present on L. As was described above, r is 1 to 20, preferably 1 to 10, more preferably 1 to 8, even more preferably 1, 2, 3, 4, 5 or 6, even more preferably 1, 2, 3 or 4 and most preferably, r is 1 or 2.

L may for example be selected from the group consisting of linear or branched $C_1$-$C_{200}$ alkylene groups, $C_2$-$C_{200}$ alkenylene groups, $C_2$-$C_{200}$ alkynylene groups, $C_3$-$C_{200}$ cycloalkylene groups, $C_5$-$C_{200}$ cycloalkenylene groups, $C_8$-$C_{200}$ cycloalkynylene groups, $C_7$-$C_{200}$ alkylarylene groups, $C_7$-$C_{200}$ arylalkylene groups, $C_8$-$C_{200}$ arylalkenylene groups, $C_9$-$C_{200}$ arylalkynylene groups. Optionally the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups may be substituted, and optionally said groups may be interrupted by one or more heteroatoms, preferably 1 to 100 heteroatoms, said heteroatoms preferably being selected from the group consisting of O, S and $NR^5$, wherein $R^5$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups. Most preferably, the heteroatom is O.

F, $F^1$ and $F^2$ may for example be independently selected from the group consisting of hydrogen, halogen, $R^5$, $C_4$-$C_{10}$ (hetero)cycloalkyne groups, —CH=C($R^5$)$_2$, —C≡C$R^5$, —[C($R^5$)$_2$C($R^5$)$_2$O]$_q$—$R^5$, wherein q is in the range of 1 to 200, —CN, —N$_3$, —NCX, —XCN, —X$R^5$, —N($R^5$)$_2$, —$^+$N($R^5$)$_3$, —C(X)N($R^5$)$_2$, —C($R^5$)$_2$X$R^5$, —C(X)$R^5$, —C(X)X$R^5$, —S(O)$R^5$, —S(O)$_2$$R^5$, —S(O)O$R^5$, —S(O)$_2$O$R^5$, —S(O)N($R^5$)$_2$, —S(O)$_2$N($R^5$)$_2$, —OS(O)$R^5$, —OS(O)$_2$$R^5$, —OS(O)O$R^5$, —OS(O)$_2$O$R^5$, —P(O)($R^5$)(O$R^5$), —P(O)(O$R^5$)$_2$, —OP(O)(O$R^5$)$_2$, —Si($R^5$)$_3$, —XC(X)$R^5$, —XC(X)X$R^5$, —XC(X)N($R^5$)$_2$, —N($R^5$)C(X)$R^5$, —N($R^5$)C(X)X$R^5$ and —N($R^5$)C(X)N($R^5$)$_2$, wherein X is oxygen or sulphur and wherein $R^5$ is as defined above.

Examples of suitable linking units include (poly)ethylene glycol diamines (e.g. 1,8-diamino-3,6-dioxaoctane or equivalents comprising longer ethylene glycol chains), polyethylene glycol or polyethylene oxide chains, polypropylene glycol or polypropylene oxide chains and 1,x-diaminoalkanes wherein x is the number of carbon atoms in the alkane.

Another class of suitable linkers comprises cleavable linkers. Cleavable linkers are well known in the art. For example Shabat et al., *Soft Matter* 2012, 6, 1073, incorporated by reference herein, discloses cleavable linkers comprising self-immolative moieties that are released upon a biological trigger, e.g. an enzymatic cleavage or an oxidation event. Some examples of suitable cleavable linkers are peptide-linkers that are cleaved upon specific recognition by a protease, e.g. cathepsin, plasmin or metalloproteases, or glycoside-based linkers that are cleaved upon specific recognition by a glycosidase, e.g. glucoronidase, or nitroaromatics that are reduced in oxygen-poor, hypoxic areas.

As was described above, when the modified glycoprotein is an azide-modified glycoprotein, it is preferred that the linker-conjugate is a (hetero)cycloalkyne linker-conjugate of formula (113a):

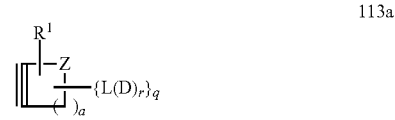

113a wherein:
L is a linker;
D is a molecule of interest;
r is 1-20;
$R^1$ is independently selected from the group consisting of hydrogen, halogen, —O$R^5$, —NO$_2$, —CN, —S(O)$_2$$R^5$, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups and wherein the alkyl groups, (hetero)aryl groups, alkyl(hetero)aryl groups and (hetero)arylalkyl groups are optionally substituted, wherein two substituents $R^1$ may be linked together to form an annelated cycloalkyl or an annelated (hetero)arene substituent, and wherein $R^5$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups;
Z is C($R^1$)$_2$, O, S or $NR^2$, wherein $R^2$ is $R^1$ or L(D)$_r$, and wherein L, D and r are as defined above;
q is 0 or 1, with the proviso that if q is 0 then Z is N-L(D)$_r$; and
a is 1, 2, 3, 4, 5, 6, 7, 8, 9 or 10.

In a further preferred embodiment, a is 5, i.e. said (hetero)cycloalkynyl group is preferably a (hetero)cyclooctyne group.

In another preferred embodiment, Z is C($R^2$)$_z$ or $NR^2$. When Z is C($R^2$)$_2$ it is preferred that $R^2$ is hydrogen. When Z is $NR^2$, it is preferred that $R^2$ is L(D)$_r$. In yet another preferred embodiment, r is 1 to 10, more preferably, r is 1, 2, 3, 4, 5 or 6, even more preferably r is 1, 2, 3 or 4, even more preferably r is 1 or 2, and most preferably is 1. In another preferred embodiment, q is 1 or 2, more preferably q is 1. Even more preferably, r is 1 and q is 1, and most preferably, a is 5 and r is 1 and q is 1.

In another preferred embodiment, when the modified glycoprotein is an azide-modified glycoprotein, the linker-conjugate is a (hetero)cycloalkyne linker-conjugate of formula (113b):

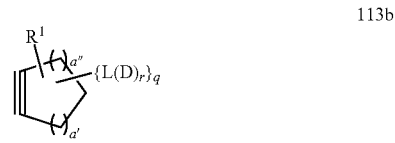

113b wherein:
L is a linker;
D is a molecule of interest;
r is 1-20;

$R^1$ is independently selected from the group consisting of hydrogen, halogen, —$OR^5$, —$NO_2$, —CN, —$S(O)_2R^5$, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups and wherein the alkyl groups, (hetero)aryl groups, alkyl(hetero)aryl groups and (hetero)arylalkyl groups are optionally substituted, wherein two substituents $R^1$ may be linked together to form an annelated cycloalkyl or an annelated (hetero)arene substituent, and wherein $R^5$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups;

Z is $C(R^1)_2$, O, S or $NR^2$, wherein $R^2$ is $R^1$ or $L(D)_r$, and wherein L, D and r are as defined above;

q is 0 or 1, with the proviso that if q is 0 then Z is $N$-$L(D)_r$;

a' is 0, 1, 2, 3, 4, 5, 6, 7 or 8;

a" is 0, 1, 2, 3, 4, 5, 6, 7 or 8; and a'+a"<10.

In a further preferred embodiment, a'+a" is 4, 5, 6 or 7, more preferably a'+a" is 4, 5 or 6 and most preferably a'+a" is 5, i.e. said (hetero)cycloalkynyl group is preferably a (hetero)cyclooctyne group.

In another preferred embodiment, Z is $C(R^2)_2$ or $NR^2$. When Z is $C(R^2)_2$ it is preferred that $R^2$ is hydrogen. When Z is $NR^2$, it is preferred that $R^2$ is $L(D)_r$. In yet another preferred embodiment, r is 1 to 10, more preferably, r is 1, 2, 3, 4, 5 or 6, even more preferably r is 1, 2, 3 or 4, even more preferably r is 1 or 2, and most preferably is 1. In another preferred embodiment, q is 1 or 2, more preferably q is 1. Even more preferably, r is 1 and q is 1, and most preferably, a'+a" is 5 and r is 1 and q is 1.

The process for the preparation of a protein-conjugate wherein an azide-modified glycoprotein according to the invention is reacted with a linker-conjugate comprising a (hetero)cycloalkyne group (113a) is shown in Scheme 4, wherein Pr, $R^1$, Su, Q, Z, L, D, a, b, p, q, x and y are as defined above. In a preferred embodiment, the protein-conjugate according to the invention is according to formula (118).

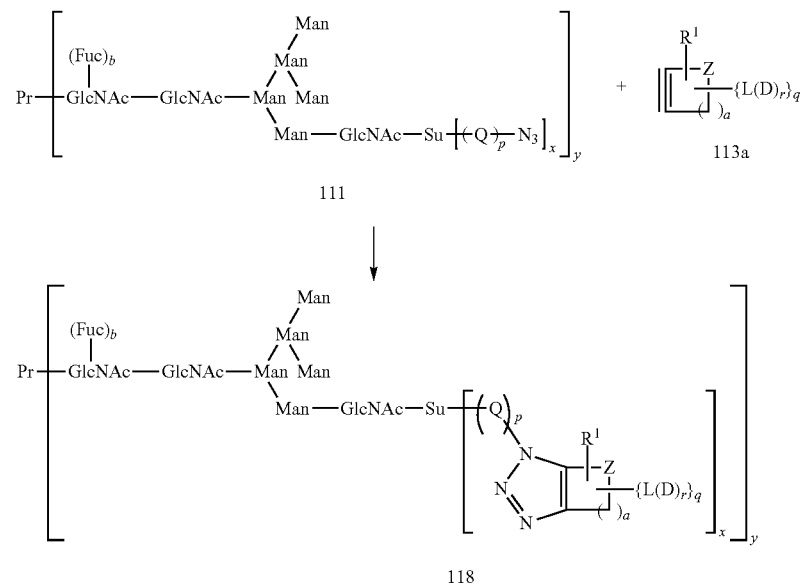

In another preferred embodiment, the protein-conjugate according to the invention is according to formula (118b), wherein Pr, $R^1$, Su, Q, Z, L, D, a', a", b, p, q, x and y are as defined above:

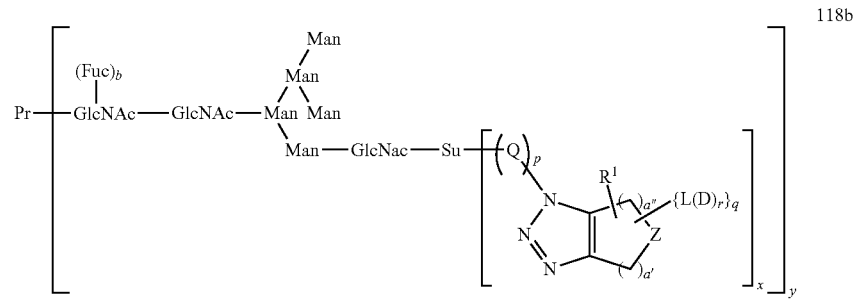

The value of p and the nature of Q depend on the azide-substituted sugar or sugar derivative Su(A)$_x$ that is present in the azide-modified glycoprotein according to the invention that is linked to a linker-conjugate. If an azide in Su(A)$_x$ is present on the C2, C3, or C4 position of the sugar or the sugar derivative (instead of a sugar OH-group), then p is 0. If the Su(A)$_x$ is an azidoacetamido-sugar derivative, Su(A)$_x$ is e.g. GalNAz or GlcNAz, then p is 1 and Q is —N(H)C(O)CH$_2$—. If the azide in Su(A)$_x$ is present on the C6 position of the sugar or the sugar derivative, then p is 1 and Q is —CH$_2$—.

In a preferred embodiment, if q is 1 then Z is C(R$^1$)$_2$, O, S or NR$^1$.

In another preferred embodiment, a is 5, i.e. said (hetero)cycloalkynyl group is preferably a (hetero)cyclooctyne group. In another preferred embodiment, Z is C(R$^2$)$_2$ or NR$^2$. When Z is C(R$^2$)$_2$ it is preferred that R$^2$ is hydrogen When Z is NR$^2$, it is preferred that R$^2$ is L(D)$_r$. In yet another preferred embodiment, r is 1 to 10, more preferably, r is 1, 2, 3, 4, 5, 6 7 or 8, more preferably r is 1, 2, 3, 4, 5 or 6, most preferably r is 1, 2, 3 or 4.

The L(D)$_r$ substituent may be present on a C-atom in said (hetero)cycloalkynyl group, or, in case of a heterocycloalkynyl group, on the heteroatom of said heterocycloalkynyl group. When the (hetero)cycloalkynyl group comprises substituents, e.g. an annelated cycloalkyl, the L(D)$_r$ substituent may also be present on said substituents.

The methods to connect a linker L to a (hetero)cycloalkynyl group on the one end and to a molecule of interest on the other end, in order to obtain a linker-conjugate, depend on the exact the nature of the linker, the (hetero)cycloalkynyl group and the molecule of interest. Suitable methods are known in the art.

Preferably, the linker-conjugate comprises a (hetero)cyclooctyne group, more preferably a strained (hetero)cyclooctyne group. Suitable (hetero)cycloalkynyl moieties are known in the art. For example DIFO, DIFO2 and DIFO 3 are disclosed in US 2009/0068738, incorporated by reference. DIBO is disclosed in WO 2009/067663, incorporated by reference. BARAC is disclosed in *J. Am. Chem. Soc.* 2010, 132, 3688-3690 and US 2011/0207147, both incorporated by reference.

Preferred examples of linker-conjugates comprising a (hetero)cyclooctyne group are shown below.

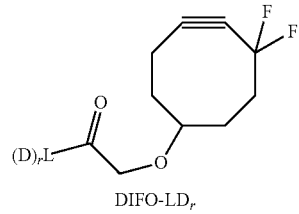

DIFO-LD$_r$ (119)

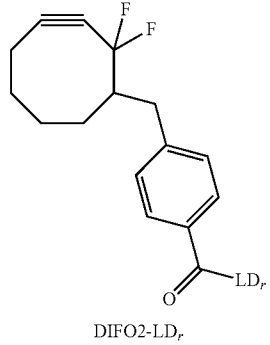

DIFO2-LD$_r$ (120)

DIFO3-LD$_r$ (121)

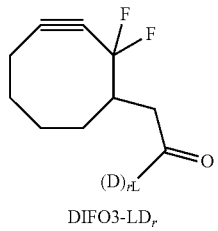

DIBO-LD$_r$ (122)

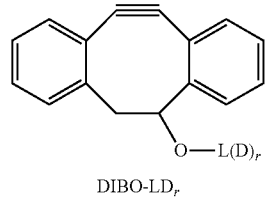

BARAC-LD$_r$ (123)

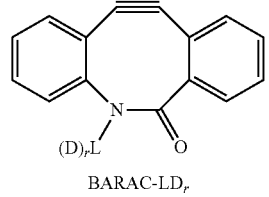

Other cyclooctyne moieties that are known in the art are DIBAC (also known as ADIBO or DBCO) and BCN. DIBAC is disclosed in *Chem. Commun.* 2010, 46, 97-99, incorporated by reference. BCN is disclosed in WO 2011/136645, incorporated by reference.

In a preferred embodiment, said linker-conjugate has the Formula (124):

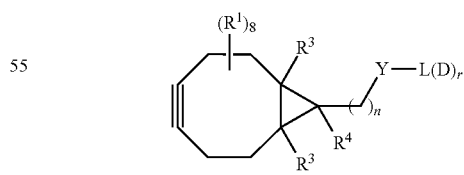

124 wherein:
R$^1$, L, D and r are as defined above;
Y is O, S or NR$^2$, wherein R$^2$ is as defined above;
R$^3$ is independently selected from the group consisting of hydrogen, halogen, C$_1$-C$_{24}$ alkyl groups, C$_6$-C$_{24}$ (hetero)aryl groups, C$_7$-C$_{24}$ alkyl(hetero)aryl groups and C$_7$-C$_{24}$ (hetero)arylalkyl groups;

R$^4$ is selected from the group consisting of hydrogen, Y-L(D)$_r$, —(CH$_2$)$_n$—Y-L(D)$_r$, halogen, C$_1$-C$_{24}$ alkyl groups, C$_6$-C$_{24}$ (hetero)aryl groups, C$_7$-C$_{24}$ alkyl(hetero)aryl groups and C$_7$-C$_{24}$ (hetero)arylalkyl groups, the alkyl groups optionally being interrupted by one of more heteroatoms selected from the group consisting of O, N and S, wherein the alkyl groups, (hetero)aryl groups, alkyl (hetero)aryl groups and (hetero)arylalkyl groups are independently optionally substituted; and n is 1, 2, 3, 4, 5, 6, 7, 8, 9 or 10.

In a further preferred embodiment, R$^1$ is hydrogen. In another preferred embodiment, R$^3$ is hydrogen. In another preferred embodiment, n is 1 or 2. In another preferred embodiment, R$^4$ is hydrogen, Y-L(D)$_r$ or —(CH$_2$)$_n$—Y-L(D)$_r$. In another preferred embodiment, R$^2$ is hydrogen or L(D)$_r$. In a further preferred embodiment, the linker-conjugate has the Formula 125:

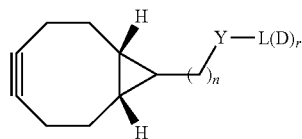

125 wherein Y, L, D, n and r are as defined above.

Figure 8:
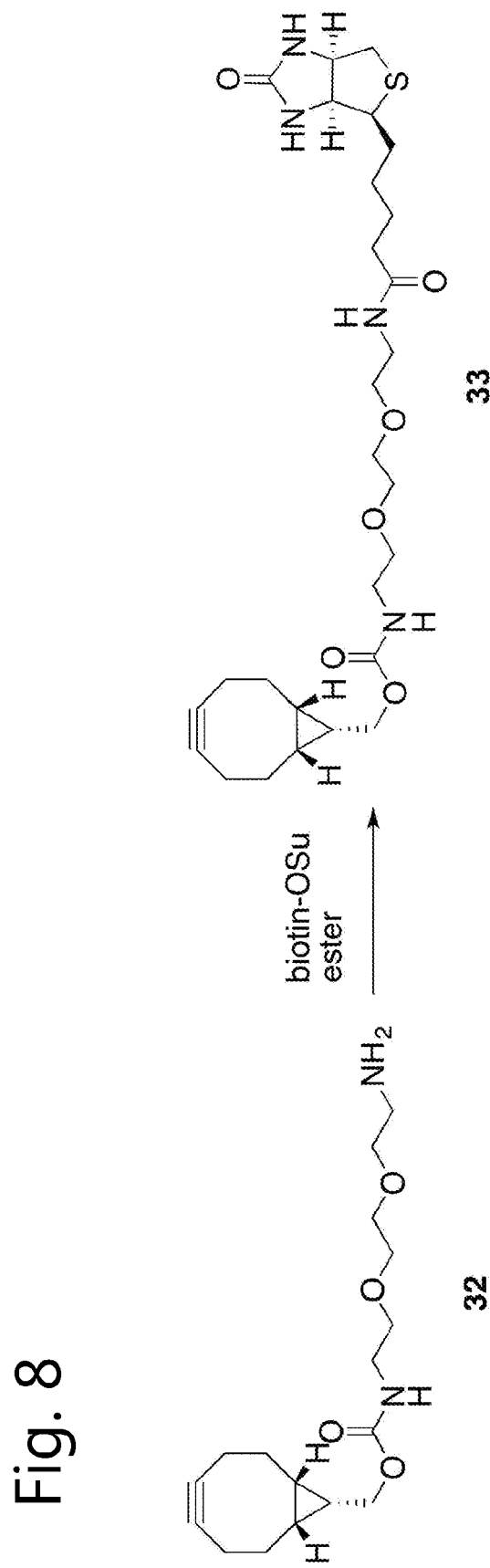
FIG. 8 shows the synthetic scheme for synthesis of BCN-biotin 32.
Figure 9:
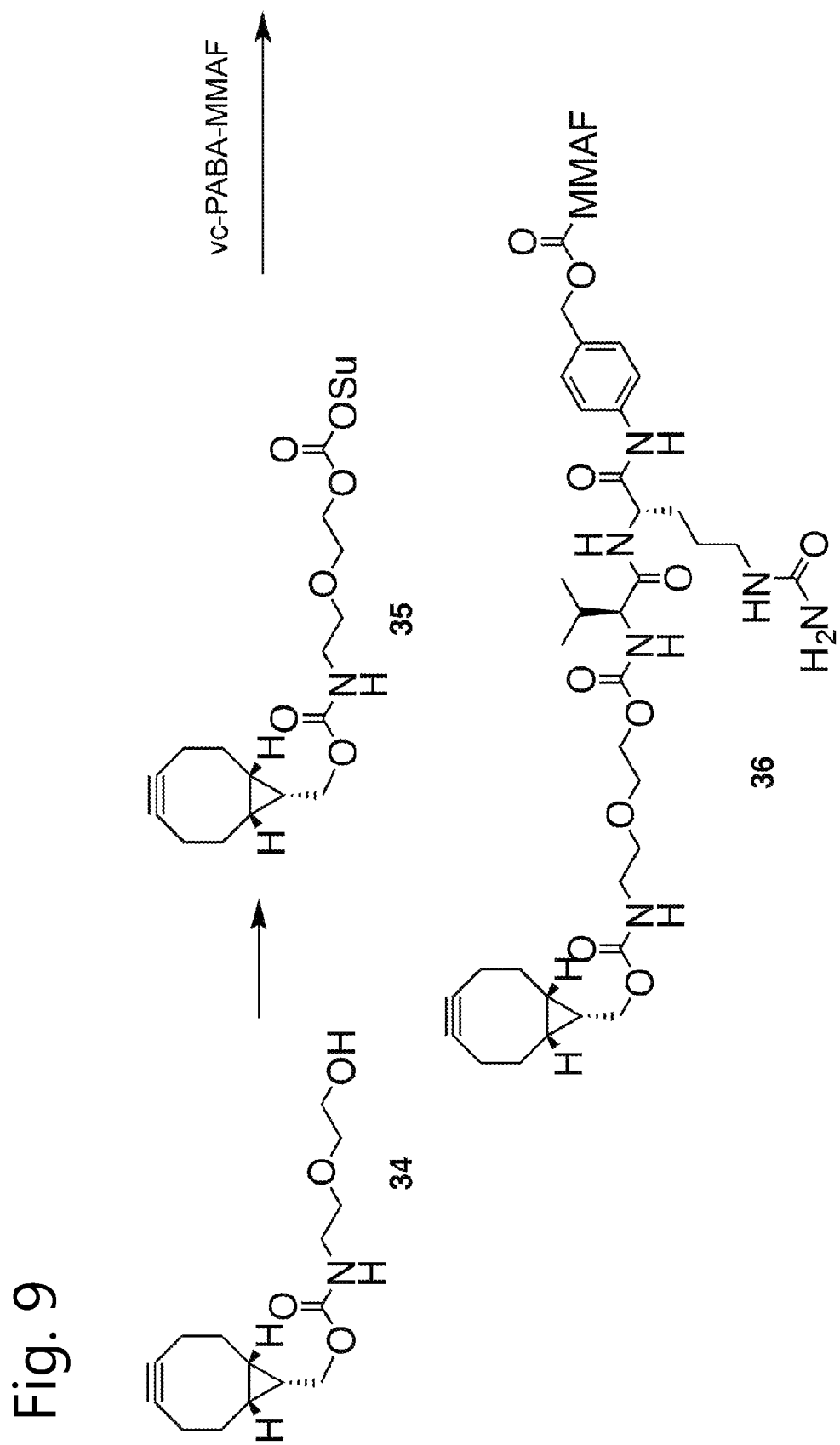
FIG. 9 shows the reaction scheme for the synthesis of BCN-MMAF conjugate (36).
Figure 10:
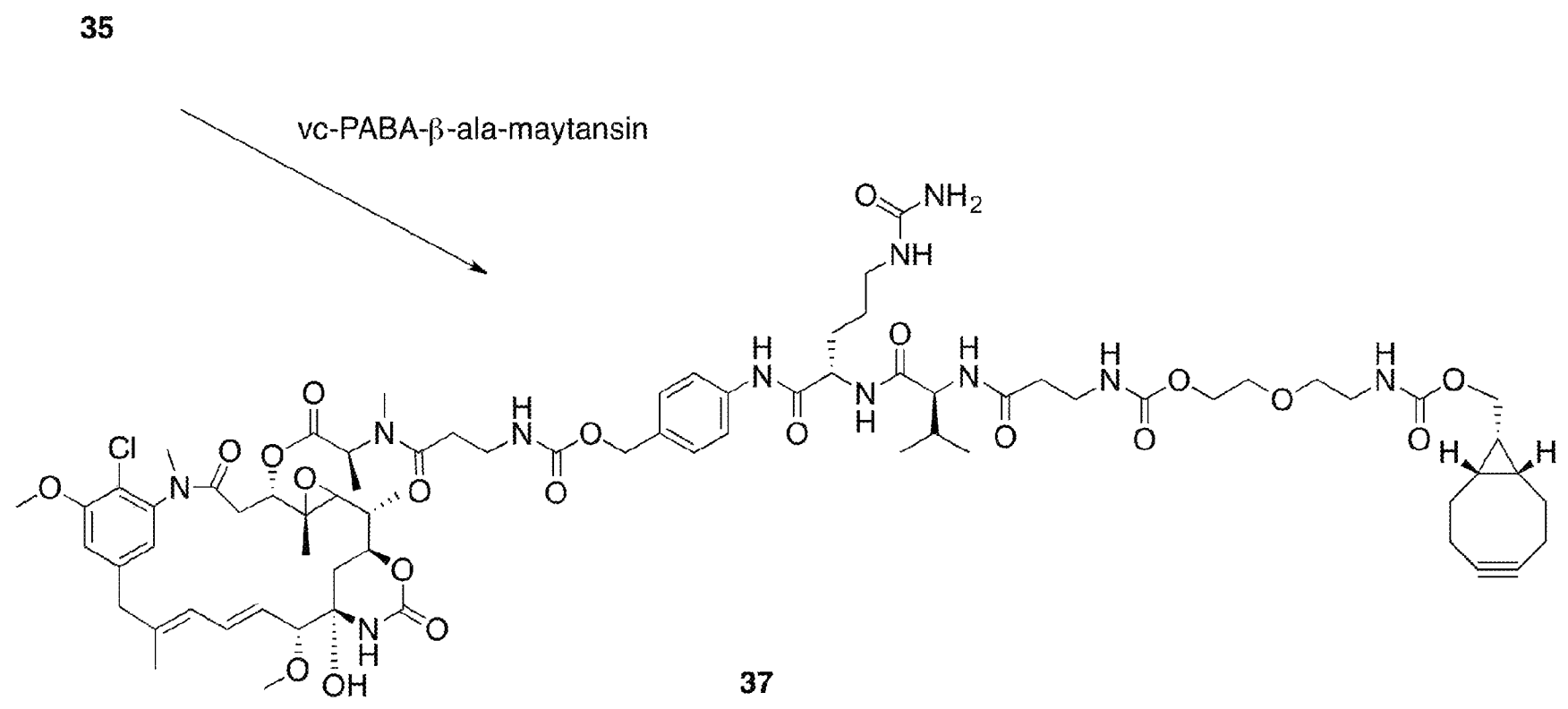

Examples of a linker-conjugate according to formula (125) are shown in FIGS. 8, 9 and 10. FIG. 8 shows the synthetic scheme for synthesis of BCN-biotin (32). FIG. 9 shows the reaction scheme for the synthesis of BCN-MNIAF conjugate (36). FIG. 10 shows the reaction scheme for the synthesis of BCN-maytansinoid conjugate (37).

In another preferred embodiment, said linker-conjugate has the Formula (126):

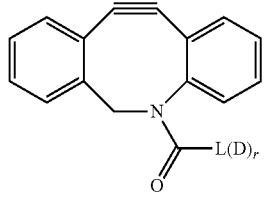

126 wherein L, D and r are as defined above.

As described above, in a preferred embodiment the modified glycoprotein is a thiol-modified glycoprotein and functional group B comprises an N-maleimide group or a halogenated acetamido group.

The invention further relates to the use of a glycoprotein according to the invention in the preparation of a protein-conjugate, wherein a protein-conjugate is defined as a protein that is conjugated to a molecule of interest (D) via a linker (L). The invention also relates to the use of an antibody according to the invention in the preparation of an antibody-conjugate, wherein an antibody-conjugate is defined as an antibody that is conjugated to a molecule of interest (D) via a linker (L).

Protein-Conjugate

The invention further relates to a protein-conjugate obtainable by the process for the preparation of a protein-conjugate according to the invention. In a preferred embodiment, the protein is an antibody. The invention also relates to an antibody-conjugate obtainable by the process for the preparation of an antibody-conjugate according to the invention. Said processes and preferred embodiments thereof are described in detail above.

In particular, the invention relates to a glycoprotein-conjugate obtainable by a process comprising the steps of:

(a) contacting a glycoprotein comprising a glycan of the formula GlcNAcMan$_5$GlcNAc$_2$ with Su(A)$_x$-P in the presence of a suitable catalyst; wherein the core GlcNAc residue of said glycan is optionally fucosylated; wherein a suitable catalyst is defined as a galactosyltransferase or a galactosyltransferase comprising a mutant catalytic domain, wherefore Su(A)$_x$-P is a substrate; wherein Su(A)$_x$ is a sugar derivative comprising x functional groups A wherein x is 1, 2, 3 or 4 and A is independently selected from the group consisting of an azido group, a keto group, an alkynyl group, a thiol group or a precursor thereof, a halogen, a sulfonyloxy group, a halogenated acetamido group, a mercaptoacetamido group and a sulfonylated hydroxyacetamido group; wherein P is a nucleotide; wherein a modified glycoprotein is defined as a glycoprotein comprising a glycan of the formula Su(A)$_x$GlcNAcMan$_5$GlcNAc$_2$ wherein the core GlcNAc residue is optionally fucosylated; and wherein GlcNAcMan$_5$GlcNAc$_2$ is a glycan according to formula (101) and Su(A)$_x$GlcNAcMan$_5$GlcNAc$_2$ is a glycan according to formula (102):

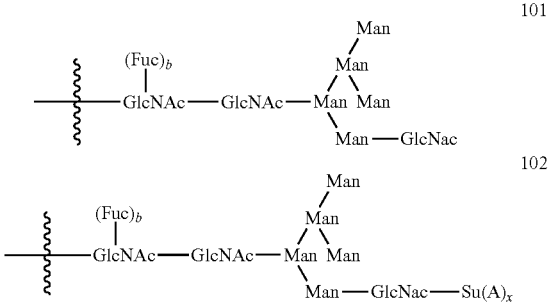

wherein b is 0 or 1 and Su(A)$_x$ is as defined above;

to obtain a modified glycoprotein; and (b) reacting the obtained modified glycoprotein with a linker-conjugate, wherein said linker-conjugate comprises a functional group B and one or more molecules of interest, wherein said functional group B is a functional group that is capable of reacting with a functional group A of the modified glycoprotein.

The processes of step (a) and (b) as well as their preferred embodiments are described in detail above. It is particularly preferred that the catalyst in step (a) is selected from the group consisting of β(1,4)-galactosyltransferases, β(1,3)-N-galactosyltransferases, β(1,4)-galactosyltransferases comprising a mutant catalytic domain and β(1,3)-N-galactosyltransferases comprising a mutant catalytic domain.

The invention further relates to a protein-conjugate according to formula (118a) and (118b) as described above, and (127), (128), (129) and (130) as illustrated below.

As was described above, the value of p and the nature of Q depend on the azide-substituted sugar or sugar derivative Su(A)$_x$ that is present in the azide-modified glycoprotein that is linked to a linker-conjugate. If the azide in Su(A)$_x$ is present on the C2, C3, or C4 position of the sugar derivative, then p is 0. If the Su(A) is an azidoacetamido-sugar derivative, Su(A)$_x$ is e.g. GalNAz or GlcNAz, then p is 1 and Q is —N(H)C(O)CH$_2$—. If the azide in Su(A)$_x$ is present on the C6 position of the sugar or the sugar derivative, then p is 1 and Q is —CH$_2$—.

Molecules of interest (D) are also described in more detail above. The protein-conjugate may comprise more than one molecule of interest. A protein-conjugate comprises more than one molecule of interest for example when it is linked to more than one linker-conjugate, when one linker-conjugate comprises more than one molecule of interest, or both.

Preferably the molecule of interest is selected from the group consisting of a reporter molecule, an active substance, an enzyme, an amino acid, a protein, a peptide, a polypeptide, an oligonucleotide, a glycan, a (poly)ethylene glycol diamine, a polyethylene glycol chain, a polyethylene oxide chain, a polypropylene glycol chain, a polypropylene oxide chain and a 1,x-diaminoalkane (wherein x is the number of carbon atoms in the alkane and x is 1-200), an azide and a (hetero)cycloalkynyl moiety, preferably a bivalent or bifunctional (hetero)cycloalkynyl moiety.

Preferably the molecule of interest is selected from the groups consisting of an active substance, a reporter molecule, an azide and a (hetero)cycloalkyne group. When the molecule of interest is an active substance, the antibody-conjugate may also be referred to as an antibody drug conjugate (ADC), as described in more detail below.

In a preferred embodiment, an azide-modified glycoprotein is reacted with a cyclooctyne according to formula (126). A preferred protein-conjugate according to the invention is according to formula (127):

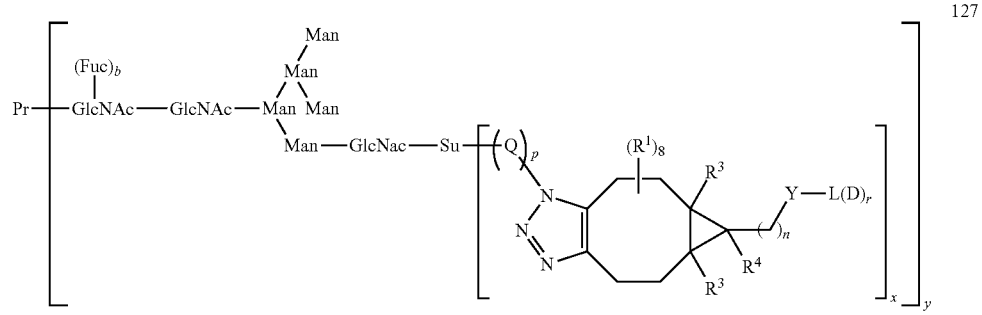

wherein Pr, L, D, Y, Su, Q, x, y, b, p, R$^1$, R$^3$, R$^4$, n and r are as defined above.

In a further preferred embodiment, R$^1$, R$^3$ and R$^4$ are hydrogen and n is 1 or 2, and in an even more preferred embodiment x is 1.

In another preferred embodiment, an azide-modified glycoprotein is reacted with a cyclooctyne according to formula (124). A preferred protein-conjugate is of the Formula (128):

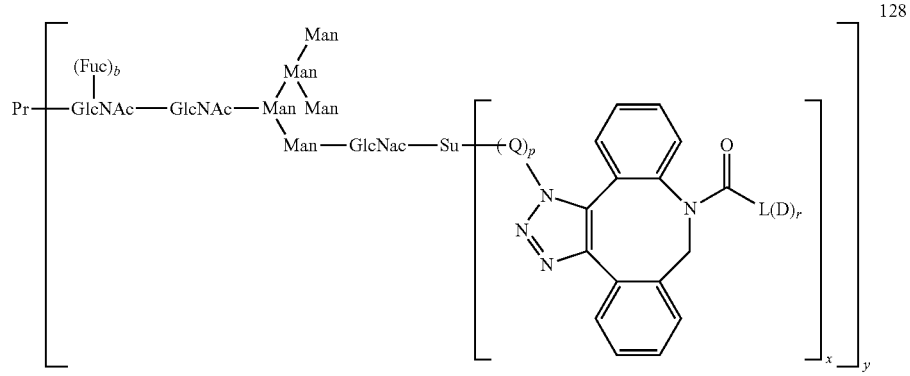

wherein Pr, L, D, Su, b, p, x, y and Q are as defined above.

Protein-conjugate (128) is an example of a compound that may exist in several regioisomers. Another regioismer is shown below.

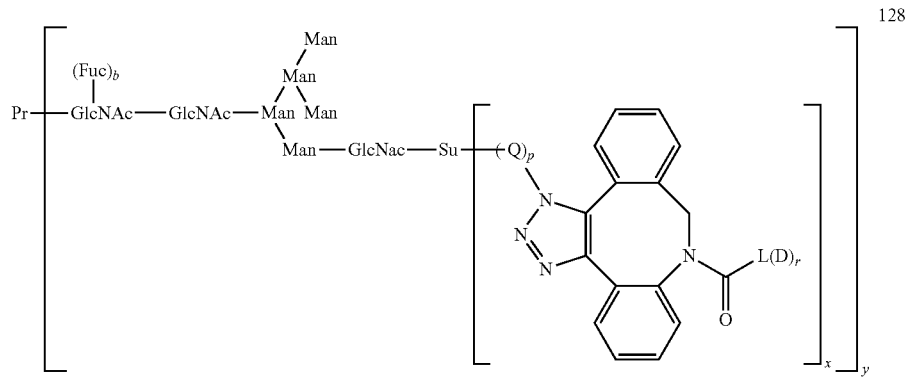

wherein Pr, L, D, Su, b, p, x, y and Q are as defined above.

In a preferred embodiment, the protein-conjugate according to the invention is an antibody-conjugate (AC), i.e. in a preferred embodiment Pr is Ab. Antibody-conjugates are described in more detail below.

In a further preferred embodiment, y is 1-10, preferably y is 1, 2, 3, 4, 5, 6, 7 or 8, more preferably y is 1, 2, 3 or 4 and most preferably, y is 1, 2 or 4.

In another preferred embodiment, x is 1 or 2, more preferably x is 1.

In yet another preferred embodiment, y is 1, 2 or 4 and x is 1 or 2, more preferably y is 2 or 4 and x is 1.

When a thiol-modified glycoprotein is reacted with a linker-conjugate comprising a functional group B that comprises an N-maleimide group, preferably the protein-conjugate according to the invention is according to formula (129):

r is 1 to 20;
x is 1, 2, 3 or 4;
y is 1 to 20;
b is 0 or 1;
p is 0 or 1;
Q is —N(H)C(O)CH$_2$— or CH$_2$; and
Su is a sugar or sugar derivative.

The value of p and the nature of Q depend on the nature of the modified sugar or sugar derivative Su(A)$_x$ that is used for the preparation of the glycoprotein-conjugate according to the process of the invention. If in S(A)$_x$ a thiol group is present on the C2, C3, or C4 position of the sugar or the sugar derivative (instead of a sugar OH-group), then p is 0. If the S(A)$_x$ is a 2-(mercaptoacetamido)-2-deoxy sugar derivative (i.e. a mercaptoacetamido group is present on C2 of said sugar or sugar derivative), S(A)$_x$ is e.g. GalNAcSH or GlcNAcSH, then p is 1 and Q is —N(H)C(O)CH$_2$—. If the thiol in S(A)$_x$ is present on the C6 position of the sugar or the sugar derivative, then p is 1 and Q is —CH$_2$—.

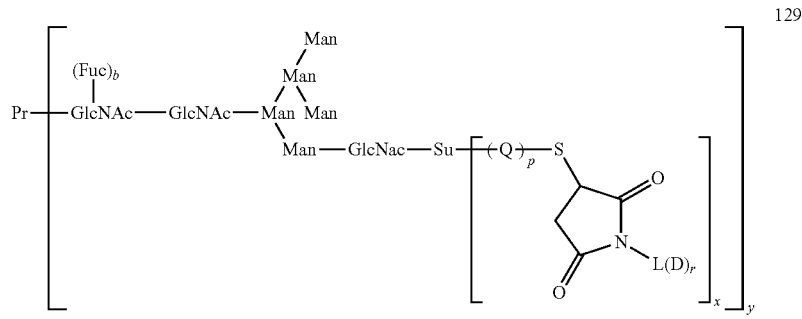

wherein:
Pr represents a protein;
L is a Linker;
D is a molecule of interest;

When a thiol-modified glycoprotein is reacted with of a linker-conjugate comprising a functional group B that comprises a halogenated acetamido group, preferably the protein-conjugate according to the invention is according to formula (130):

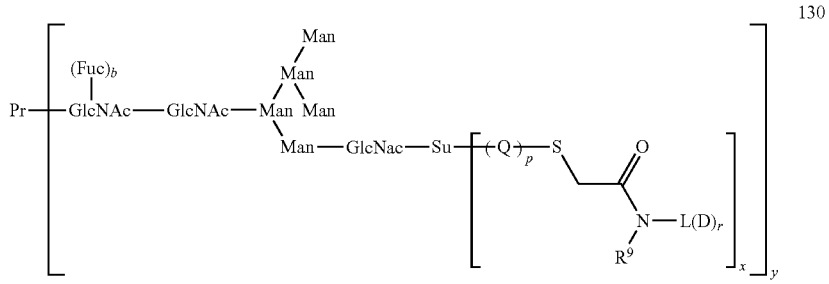

wherein Pr, L, D, r, x, y, b, p, Q and Su are as defined above for (121), and $R^9$ is selected from the group consisting of $L(D)_r$, hydrogen, $C_1$-$C_{24}$ alkyl groups, $C_6$-$C_{24}$ aryl groups $C_7$-$C_{24}$ alkylaryl groups and $C_7$-$C_{24}$ arylalkyl groups, the $C_1$-$C_{24}$ alkyl groups, $C_6$-$C_{24}$ aryl groups $C_7$-$C_{24}$ alkylaryl groups and $C_7$-$C_{24}$ arylalkyl groups optionally being substituted. Preferably, $R^9$ is selected from the group consisting of $L(D)_r$, hydrogen, $C_1$-$C_{12}$ alkyl groups, $C_6$-$C_{12}$ aryl groups $C_7$-$C_{12}$ alkylaryl groups and $C_7$-$C_{122}$ arylalkyl groups, the $C_1$-$C_{12}$ alkyl groups, $C_6$-$C_{12}$ aryl groups $C_7$-$C_{12}$ alkylaryl groups and $C_7$-$C_{12}$ arylalkyl groups optionally being substituted. More preferably, $R^9$ is selected from the group consisting of $L(D)_r$, hydrogen, $C_1$-$C_6$ alkyl groups, $C_6$-$C_{12}$ aryl groups $C_7$-$C_{12}$ alkylaryl groups and $C_7$-$C_{12}$ arylalkyl groups, the $C_1$-$C_6$ alkyl groups, $C_6$-$C_{12}$ aryl groups $C_7$-$C_{12}$ alkylaryl groups and $C_7$-$C_{12}$ arylalkyl groups optionally being substituted. Even more preferably, $R^9$ is H, $C_1$, $C_2$, $C_4$ or $C_4$ alkyl or $C_6$-$C_{12}$ aryl. Most preferably, $R^9$ is H or methyl.

Also in this embodiment the value of p and the nature of Q depend on the nature of the modified sugar or sugar derivative $Su(A)_x$ that is used for the preparation of the glycoprotein-conjugate according to the process of the invention. If in $S(A)_X$ a halogen is present on the C2, C3, or C4 position of the sugar or the sugar derivative (instead of a sugar OH-group), then p is 0. If the $S(A)_X$ is a 2-(chloroacetamido)-2-deoxy sugar derivative (i.e. a halogenated acetamido group is present on C2 of said sugar or sugar derivative), $S(A)_X$ is e.g. GalNAcCl or GlcNAcCl, then p is 1 and Q is —N(H)C(O)CH$_2$—. If the halogen in $S(A)_X$ is present on the C6 position of the sugar or the sugar derivative, then p is 1 and Q is —CH$_2$—.

Antibody-Conjugate and Antibody-Drug Conjugate

In a preferred embodiment, the protein-conjugate according to the invention, as described in more detail above, is an antibody-conjugate (AC). An antibody-conjugate is herein defined as an antibody that is conjugated to a molecule of interest (D) via a linker (L). A molecule of interest (D), and preferred embodiments thereof, are described in more detail above.

In a further preferred embodiment, the antibody-conjugate according to the invention is an antibody-drug conjugate (ADC). An antibody-drug conjugate is herein defined as an antibody that is conjugated to a molecule of interest (D) via a linker (L), wherein D is an active substance. More preferably D is selected from the group consisting of drugs and prodrugs.

More preferably, the active substance is selected from the group consisting of pharmaceutically active compounds, in particular low to medium molecular weight compounds (e.g. about 200 to about 1500 Da, preferably about 300 to about 1000 Da), such as for example cytotoxins, antiviral agents, antibacterials agents, peptides and oligonucleotides. Examples of cytotoxins include colchicine, vinca alkaloids, camptothecins, doxorubicin, daunorubicin, taxanes, calicheamycins, tubulysins, irinotecans, an inhibitory peptide, amanitin, deBouganin, duocarmycins, maytansines, auristatins or pyrrolobenzodiazepines (PBDs), in particular camptothecins, doxorubicin, daunorubicin, taxanes, calicheamycins, duocarmycins, maytansines, auristatins or pyrrolobenzodiazepines (PBDs). In a preferred embodiment, the cytotoxin is selected from the group consisting of camptothecins, doxorubicin, daunorubicin, taxanes, calicheamycins, duocarmycins, maytansines, auristatins and pyrrolobenzodiazepines (PBDs). In another preferred embodiment, the cytotoxin is selected from the group consisting of colchicine, vinca alkaloids, tubulysins, irinotecans, an inhibitory peptide, amanitin and deBouganin.

The invention thus also relates to an antibody-conjugate obtainable by the process for the preparation of an antibody-conjugate according to the invention.

The preferred embodiments described above for a protein-conjugate also hold when the protein is an antibody, i.e. said preferred embodiments also hold for an antibody-conjugate.

In a preferred embodiment of the antibody-conjugate according to the invention, the molecule of interest is an active substance.

Antibody-conjugates according to formulas (127), (128), (129) (130) are particularly preferred embodiments of the antibody-conjugates according to the invention.

Also for the antibody-conjugates according to the invention, it is preferred that x is 1 or 2 and/or that y is 1 or 2. It is further preferred that x is 1 and y is 1 or 2, more preferably x is 1 and y is 2. In another preferred embodiment, x is 2 and y is one or 2, preferably x is 2 and y is 2. In these embodiments, it is further preferred that r is 1 or 2, preferably r is 1. In a particular preferred embodiment x is 1, y is 2 and r is 1. In another particularly preferred embodiment, x is 2, y is 2 and r is 1. In another particularly preferred embodiment, x is 1, y is 2 and r is 2.

The invention further relates to an antibody-conjugate according to the invention, wherein the molecule of interest is an active substance, for use as a medicament.

The invention also relates to the use of an antibody-conjugate according to the invention, wherein the molecule of interest is an active substance, for use in the treatment of cancer.

The invention further relates to an antibody-conjugate according to the invention, wherein the molecule of interest is an active substance, for use in the treatment of breast cancer, more preferably for use in the treatment of HER2-positive breast cancer.

The invention also relates to a method treating cancer by administering an antibody-drug conjugate according to the invention.

The invention also relates to a method treating breast cancer by administering an antibody-drug conjugate according to the invention.

The invention also relates to a method treating HER2-positive breast cancer by administering an antibody-drug conjugate according to the invention.

The modified antibody, the antibody-conjugate and the processes for the preparation thereof according to the invention have several advantages over the processes, modified antibodies and antibody-conjugates known in the art.

As was described above, the known processes for conjugation of a linker-toxin to antibodies still need to be improved, in terms of control of both site-specificity and stoichiometry. Despite the ability of ADCs to home in on their targets, the amount of drug estimated to get inside tumor cells is typically<2% of an administered dose. This problem is amplified by the unpredictable conjugation results of ADCs known in the art. It is important to avoid underconjugated antibodies, which decrease the potency, as well as highly conjugated species, which may have markedly decreased circulating half-lives, impaired binding to the target protein, and increased toxicity.

For antibody-drug conjugates, a measure for the loading of molecules of interest (e.g. drugs, active substances) onto the antibody is the so-called Drug to Antibody Ratio (DAR), which gives the average number of active substance molecules per antibody, calculated from a statistical distribution. The theoretical maximum value of DAR for a certain type of ADC is equal to the number of anchoring sites. As was described above, processes for the preparation of ADCs known from the prior art generally result in a product comprising a mixture of antibody-conjugates with a varying number of molecules of interest present in each antibody-conjugate, and in a DAR with a high standard deviation.

One of the advantages of the modified antibodies and the antibody-conjugates according to the invention is that these antibodies and antibody-conjugates are homogeneous, both in site-specificity and stoichiometry. Said modified antibodies and antibody-conjugates are obtained with a DAR very near to the theoretical value of 2, and with a very low standard deviation. This also means that the antibody-conjugates according to the invention result in a more consistent product for preclinical testing.

The advantageous homogeneity of the antibody-drug conjugate is also the result of the reduced number of glycosylation forms present. It is known to someone skilled in the art that monoclonal antibodies expressed in mammalian cellular system carry a range (>30) of different glycoforms, the major six of which are depicted in FIG. 1. In a typical mAb-to-ADC conversion process, all glycoforms on the antibody will be retained, hence leading to increased heterogeneity.

Figure 2:
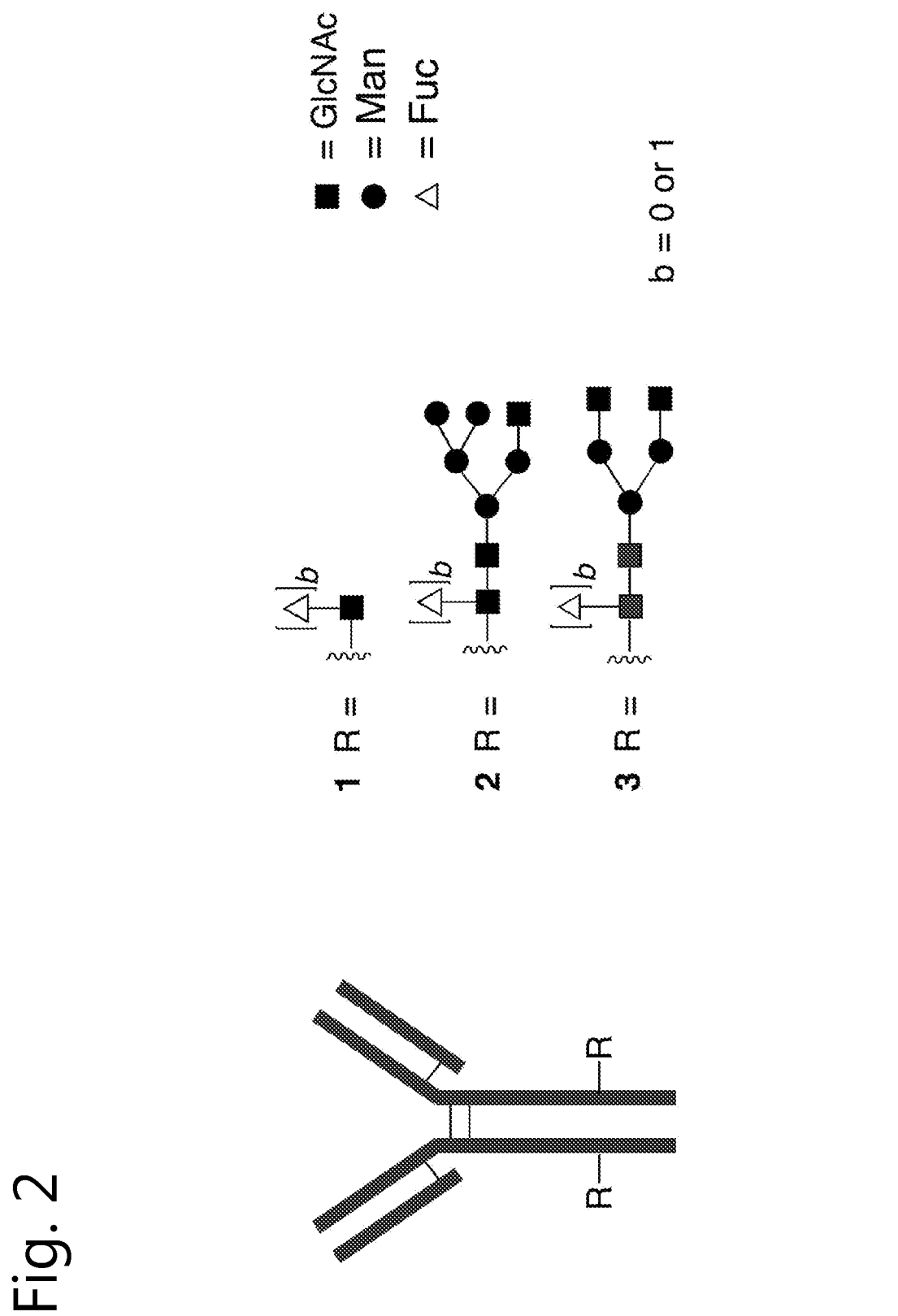
FIG. 2 shows the structures of different GlcNAc-terminated glycans of a mAb that may be obtained by trimming with an endo-glycosidase trimming (leading to 1) or trimming by sialidase and galactosidase (leading to 3). Glycoform 2 can be obtained by expression of a mAb in a mammalian system in the presence of swainsonine or by expression in an engineered host organism, e.g. Pichia.
Figure 3:
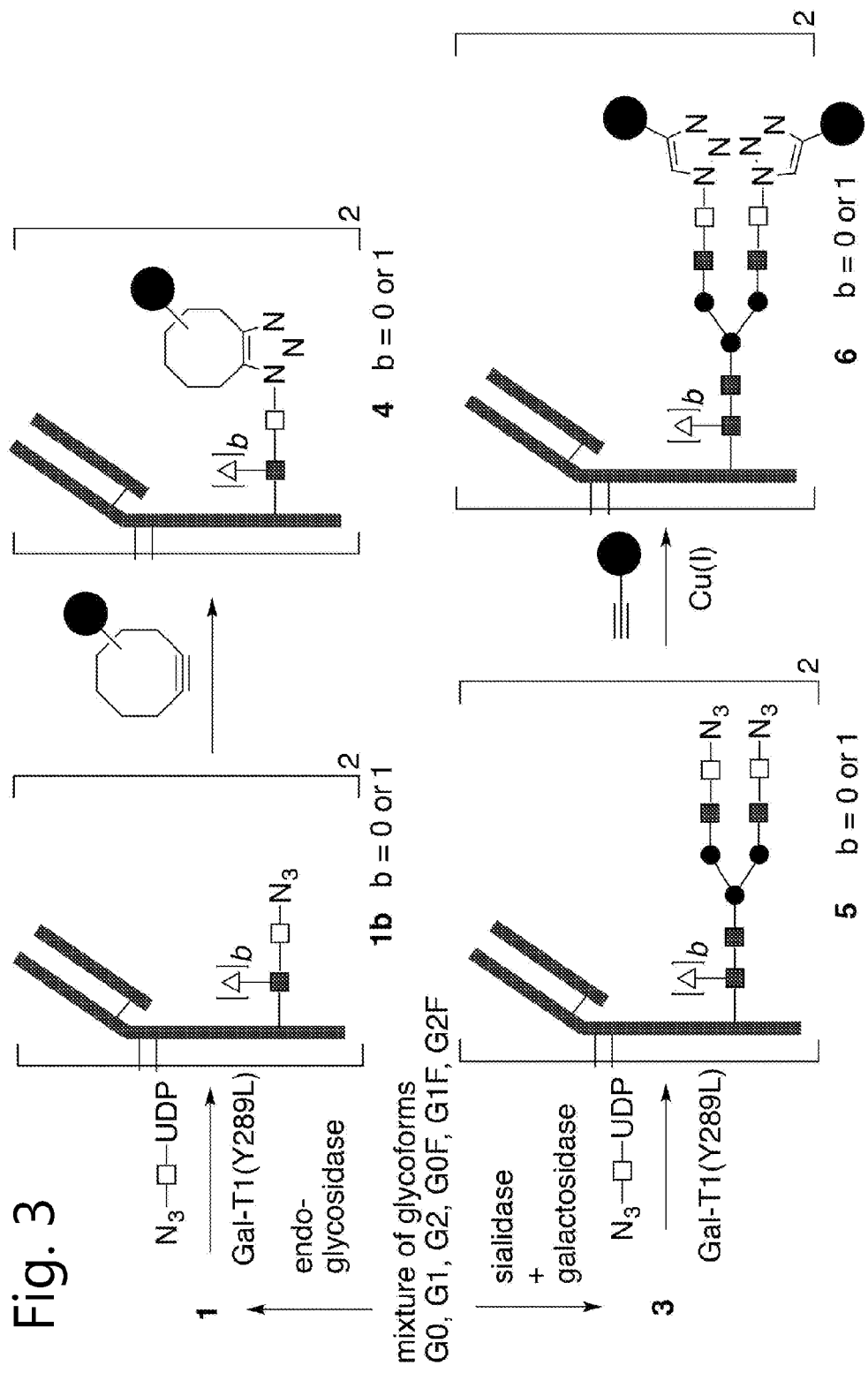
FIG. 3 shows the enzymatic conversion of the mixture of glycoforms of a mAb into GlcNAc-terminated mAb 1 or 3. Next, upon treatment of UDP-GalNAz in the presence of Gal-T1(Y289L), one or two GalNAz moieties per glycosylation site are introduced, leading to 1b or 5 respectively. The azide moieties in 1b and 5 serve as attachment point for functional group introduction by e.g. strain-promoted cycloaddition (1→44) or copper-catalyzed click reaction (5→6).

An additional advantage of the antibody-conjugates according to the invention is that the antibody-conjugates prepared according to the invention carry a highly polar hexasaccharide chain between the protein and the linker-toxin, as a result of transfer of an azidosugar onto the terminal GlcNAc of glycoform 2 (as depicted FIG. 2). A terminal GlcNAc can also be obtained by treatment of the mixture of glycoforms of the antibody by an endoglycosidase, leading to glycoform 1, but building on 1 leads to a short glycan chain of only two sugars between the antibody and the linker-drug conjugate, as graphically depicted for compound 4 in FIG. 3. The high polarity of the hexasaccharide chain may have a beneficial impact on the aggregation behavior of the antibody-conjugate, in particular when hydrophobic toxins are attached to the antibody.

Another advantage of the antibody-drug conjugates according to the invention is the fact that (not more than) two hydrophobic toxins may be attached by the process. An antibody containing terminal GlcNAc can also be obtained by trimming of complex glycans with a mixture of sialidase and galactosidase, thereby affording a glycoform with two terminal GlcNAc-unit, as structure 3 in FIG. 2. The latter glycoform 3 may also be converted in ADCs, but in that case the drug-to-antibody ratio will be around 4, as graphically depicted for compound 6 in FIG. 3. The advantage of having a DAR of 2 rather than 4 is that the presence of fewer hydrophobic payloads is likely to lead to reduced aggregation behavior of the antibody-drug conjugate.

Another advantage of the processes and antibodies according to the invention involves the reduction of waste in manufacturing, thereby enhancing companies' cost-of-goods.

Furthermore, when an azide-modified antibody according to the invention is coupled to a linker-conjugate comprising an alkynyl group, or when an alkyne-modified antibody according to the invention is coupled to a linker-conjugate comprising an azide moiety, via a cycloaddition reaction, the resulting triazoles are not susceptible to hydrolysis or other degradation pathways. When a ketone-modified antibody according to the invention is coupled to a linker-conjugate comprising a hydroxylamine or a hydrazine, the resulting oximes or hydrazones are also relatively inert at neutral conditions. When a thiol-modified antibody according to the invention is coupled to a linker-conjugate comprising a maleimide, the process is well-known in the art, highly robust and validated. Many maleimide-functionalized toxins have been described, because currently the preferred methodology for antibody-drug conjugation involves the combination of a cysteine mutant of a mAb (THIOmAb) and a maleimide derivative of a toxin. It is well known that such thiol-maleimide conjugates can be prepared with a highly beneficial stoichiometry of reagents (small excess of maleimide component). It is also well known that the resulting thiol-maleimide conjugates may have limited stability, but in case the thiol is present on fucose, the stability is significantly enhanced. When a thiol-modified antibody according to the invention is coupled to a linker-conjugate comprising a halogenated acetamide derivative of a toxin, the efficiency of the process may be somewhat compromised with respect to maleimide conjugation and more undesired alternative conjugation may take place (e.g. on lysine side chains), but the desired product is a irreversibly formed (highly stable) thio-ether conjugate. When a halogen-modified antibody according to the invention is coupled to a linker-conjugate comprising a derivative of a toxin containing a nucleophilic group (thiol, alcohol, amine), the resulting conjugate is a thio-ether, a regular ether or an amino-ether, all of which are formed irreversibly. In contrast to the use of halogenated acetemides for conjugation to proteins containing free thiols (as in THIOmAbs or in a thiofucose-containing mAb), the enzymatic incorporation of a halogenated sugar substrate is not compromised by competitive aspecific reaction with nucleophilic side chains of other amino acids (e.g. lysine). The lack of aspecific reactions also pertains to the subsequent conjugation step where in this case excess of a nucleophilic derivative of a functional group is applied to the halogenated mAb.

Additional advantages are thus the stability of antibody-conjugates according to the invention, as well as the straightforward and generally applicable process for the introduction of an azido group, a keto group, an alkynyl group, a thiol group, a halogen, a sulfonyloxy group, a halogenated acetamido group, a mercaptoacetamido group and a sulfonylated hydroxyacetamido group into an antibody.

Finally, an advantage preparing antibody conjugates by connecting via the glycan chain provides the opportunity to prepare a large number of isomers by means of engineering of glycomutants of the native antibody. Examples of different glycoforms (with R=glycan) of the native antibody are depicted in FIG. 18.

EXAMPLES

Modified Antibody, Antibody-Conjugate and Process for the Preparation Thereof

Examples

Synthesis

Example 1: Synthesis of BCN-Biotin Conjugate (33)

To a solution of 2,2'-(ethylenedioxy)bis(ethylamine) (11.78 mL, 80.5 mmol) in DCM (200 mL) was added BCN-OSu 23 (7.82 g, 26.8 mmol) in DCM (100 mL) dropwise over 3 h. After complete addition the mixture was stirred for 10 min followed by washing with saturated aqueous $NH_4Cl$ (3×200 mL). The organic layer was dried over $Na_2SO_4$, filtrated and concentrated in vacuo. Flash column chromatography (DCM:MeOH 99:1-93:7+1% $Et_3N$) gave product BCN-PEG$_2$-NH$_2$ (5.95 g, 54.7 mmol, 68%). $^1$H-NMR (300 MHz, CDCl$_3$) δ 5.38 (s, 1H), 4.13 (d, J=8.1 Hz, 2H), 3.59 (s, 4H), 3.56-3.50 (m, 4H), 3.35 (q, J=5.1 Hz, 2H), 2.88 (t, J=5.1 Hz, 2H), 2.32 (br s, 2H), 2.27-2.15 (m, 6H), 1.62-1.42 (m, 2H), 1.33 (qn, J=8.7 Hz, 1H), 0.97-0.85 (m, 2H). $^{13}$C-NMR (CDCl$_3$, 75 MHz) δ 156.4, 98.3, 68.7 (2C), 62.2, 45.5, 40.3, 40.2, 28.6, 20.9, 19.6, 17.3. HRMS (ESI+) calcd for $C_{17}H_{28}N_2NaO_4$ (M+Na$^+$) 347.1947, found 347.1952.

To a solution of BCN-PEG$_2$-NH$_2$ (0.80 g, 2.47 mmol) in DCM (25 mL) were added biotin-OSu (0.93 g, 2.71 mmol) and $Et_3N$ (0.86 mL, 6.16 mmol). The reaction mixture was stirred for 5 h and subsequent saturated aqueous NaHCO$_3$ (20 mL) was added. The organic layer was washed with saturated aqueous NaHCO$_3$ (2×20 mL), dried over $Na_2SO_4$, filtrated and concentrated under reduced pressure. Flash column chromatography (DCM:MeOH 99:1-92:8) afforded BCN biotin 25 (1.14 g, 2.1 mmol, 84%). $^1$H-NMR (400 MHz, CDCl$_3$): δ 6.57 (s, 1H), 6.44 (s, 1H), 5.48 (s, 1H), 5.37 (s, 1H), 4.52-4.48 (m, 1H), 4.33-4.30 (m, 1H), 4.16 (d, J=8 Hz, 2H), 3.62 (s, 4H), 3.57 (t, J=5.2 Hz, 4H), 3.45 (q, J=5.2 Hz, 2H), 3.40-3.36 (m, 2H), 3.17-3.12 (m, 1H), 2.92 (dd, J=8, 4.8 Hz, 1H), 2.72 (d, J=12.8 Hz, 1H), 2.33-2.18 (m, 8H), 1.88 (br s, 1H), 1.80-1.57 (m, 6H), 1.49-1.33 (m, 3H), 0.95 (t, J=9.6 Hz, 2H). $^{13}$C-NMR (CDCl$_3$, 75 MHz) δ 172.9, 163.6, 156.4, 98.3, 69.6, 61.3, 59.7, 55.2, 40.3, 40.0, 38.7, 35.5, 28.6, 27.8, 27.6, 25.1, 21.0, 19.7, 17.3. HRMS (ESI+) calcd for $C_{27}H_{43}N_4O_6S$ (M+H$^+$) 551.2903, found 551.2911.

Example 2: Synthesis of BCN-PEG$_2$-C(O)OSu Carbonate (35)

A solution of N,N'-disuccinimidyl carbonate (1.82 g, 7.11 mmol) in MeCN (50 mL) was prepared under argon. A solution of BCN-PEG$_2$-OH (1.0 g, 3.55 mmol) in MeCN (50 mL) was added dropwise over 3 h. After 1 h of additional stirring, the reaction mixture was poured out in a mixture of EtOAc/H$_2$O (150 mL/150 mL). The layers were separated and the aqueous layer was extracted with EtOAc (150 mL). The combined organic layers were dried (Na$_2$SO$_4$) and concentrated. The residue was purified via column chromatography and the desired product 35 was obtained as a colorless oil (0.79 g, 2.81 mmol, 79%). $^1$H NMR (CDCl$_3$, 400 MHz) δ (ppm) 5.19 (bs, 1H), 4.50-4.42 (m, 2H), 4.16 (d, J=8.0 Hz, 2H), 3.77-3.71 (m, 2H), 3.57 (t, J=5.1 Hz, 2H), 3.39 (dd, J=10.5, 5.4 Hz, 2H), 2.85 (s, 4H), 2.35-2.16 (m, 6H), 1.65-1.51 (m, 2H), 1.41-1.34 (m, 1H).

Example 3: Synthesis of BCN-vc-PABA-MMAF (36)

To a solution of Val-Cit-PAB-MMAF.TFA (17.9 mg, 14.3 μmol) in DMF (2 mL) was added BCN-PEG$_2$-C(O)OSu (17.9 mg, 14.3 μmol) (35) as a solution in DMF (0.78 mL) and triethylamine (6.0 μL). The product (7 mg, 5 μmol, 35%) was obtained after purification via reversed phase HPLC (C18, gradient H$_2$O/MeCN 1% AcOH). LRMS (HPLC, ESI+) calcd for $C_{24}H_{114}N_{11}O_{18}$ (M+H$^+$) 1444.83, found 1445.44.

Example 4: Synthesis of BCN-vc-PABA-β-Ala-Maytansinoid (37)

To a suspension of Val-Cit-PABA-β-alaninoyl-maytansinoid (commercially available from Concortis, San Diego, USA) (27 mg, 0.022 mmol) in MeCN (2 mL) was added triethylamine (9.2 μL, 6.7 mg, 0.066 mmol) and a solution of BCN-PEG$_2$-C(O)OSu carbonate 35 (9.2 mg, 0.022 mmol) in MeCN (1 mL). After 23 h, the mixture was poured out in a mixture of EtOAc (20 mL) and water (20 mL). After separation, the organic phase was dried (Na$_2$SO$_4$) and concentrated. After purification via column chromatography (EtOAc→MeOH/EtOAc 1/4) 22 mg (0.015 mmol, 70%) of the desired product was obtained. LRMS (ESI+) calcd for $C_{70}H_{97}ClN_{10}O_{20}$ (M+H$^+$) 1432.66, found 1434.64.

Conjugations

General Protocol for Mass Spectral Analysis of IgG

A solution of 50 μg (modified) IgG, 1 M Tris-HCl pH 8.0, 1 mM EDTA and 30 mM DTT with a total volume of approximately 70 μL was incubated for 20 minutes at 37° C. to reduce the disulfide bridges allowing to analyze both light and heavy chain. If present, azide-functionalities are reduced to amines under these conditions. Reduced samples were washed trice with milliQ using an Amicon Ultra-0.5, Ultracel-10 Membrane (Millipore) and concentrated to 10 μM (modified) IgG. The reduced IgG was analyzed by electrospray ionization time-of-flight (ESI-TOF) on a JEOL AccuTOF. Deconvoluted spectra were obtained using Magtran software.

Example 5: Expression of Trastuzumab in Presence of Swainsonine

Trastuzumab was transiently expressed in CHO K1 cells by Evitria (Zurich, Switzerland) in the presence of 10 and 25 μg/mL swainsonine (commercially available from Sigma-Aldrich), purified using protein A sepharose and analyzed by mass spectrometry. Both concentrations of swainsonine gave three major heavy chain products of trastuzumab 28 (see FIG. 6) which correspond to the trastuzumab heavy chain substituted with GlcNAc-Man$_5$-GlcNAc-GlcNAc (Fuc)-(c=d=0, 50712 Da, ±20% of total heavy chain product), Gal-GlcNAc-Man$_5$-GlcNAc-GlcNAc(Fuc)-(c=1, d=0, 50874 Da, ±35% of total heavy chain product), and Sial-Gal-GlcNAc-Man$_5$-GlcNAc-GlcNAc(Fuc)-(c=d=I, 51164

Da, ±35% of total heavy chain product). The MS profile of the glycoforms of 28 after expression in the presence of swainsonine are depicted in FIG. 13a.

Example 6: Trimming with Sialidase/Galactosidase to Give Trast-Man$_5$GlcNAc

The above described trastuzumab variants of 28 (10 mg/mL, see FIG. 6) were incubated with neuraminidase (0.5 mU/mg IgG) from *Vibrio cholerae* (commercially available from Sigma-aldrich) in 100 mM sodium acetate pH 6.0 and 2 mM CaCl$_2$ for 16 hrs, which led to complete removal of the sialic acid (two major heavy chain products of 50712 and 50874 Da which correspond to approximately 20 and 70% of the total heavy chain products). When the same reaction was performed in the presence of β(1,4)-galactosidase (3 mU/mg IgG) from *Streptococcus pneumoniae* (commercially available from Calbiochem), a single major heavy chain product 29 was observed corresponding to trastuzumab with a GlcNAc-Man$_5$-GlcNAc-GlcNAc(Fuc)-substituted heavy chain (c=d=0, 50712 Da, ±90% of total heavy chain product, and minor heavy chain products between 50700 and 50900 Da). The MS profile of the glycoforms of 29 after expression in the presence of swainsonine followed by trimming with sialidase and galactosidase are depicted in FIG. 13b.

Example 7: Transfer of GalNAz to Trast-Man$_5$GlcNAc Under the Action of GalT(Y289L)

Figures 14A, 14B:
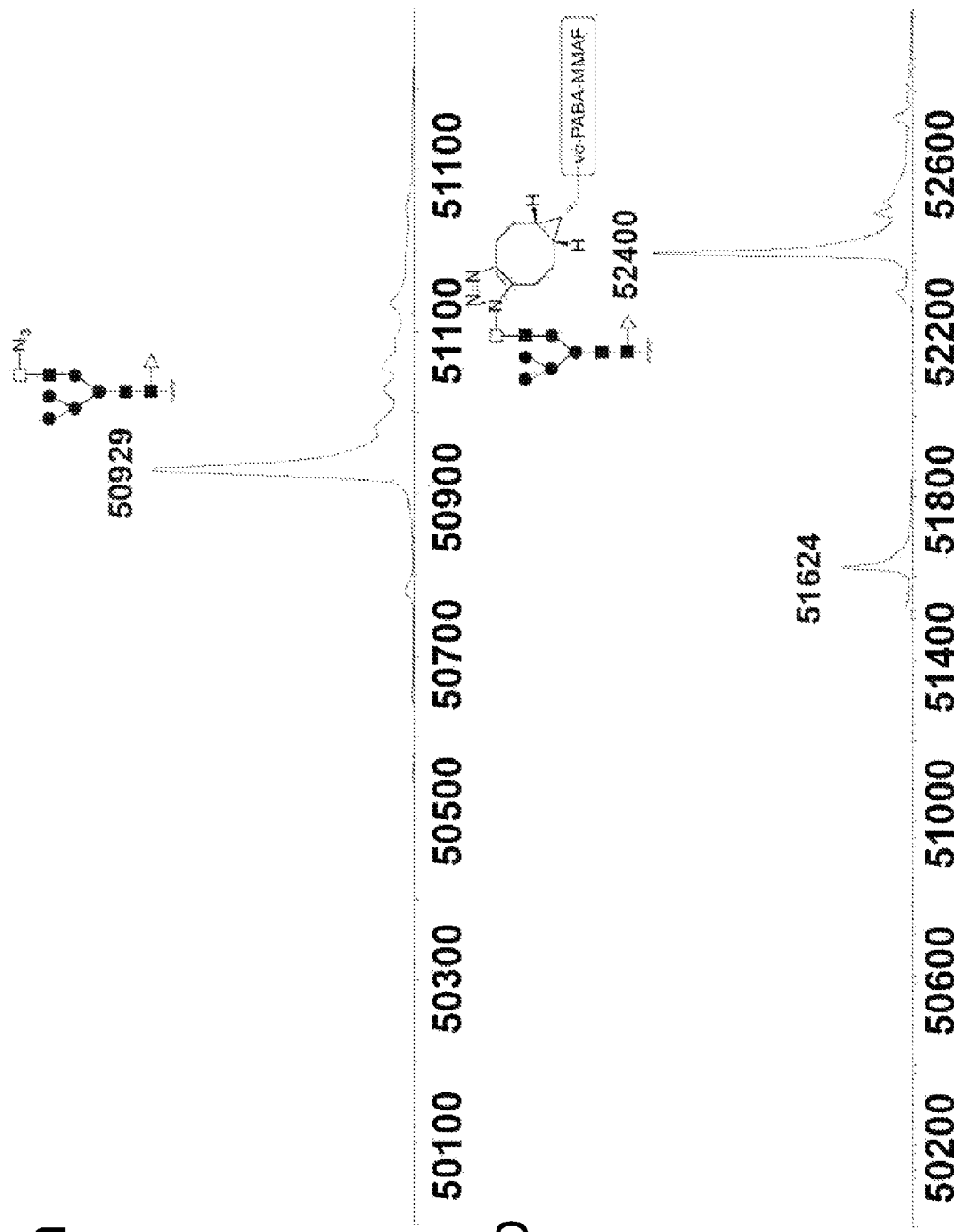
FIG. 14a shows the mass spectral profile of GalNAzGnM$_5$ trastuzumab, obtained by treatment of GnM$_5$ trastuzumab with UDP-GalNAz and Gal-T1(Y289L)
FIG. 14b shows the mass spectral profile of the product resulting from conjugation of GalNAzGnM$_5$ with BCN-vc-PABA-MMAF (36).

GlcNAc-Man$_5$-GlcNAc-GlcNAc(Fuc)-substituted trastuzumab (29, 10 mg/mL) was incubated with UDP-GalNAz (0.5 mM) (commercially available from Glycohub, Inc) and β(1,4)-Gal-T1(Y289L) (expressed according to the reported procedure by Qasba et al. *J. Biol. Chem.* 2002, 277, 20833-20839) (0.1 mg/mL) in 10 mM MnCl$_2$ and 25 mM Tris-HCl pH 8.0 for 16 hours at 30° C., which led to complete conversion into GalNAz-GlcNAc-Man$_5$-GlcNAc-GlcNAc (Fuc)-substituted trastuzumab 31 as depicted in FIG. 7 (major heavy chain product of 50929 Da, ±90% of the total heavy chain products, and minor heavy chain products between 50900 and 51150). The MS profile of the main glycoform 31 after transfer of GalNAz is depicted in FIG. 14a.

Example 8: Conjugation of Trast-Man$_5$GlcNAc-GalNAz with 36

Incubation of GalNAz-GlcNAc-Man$_5$-GlcNAc-GlcNAc (Fuc)-substituted trastuzumab (31 as depicted in FIG. 7, 10 mg/mL) with BCN-vc-MIVIAF 36 (4 eq) in PBS for approximately 16 h led to complete conversion into the corresponding ADC (heavy chain products between 52200 and 52733 Da with major peak of 52400 Da, ±90% of total heavy chain, and a minor peaks at 51624 Da corresponding to the product of which the PABA linker has fragmentated during mass spectrometry analysis, ±10% of total heavy chain). The MS profile of the main glycoform after transfer of GalNAz (31) and reaction with 36 is depicted in FIG. 14b.

Example 9: Conjugation of Trast-Man$_5$GlcNAc-GalNAz with 37

Incubation of GalNAz-GlcNAc-Man$_5$-GlcNAc-GlcNAc (Fuc)-substituted trastuzumab (31, 10 mg/mL) with BCN-vc-PABA-maytansinoid 37 (5×4 eq) in PBS for approximately 1 week led to approximately 95% conversion into the corresponding ADC (heavy chain products between 52300 and 52735 Da with major peak of 52389 Da, ±95% of total heavy chain, and two minor peaks at 50928 and 51623 Da corresponding to starting material and the product of which the PABA linker has fragmentated during mass spectrometry analysis, ±5% of total heavy chain).

Example 10. Expression and Isolation of GlcNAc-T1 (GnT-I)

The sequence coding for amino acids 31 to 416 of human mannosyl (α-1,3-)-glycoprotein α-(1,2)-N-acetylglucosaminyltransferase (N-acetylglucosaminyl-transferase I, GnT-I) was PCR amplified from human placenta cDNA using the primers 5'-agctCATATGcgcccagcacctgg (SEQ ID NO: 25) and 5'-agctGGATCCctaattccagctag gatcatagccctc (SEQ ID NO: 26) and cloned into the NdeI and BamHI sites of pET16B. GnT-I was expressed and isolated according to the reported procedure by Tolbert et al. *Advanced Synthesis & Catalysis* 2008, 350, 1689-1695).

Example 11: Transfer of GlcNac to CalB Man$_5$ Under the Action of GnT-I

Figure 11:
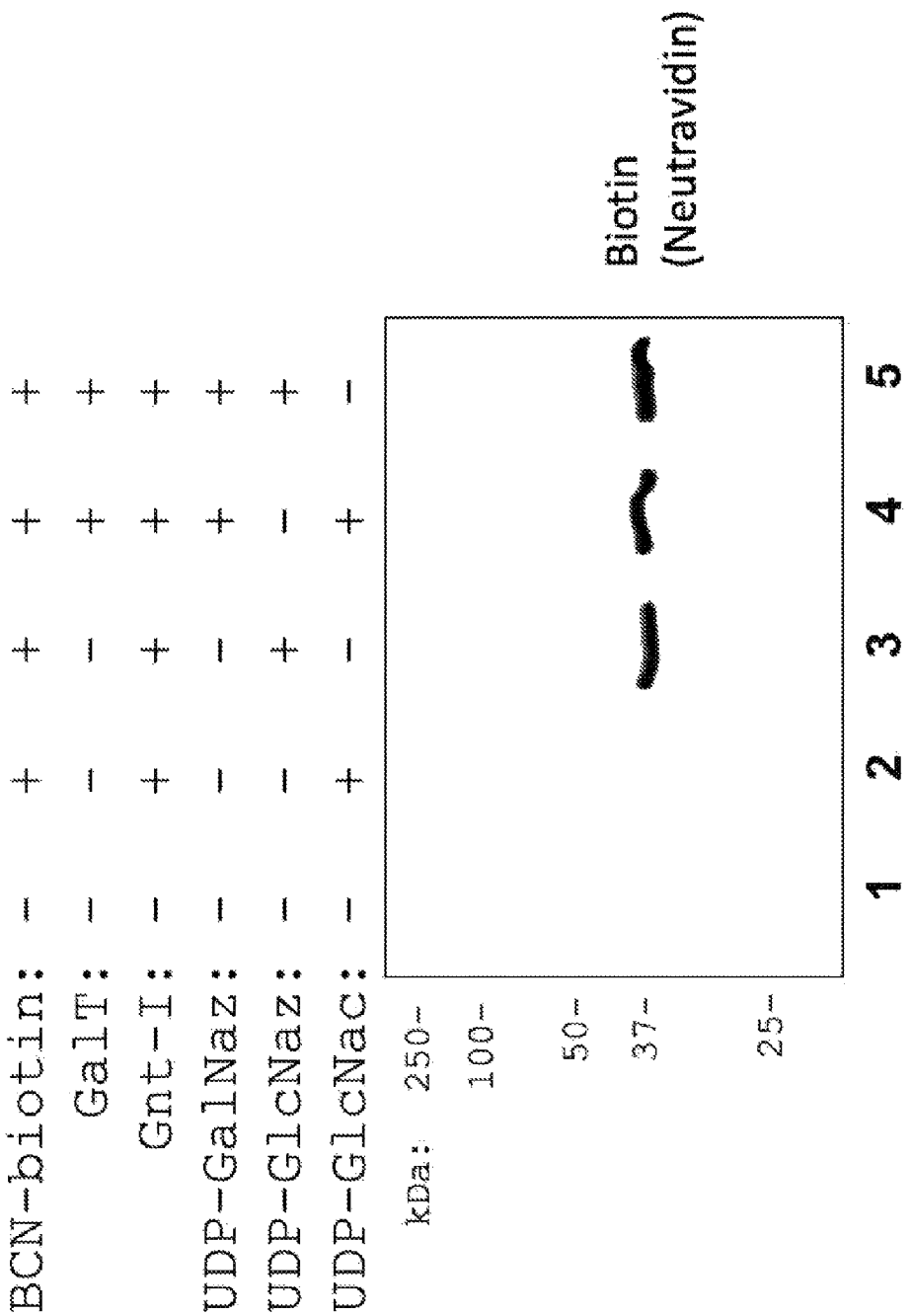
FIG. 11 shows the Western blot of conversion of a Man$_5$-terminated protein (CalB) into a GalNAz-GlcNAc-Man$_5$-protein, and subsequent treatment with BCN-biotin 33.
Figure 12:
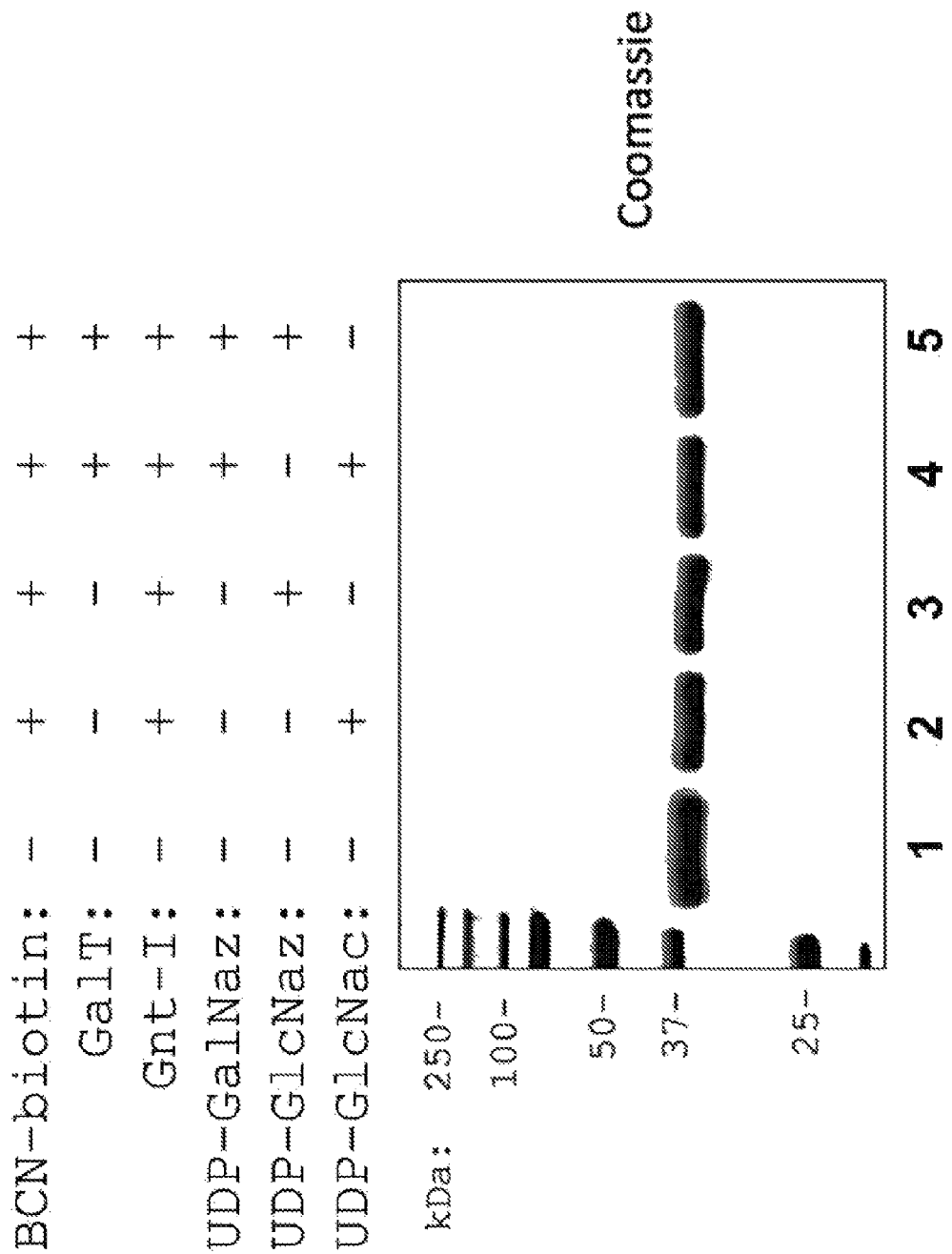
FIG. 12 shows the control gel of conversion of a Man$_5$-terminated protein (CalB) into a GalNAz-GlcNAc-Man$_5$-protein, and subsequent treatment with BCN-biotin 33.

Candida Antarctica lipase B with Man$_5$-glycan(CalB-Man$_5$) (27.5 µL, 18.16 mg/mL) was incubated with UDP-GlcNac (commercially available from Sigma Aldrich) (25 µL, 10 mM) and GnT-I (50 µL, 0.5 mg/mL) in 10 mM MnCl$_2$ and 25 mM Tris-HCl pH 7.5 for 16 hours at 37° C. The excess of UDP-GlcNac was removed by spinfilter purification, BCN-biotin 33 (final concentration of 1 mM) was added and the reaction was incubated overnight at room temperature. Reaction products were separated by SDS-PAGE followed by coomassie staining to detect the total amount of CalB (FIG. 12, lane 2) and SDS-PAGE followed by western blotting stained with neutravidin-IRDye800 to detect biotin-conjugated CalB (FIG. 11, lane 2).

Example 12: Transfer of GlcNaz to CalB-Man$_5$ Under the Action of GnT-I

CalB-Man$_5$ (5.5 µL, 18.16 mg/mL) was incubated with UDP-GlcNaz (commercially available from AccendaTech) (5 µL, 10 mM) and GnT-I (10 µL, 0.5 mg/mL) in 10 mM MnCl$_2$ and 25 mM Tris-HCl pH 7.5 for 16 hours at 37° C. The excess of UDP-GlcNaz was removed by spinfilter purification, BCN-biotin 33 (final concentration of 1 mM) was added and the reaction was incubated overnight at room temperature. Reaction products were separated by SDS-PAGE followed by coomassie staining to detect the total amount of CalB-Man$_5$ (FIG. 12, lane 3) and SDS-PAGE followed by western blotting stained with neutravidin-IRDye800 to detect biotin-conjugated CalB (FIG. 11, lane 3). Biotin-conjugated CalB is detected for CalB-Man$_5$ incubated with GnT-I and UDP-GlcNAz (FIG. 11, lane 3), but not for CalB-Man$_5$ incubated with GnT-I and UDP-GlcNac (FIG. 11, lane 2). This proves that CalB-Man$_5$ was successfully converted into CalB-Man$_5$-GlcNaz, and that the azide-handle can be used for conjugation to BCN-biotin.

Example 13: Simultaneous Transfer of GlcNAc and GalNAz to CalB Man$_5$ Under the Action of GnT-I and GalT(Y289L)

CalB-Man$_5$ (5.5 µL, 18.16 mg/mL) was incubated with UDP-GlcNac (5 µL, 10 mM), GnT-I (10 µL, 0.5 mg/mL), UDP-GalNaz (1 μL, 10 mM), β(1,4)-Gal-T1(Y289L) (1 μL, 2 mg/mL) in 10 mM $MnCl_2$ and 25 mM Tris-HCl pH 7.5 for 16 hours at 37° C. The excess of UDP-sugars was removed by spinfilter purification, BCN-biotin 33 (final concentration of 1 mM) was added and the reaction was incubated overnight at room temperature. Reaction products were separated by SDS-PAGE followed by coomassie staining to detect the total amount of CalB (FIG. 11, lane 4) and SDS-PAGE followed by western blotting stained with neutravidin-IRDye800 to detect biotin-conjugated CalB (FIG. 11, lane 4). Biotin-conjugated CalB is detected for CalB-$Man_5$ incubated with GnT-I, UDP-GlcNac, β(1,4)-Gal-T1 (Y289L) and UDP-GalNAz (FIG. 11, upper panel, lane 4), but not for CalB-$Man_5$ incubated with only GnT-I and UDP-GlcNac (FIG. 11, lane 2). This proves that CalB-$Man_5$ was successfully converted into CalB-$Man_5$-GlcNac followed by its conversion into CalB-$Man_5$-GlcNac-GalNaz, and that the azide-handle can be used for conjugation to BCN-biotin.

Example 14: Transfer of GlcNaz and GalNAz to CalB-$Man_5$ Under the Action of GnT-I and GalT(Y289L)

CalB-$Man_5$ (5.5 μL, 18.16 mg/mL) was incubated with UDP-GlcNaz (5 μL, 10 mM), GnT-I (10 μL, 0.5 mg/mL), UDP-GalNaz (1 μL, 10 mM), β(1,4)-Gal-T1(Y289L) (1 μL, 2 mg/mL) in 10 mM $MnCl_2$ and 25 mM Tris-HCl pH 7.5 for 16 hours at 37° C. The excess of UDP-sugars was removed by spinfilter purification, BCN-biotin 33 (final concentration of 1 mM) was added and the reaction was incubated overnight at room temperature. Reaction products were separated by SDS-PAGE followed by coomassie staining to detect the total amount of CalB (FIG. 11, lane 5) and SDS-PAGE followed by western blotting stained with neutravidin-IRDye800 to detect biotin-conjugated CalB (FIG. 11, upper panel, lane 5). Biotin-conjugated CalB is detected for CalB-$Man_5$ incubated with GnT-I, UDP-GlcNaz, β(1,4)-Gal-T1(Y289L) and UDP-GalNaz (FIG. 11, lane 5), indicating that CalB-$Man_5$ is successfully converted into CalB-$Man_5$-GlcNaz and possibly CalB-$Man_5$-GlcNaz-GalNaz, and that one or two of the azide-handles can be used for conjugation to BCN-biotin.

Example 15: In Vitro Efficacy

SK-Br-3 (Her2+), SK-OV-3 (Her2+) and MDA-MB-231 (Her2−) cells were plated in 96-wells plates (5000 cells/well) in RPMI 1640 GlutaMAX (Invitrogen) supplemented with 10% fetal calf serum (FCS) (Invitrogen, 200 μL/well) and incubated overnight at 37° C. and 5% $CO_2$. A three-fold dilution series (ranging from ±0.002 to 100 nM) of the sterile-filtered compounds was prepared in RPMI 1640 GlutaMAX supplemented with 10% FCS. After removal of the culture medium, the concentration series were added in quadruplo and incubated for three days at 37° C. and 5% $CO_2$. The culture medium was replaced by 0.01 mg/mL resazurin (Sigma Aldrich) in RPMI 1640 GlutaMAX supplemented with 10% FCS. After 4 to 6 hours at 37° C. and 5% $CO_2$ fluorescence was detected with a fluorescence plate reader (Tecan Infinite 200) at 540 nm excitation and 590 nm emission. The relative fluorescent units (RFU) were normalized to cell viability percentage by setting wells without cells at 0% viability and wells with lowest dose of compound at 100% viability. For each conditions the average cell viability percentage±sem is shown.

Figure 15:
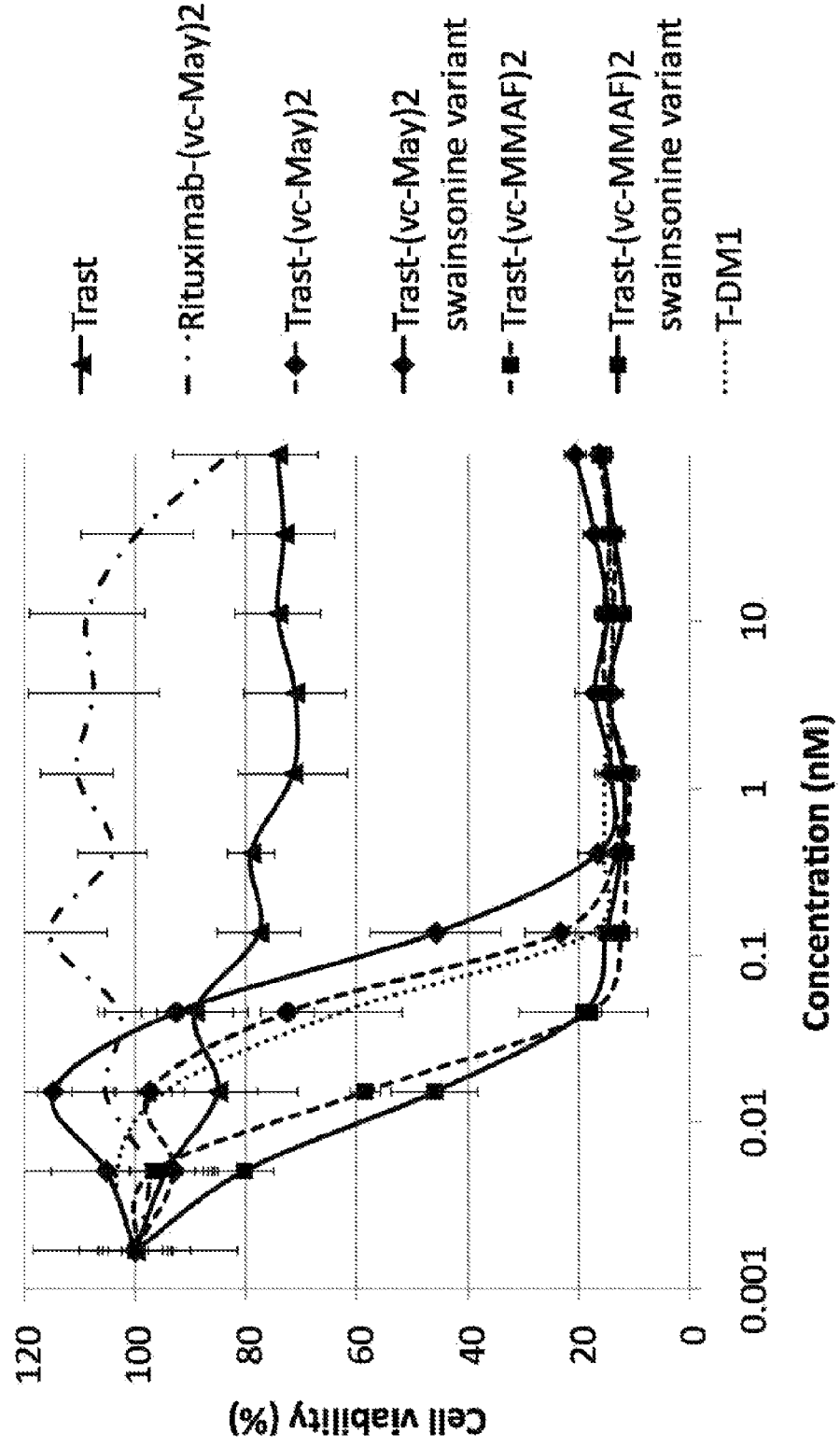
FIG. 15 shows the in vitro cytotoxicity of a range of ADCs against SK-Br-3 cell line.
Figure 16:
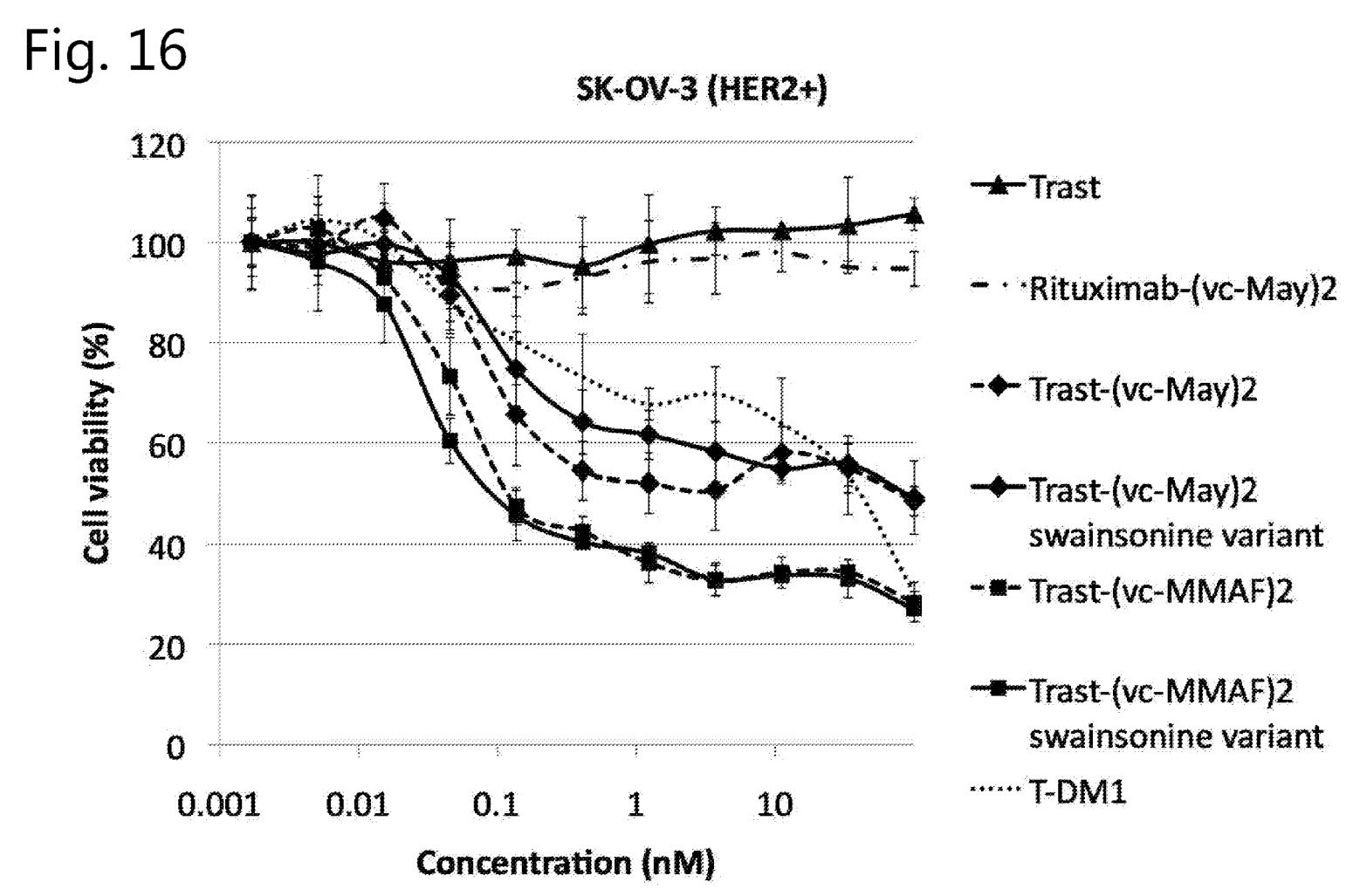
Figure 17:
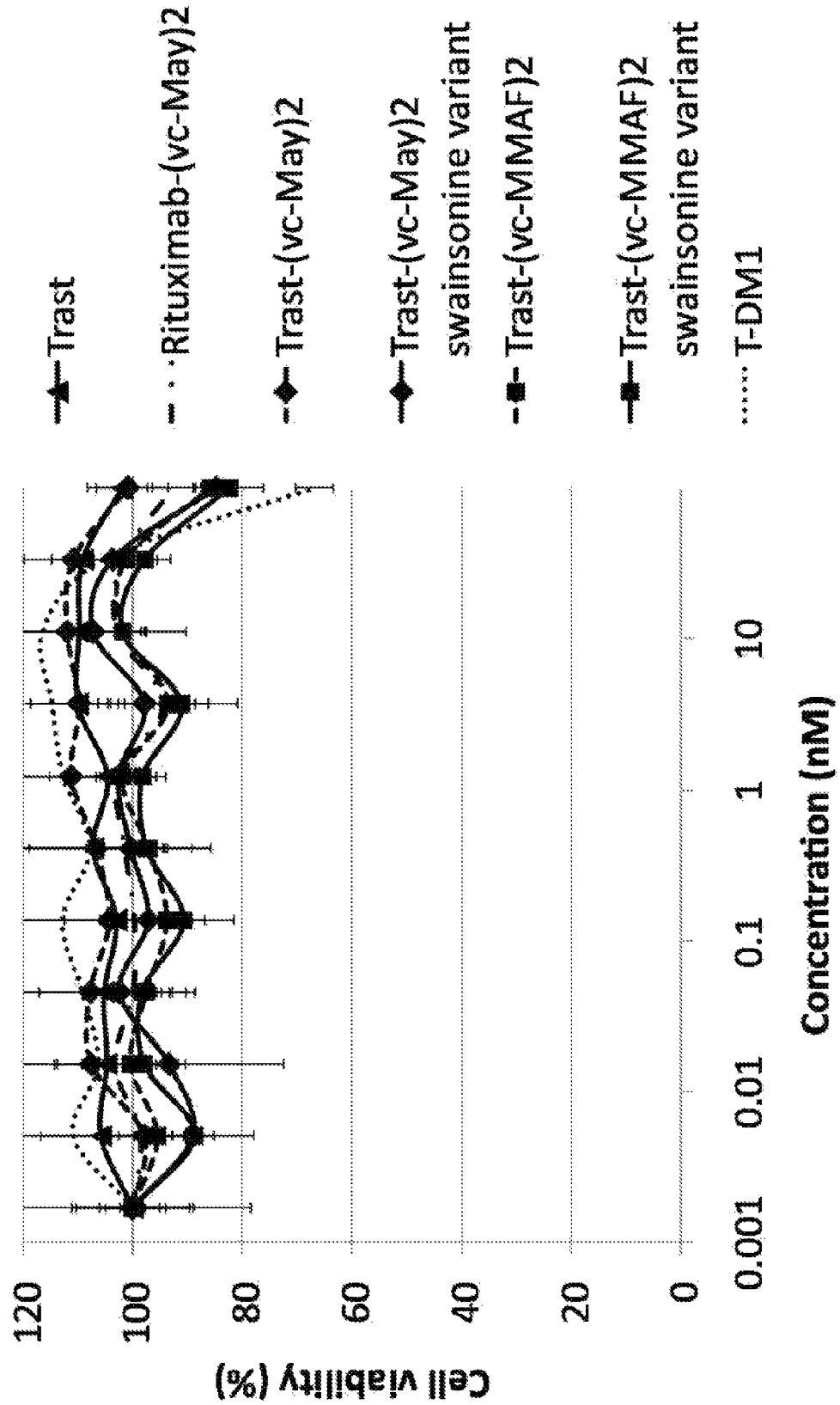
FIG. 17 shows the in vitro cytotoxicity of a range of ADCs against MDA-MB-231 cell line (negative control).

The in vitro cytotoxicity of the above described ADC's were compared to trastuzumab-(vc-PABA-MMAF)$_2$ (36), trastuzumab-(vc-PABA-maytansinoid)$_2$ (37). T-DM1 was used as a positive control and trastuzumab and rituximab-(vc-PABA-maytansinoid)$_2$ (37) as negative controls (FIGS. 15-17). All trastuzumab-based ADC's affect the viability of the Her2-positive cell lines SK-Br-3 and SK-OV-3, but not of the Her2-negative cell line MDA-MB-231, which shows that these ADC's specifically target Her2-positive cells. In the Her2-negative cell line MDA-MB-231, only T-DM1 shows a slight decrease in cell viability at the highest concentration (100 nM). The extended glycan-linker does not significantly affect the in vitro toxicity (compare for example trastuzumab-(vc-PABA-MMAF)$_2$ with the swainsonine variant of trastuzumab-(vc-PABA-MMAF)$_2$.

Graphs for the above described in vitro assays are provided in FIG. 15 (SK-Br-3), FIG. 16 (SK-OV-3) and FIG. 17 (MDA-MB-231).

Example 16: Cloning and Expression of GalT Mutants Y289N, Y289F, Y289M, Y289V, Y289A, Y289G and Y289I The GalT mutant genes were amplified from a construct containing the sequence encoding the catalytic domain of GalT consisting of 130-402 aa residues, by the overlap extension PCR method. The wild type enzyme is represented by SEQ ID NO: 17. For Y289N mutant (represented by SEQ ID NO: 18), the first DNA fragment was amplified with a pair of primers: Oligo38_GalT_External_Fw (CAG CGA CAT ATG TCG CTG ACC GCA TGC CCT GAG GAG TCC represented by SEQ ID NO: 1) and Oligo19_GalT_Y289N_Rw (GAC ACC TCC AAA GTT CTG CAC GTA AGG TAG GCT AAA represented by SEQ ID NO: 2). The NdeI restriction site is underlined, while the mutation site is highlighted in bold. The second fragment was amplified with a pair of primers: Oligo29_GalT_External_Rw (CTG ATG GAT GGA TCC CTA GCT CGG CGT CCC GAT GTC CAC represented by SEQ ID NO: 3) and Oligo18_GalT_Y289N_Fw (CCT TAC GTG CAG AAC TTT GGA GGT GTC TCT GCT CTA represented by SEQ ID NO: 4). The BamHI restriction site is underlined, while the mutation site is highlighted in bold. The two fragments generated in the first round of PCR were fused in the second round using Oligo38_GalT_External_Fw and Oligo29_GalT_External_Rw primers. After digestion with NdeI and BamHI. This fragment was ligated into the pET16b vector cleaved with the same restriction enzymes. The newly constructed expression vector contained the gene encoding Y289N mutant and the sequence encoding for the His-tag from pET16b vector, which was confirmed by DNA sequencing results. For the construction of Y289F (represented by SEQ ID NO: 19), Y289M (represented by SEQ ID NO: 20), Y289I (represented by SEQ ID NO: 21), Y289V (represented by SEQ ID NO: 22), Y289A (represented by SEQ ID NO: 23) and Y289G (represented by SEQ ID NO: 24) mutants the same procedure was used, with the mutation sites changed to TTT, ATG, ATT, GTG, GCG or GGC triplets encoding for phenylalanine, methionine, isoleucine, valine, alanine or glycine, respectively. More specifically, for the construction of Y289F the first DNA fragment was amplified with a pair of primers defined herein as SEQ ID NO: 1 and SEQ ID NO: 5 and the second fragment was amplified with a pair of primers defined herein as SEQ ID NO: 3 and SEQ ID NO: 6 (be referred to Table 1 for the related sequences). Furthermore, for the construction of Y289M the first DNA fragment was amplified with a pair of primers defined herein as SEQ ID NO: 1 and SEQ ID NO: 7 and the second fragment was amplified with a pair of primers defined herein as SEQ ID NO: 3 and SEQ ID NO: 8. For the construction of Y289I the first DNA fragment was amplified with a pair of primers defined herein as SEQ ID NO: 1 and SEQ ID NO: 9 and the second fragment was amplified with a pair of primers defined herein as SEQ ID NO: 3 and SEQ ID NO: 10. For the construction of Y289V the first DNA fragment was amplified with a pair of primers defined herein as SEQ ID NO: 1 and SEQ ID NO: 11 and the second fragment was amplified with a pair of primers defined herein as SEQ ID NO: 3 and SEQ ID NO: 12. for the construction of Y289A the first DNA fragment was amplified with a pair of primers defined herein as SEQ ID NO: 1 and SEQ ID NO: 13 and the second fragment was amplified with a pair of primers defined herein as SEQ ID NO: 3 and SEQ ID NO: 14. For the construction of Y289G the first DNA fragment was amplified with a pair of primers defined herein as SEQ ID NO: 1 and SEQ ID NO: 15 and the second fragment was amplified with a pair of primers defined herein as SEQ ID NO: 3 and SEQ ID NO: 16 (be referred to Table 1 for the related sequences).

GalT mutants were expressed, isolated and refolded from inclusion bodies according to the reported procedure by Qasba et al. (*Prot. Expr. Pur.* 2003, 30, 219-229). After refolding, the precipitate was removed and the soluble and folded protein was isolated using a Ni-NTA column (His-Trap excel 1 mL column, GE Healthcare). After elution with 25 mM Tris-HCl pH 8.0, 300 mM NaCl and 200 mM imidazole, the protein was dialyzed against 25 mM Tris-HCl pH 8.0 and concentrated to 2 mg/mL using a spinfilter (Amicon Ultra-15 Centrifugal Filter Unit with Ultracel-10 membrane, Merck Millipore).

TABLE 1

Sequence identification of the primers used

| SEQ ID NO | Nucleotide sequence |
|---|---|
| SEQ ID NO: 1 | CAG CGA CAT ATG TCG CTG ACC GCA TGC CCT GAG GAG TCC |
| SEQ ID NO: 2 | GAC ACC TCC AAA GTT CTG CAC GTA AGG TAG GCT AAA |
| SEQ ID NO: 3 | CTG ATG GAT GGA TCC CTA GCT CGG CGT CCC GAT GTC CAC |
| SEQ ID NO: 4 | CCT TAC GTG CAG AAC TTT GGA GGT GTC TCT GCT CTA |
| SEQ ID NO: 5 | GAC ACC TCC AAA AAA CTG CAC GTA AGG TAG GCT AAA |
| SEQ ID NO: 6 | CCT TAC GTG CAG TTT TTT GGA GGT GTC TCT GCT CTA |
| SEQ ID NO: 7 | GAC ACC TCC AAA CAT CTG CAC GTA AGG TAG GCT AAA |
| SEQ ID NO: 8 | CCT TAC GTG CAG ATG TTT GGA GGT GTC TCT GCT CTA |
| SEQ ID NO: 9 | GAC ACC TCC AAA AAT CTG CAC GTA AGG TAG GCT AAA |
| SEQ ID NO: 10 | CCT TAC GTG CAG ATT TTT GGA GGT GTC TCT GCT CTA |
| SEQ ID NO: 11 | GAC ACC TCC AAA CAC CTG CAC GTA AGG TAG GCT AAA |

TABLE 1-continued

Sequence identification of the primers used

| SEQ ID NO | Nucleotide sequence |
|---|---|
| SEQ ID NO: 12 | CCT TAC GTG CAG GTG TTT GGA GGT GTC TCT GCT CTA |
| SEQ ID NO: 13 | GAC ACC TCC AAA CGC CTG CAC GTA AGG TAG GCT AAA |
| SEQ ID NO: 14 | CCT TAC GTG CAG GCG TTT GGA GGT GTC TCT GCT CTA |
| SEQ ID NO: 15 | GAC ACC TCC AAA GCC CTG CAC GTA AGG TAG GCT AAA |
| SEQ ID NO: 16 | CCT TAC GTG CAG GGC TTT GGA GGT GTC TCT GCT CTA |

Example 17: Expression of Trastuzumab Mutants in Presence of Swainsonine

Three mutants of trastuzumab (trastuzumab-HC-N300Q-LC-R18N, trastuzumab-HC-N300Q-V366T and trastuzumab-HC-L177N-N300Q) were transiently expressed in CHO K1 cells by Evitria (Zurich, Switzerland) in the presence of 10 μg/mL swainsonine (commercially available from Sigma-Aldrich), purified using protein A sepharose and analyzed by mass spectrometry. Trastuzumab-HC-N300Q-LC-R18N showed one major heavy chain product which corresponds to the nonglycosylated N300Q heavy chain without C-terminal lysine (observed mass of 49163 Da, calculated mass of 49171 Da), and two major light chain product which correspond to the R18N light chain substituted with Gal-GlcNAc-Man$_5$-GlcNAc-GlcNAc(Fuc)- (observed mass of 25126 Da, calculated mass of 25131 Da, ±20% of total light chain product), and Sial-Gal-GlcNAc-Man$_5$-GlcNAc-GlcNAc(Fuc)- (observed mass of 25418 Da, calculated mass of 25422 Da, ±80% of total light chain product). Trastuzumab-HC-N300Q-V366T showed three major heavy chain products which corresponds to the N300Q-V366T heavy chain without C-terminal lysine and substituted with Gal-GlcNAc-Man$_5$-GlcNAc-GlcNAc(Fuc)- (observed mass of 50895 Da, calculated mass of 50902 Da, ±10% of total heavy chain product), the N300Q-V366T heavy chain without C-terminal lysine and substituted with Sial-Gal-GlcNAc-Man$_5$-GlcNAc-GlcNAc(Fuc)- (observed mass of 51185 Da, calculated mass of 51193 Da, ±70% of total heavy chain product), and the N300Q-V366T heavy chain with C-terminal lysine and substituted with Sial-Gal-GlcNAc-Man$_5$-GlcNAc-GlcNAc(Fuc)- (observed mass of 51313 Da, calculated mass of 51321 Da, ±10% of total heavy chain product). Trastuzumab-HC-L177N-N300Q showed two major heavy chain products which corresponds to the L177N-N300Q heavy chain without C-terminal lysine and substituted with Gal-GlcNAc-Man$_5$-GlcNAc$_2$- (observed mass of 50745 Da, calculated mass of 50755 Da, ±10% of total heavy chain product), and Sial-Gal-GlcNAc-Man$_5$-GlcNAc$_2$- (observed mass of 51037 Da, calculated mass of 51046 Da, ±70% of total heavy chain product).

Example 18: Trimming of Trastuzumab Glycomutants with Sialidase/Galactosidase to Give Trast-Man$_5$GlcNAc The above described trastuzumab mutants (as compounds 28 from FIG. 6, 10 mg/mL) were incubated with neuraminidase (2.5 mU/mg IgG) from *Vibrio cholerae* (commercially available from Sigma-aldrich) and β(1,4)-galactosidase (80 U/mg IgG) from *Bacteroides fragilis* (commercially available from New England Biolabs) in 100 mM sodium acetate pH 6.0 and 2 mM CaCl$_2$ for 16 hrs. at 37° C., which led to complete removal of the sialic acid and the galactose for all three mutants. Trastuzumab-HC-N300Q-LC-R18N showed one major light chain product which corresponds to the R18N light chain substituted with GlcNAc-Man$_5$-GlcNAc-GlcNAc(Fuc)- (observed mass of 24964 Da, calculated mass of 24968 Da). Trastuzumab-HC-N300Q-V366T showed one major heavy chain product which corresponds to the N300Q-V366T heavy chain substituted with GlcNAc-Man$_5$-GlcNAc-GlcNAc(Fuc)- (observed mass of 50732 Da, calculated mass of 50740 Da). Trastuzumab-HC-L177N-N300Q showed one major heavy chain product which Example 20: Synthesis of BCN-dPEG$_4$-C(O)OSu To a solution of amino-dPEG$_4$-acid (1.23 g, 4.23 mmol) in anhydrous DMF (30 mL) was subsequently added BCN hydroxysuccinimide carbonate (1.02 g, 3.85 mmol) and triethylamine (1.60 mL, 11.53 mmol). The reaction mixture was stirred for 3 h at rt, after which EDCI.HCl (0.884 g, 4.61 mmol) and NHS (88 mg, 0.77 mmol) were added. The resulting solution was stirred overnight at rt and poured into 100 mL NaHCO$_3$ (sat.) and 150 mL EtOAc. The layers were separated and the organic phase was washed with sat. NaHCO$_3$ (90 mL) and H$_2$O (75 mL). The organic phase was dried (Na$_2$SO$_4$), filtered and concentrated in vacuo. Gradient flash chromatography (MeCN MeCN:H$_2$O 30:1) afforded product BCN-dPEG$_4$-C(O)OSu as a colorless oil (800 mg, 1.48 mmol, 40%).

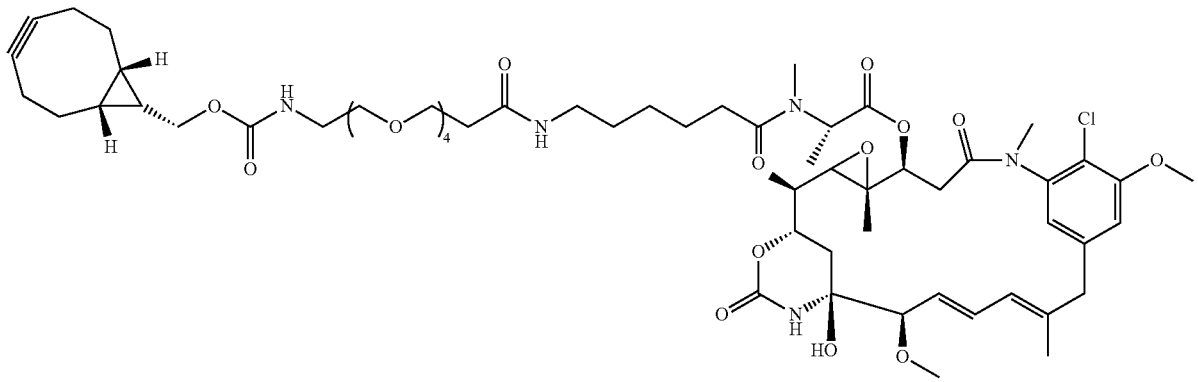

corresponds to the L177N-N300Q heavy chain substituted with GlcNAc-Man$_5$-GlcNAc$_2$- (observed mass of 50585 Da, calculated mass of 50593 Da).

Example 19: Transfer of GalNAz to Trastuzumab Mutants, Glycoform Man$_5$GlcNAc, Under the Action of GalT(Y289L)

The above described trastuzumab mutants (29, 10 mg/mL) were incubated with UDP-GalNAz (1 mM) and β(1,4)-Gal-T1(Y289L) (0.1 mg/mL) in 10 mM MnCl$_2$ and 25 mM Tris-HCl pH 7.5 for 16 hours at 30° C., which led to complete conversion into GalNAz-GlcNAc-Man$_5$-GlcNAc-GlcNAc(Fuc)- or GalNAz-GlcNAc-Man$_5$-GlcNAc$_2$-substituted trastuzumab 31. Trastuzumab-HC-N300Q-LC-R18N showed two major light chain products which correspond to the R18N light chain substituted with GalNAzGlcNAc-Man$_5$-GlcNAc-GlcNAc(Fuc)- and its reduced form (observed mass of 25209 and 25183 Da, calculated mass of 25213 and 25187 Da). The latter product was formed by reduction of the azide during the sample preparation for mass spectral analysis. Trastuzumab-HC-N300Q-V366T showed two major heavy chain products which correspond to the N300Q-V366T heavy chain substituted with GalNAzGlcNAc-Man$_5$-GlcNAc-GlcNAc(Fuc)- and its reduced form (observed mass of 50976 and 50952 Da, calculated mass of 50984 and 50958 Da). Trastuzumab-HC-L177N-N300Q showed two major heavy chain products which correspond to the L177N-N300Q heavy chain substituted with GalNAzGlcNAc-Man$_5$-GlcNAc$_2$- and its reduced form (observed mass of 50829 and 50806 Da, calculated mass of 50837 and 50811 Da).

Example 21: Synthesis of BCN-dPEG$_4$-C(O)-Ahx-Maytansin

A solution of BCN-PEG$_4$-C(O)OSu (7.1 mg, 0.013 mmol) and Et$_3$N (9.1 μL, 6.6 mg, 65.5 μmol) in 1 mL DMF was added to H-Ahx-maytansin.TFA (10 mg, 0.011 mmol), commercially obtainable from Concortis. The reaction was stirred for 20 h at rt and subsequently concentrated under reduced pressure. The residue was purified via reversed phase (C18) HPLC chromatography (30→90% MeCN (1% AcOH) in H$_2$O (1% AcOH). Product BCN-dPEG$_4$-C(O)-Ahx-maytansin was obtained as a colorless liquid (8.9 mg, 7.5 μmol, 68%). LRMS (ESI$^+$) m/z calcd for C$_{60}$H$_{87}$ClN$_5$O$_{16}$ (M$^+$–H$_2$O)=1168.58; found 1168.87.

Example 20: Conjugation of Trastuzumab Mutant, Glycoform GlcNAcMan$_5$GlcNAc, with BCN-dPEG$_4$-C(O)-Ahx-Maytansin Incubation of the above described trastuzumab mutant, glycoform GlcNAcMan$_5$GlcNAc (31, 15 mg/mL) with BCN-dPEG$_4$-C(O)-Ahx-maytansin (10 eq) in PBS for approximately 16 h led to complete conversion into the corresponding ADCs. Trastuzumab-HC-N300Q-LC-R18N showed one major light chain product which corresponds to the R18N light chain substituted with GalNAzGlcNAc-Man$_5$-GlcNAc-GlcNAc(Fuc)-conjugated to BCN-dPEG$_4$-C(O)-Ahx-maytansin (observed mass of 26396 Da, calculated mass of 26399 Da). Trastuzumab-HC-N300Q-V366T showed one major heavy chain product which corresponds to the N300Q-V366T heavy chain substituted with GalNAzGlcNAc-Man$_5$-GlcNAc-GlcNAc(Fuc)-conjugated to BCN-dPEG$_4$-C(O)-Ahx-maytansin (observed mass of 52166 Da, calculated mass of 52170 Da). Trastuzumab-HC-L177N-N300Q showed one major heavy chain product, which corresponds to the L177N-N300Q heavy chain substituted with GalNAzGlcNAc-Man$_5$-GlcNAc$_2$-conjugated to BCN-dPEG$_4$-C(O)-Ahx-maytansin (observed mass of 52018 Da, calculated mass of 52023 Da).

Example 21: Conjugation of Trastuzumab Mutant, Glycoform GlcNAcMan$_5$GlcNAc, with DIBAC-dPEG$_4$-C(O)-Ahx-Maytansin Incubation of the above described trastuzumab mutant, glycoform GlcNAcMan$_5$GlcNAc (31, 15 mg/mL) with DIBAC-dPEG$_4$-C(O)-Ahx-maytansin (10 eq) in PBS for approximately 16 h led to complete conversion into the corresponding ADCs. Trastuzumab-HC-N300Q-LC-R18N showed one major light chain product which corresponds to the R18N light chain substituted with GalNAzGlcNAc-Man$_5$-GlcNAc-GlcNAc(Fuc)-conjugated to DIBAC-dPEG$_4$-C(O)-Ahx-maytansin (observed mass of 26507 Da, calculated mass of 26510 Da). Trastuzumab-HC-N300Q-V366T showed one major heavy chain product which corresponds to the N300Q-V366T heavy chain substituted with GalNAzGlcNAc-Man$_5$-GlcNAc-GlcNAc(Fuc)-conjugated to DIBAC-dPEG$_4$-C(O)-Ahx-maytansin (observed mass of 52278 Da, calculated mass of 52281 Da). Trastuzumab-HC-L177N-N300Q showed one major heavy chain product, which corresponds to the L177N-N300Q heavy chain substituted with GalNAzGlcNAc-Man$_s$-GlcNAc$_2$-conjugated to DIBAC-dPEG$_4$-C(O)-Ahx-maytansin (observed mass of 52130 Da, calculated mass of 52134 Da).

Example 22: Transfer of Mercaptosugar to Trastuzumab Mutant HC-N300Q-LC-R18N, Glycoform Man$_5$GlcNAc, Under the Action of GalT(Y289L, C342T)

The above described trastuzumab mutant HC-N300Q-LC-R18N, glycoform Man$_5$GlcNAc (29, 10 mg/mL) was incubated with the UDP-derivative of compound 15 (n=2) (1 mM) and β(1,4)-Gal-T1(Y289L, C342T) (0.2 mg/mL) in 10 mM MnCl$_2$ and 50 mM Tris-HCl pH 6.0 for 16 hours at 30° C. Subsequently, a sample was treated with DTT as described above and subsequent analyses by mass spectrometry showed the formation of the desired product (25214, expected mass 25219).

Example 23: Transfer of Mercaptosugar to Trastuzumab Mutant HC-N300Q-V366T, Glycoform Man$_5$GlcNAc, Under the Action of GalT(Y289L, C342T)

The above described trastuzumab mutant HC-N300Q-V366T, glycoform Man$_5$GlcNAc (29, 10 mg/mL) was incubated with the UDP-derivative of compound 15 (n=2) (1 mM) and β(1,4)-Gal-T1(Y289L, C342T) (0.2 mg/mL) in 10 mM MnCl$_2$ and 50 mM Tris-HCl pH 6.0 for 16 hours at 30° C. Subsequently, a sample was treated with DTT as described above and subsequent analyses by mass spectrometry showed the formation of the desired product (50981, expected mass 50991), about 70%.

Example 24: Transfer of Mercaptosugar to Trastuzumab Mutant HC-N300Q-L177N, Glycoform Man$_5$GlcNAc, Under the Action of GalT(Y289, C342T)

The above described trastuzumab mutant HC-N300Q-L177N, glycoform Man$_5$GlcNAc (29, 10 mg/mL) was incubated with the UDP-derivative of compound 15 (n=2) (1 mM) and β(1,4)-Gal-T1(Y289L, C342T) (0.2 mg/mL) in 10 mM MnCl$_2$ and 50 mM Tris-HCl pH 6.0 for 16 hours at 30° C. Subsequently, a sample was treated with DTT as described above and subsequent analyses by mass spectrometry showed the formation of the desired product (50836, expected mass 50844), about 70%.

Example 25: Transfer of Chlorosugar to Trastuzumab Mutant HC-N300Q-LC-R18N, Glycoform Man$_5$GlcNAc, Under the Action of GalT(Y289M)

The above described trastuzumab mutant HC-N300Q-LC-R18N, glycoform Man$_5$GlcNAc (29, 10 mg/mL) was incubated with the UDP-derivative of compound 20 (X=Cl) (0.66 mM) and β(1,4)-Gal-T1(Y289M) (0.15 mg/mL) in 10 mM MnCl$_2$ and 50 mM Tris-HCl pH 6.0 for 16 h at 30° C. Subsequently, a sample was treated with DTT as described above and subsequent analyses by mass spectrometry showed the formation of the desired product (25201, expected mass 25208).

Example 26: Transfer of Chlorosugar to Trastuzumab Mutant HC-N300Q-V366T, Glycoform Man$_5$GlcNAc, Under the Action of GalT(Y289M)

The above described trastuzumab mutant HC-N300Q-V366T, glycoform Man$_5$GlcNAc (29, 10 mg/mL) was incubated with the UDP-derivative of compound 20 (X=Cl) (0.66 mM) and β(1,4)-Gal-T1(Y289M) (0.15 mg/mL) in 10 mM MnCl$_2$ and 50 mM Tris-HCl pH 6.0 for 16 h at 30° C. Subsequently, a sample was treated with DTT as described above and subsequent analyses by mass spectrometry showed the formation of the desired product (50968, expected mass 50979).

Example 27: Transfer of Chlorosugar to Trastuzumab Mutant HC-N300Q-L177N, Glycoform Man$_5$GlcNAc, Under the Action of GalT(Y289M)

The above described trastuzumab mutant HC-N300Q-L177N, glycoform Man$_5$GlcNAc (29, 10 mg/mL) was incubated with the UDP-derivative of compound 20 (X=Cl) (0.66 mM) and β(1,4)-Gal-T1(Y289M) (0.15 mg/mL) in 10 mM MnCl$_2$ and 50 mM Tris-HCl pH 6.0 for 16 h at 30° C. Subsequently, a sample was treated with DTT as described above and subsequent analyses by mass spectrometry showed the formation of the desired product (50824, expected mass 50832).

Example 28: Reaction of Trastuzumab Mutant HC-N300Q-LC-R18N, Glycoform Man$_5$GlcNAc after Transfer of 20 (X=Cl), with 4-Mercaptobenzoic Acid Incubation of trastuzumab mutant HC-N300Q-LC-R18N, glycoform Man$_5$GlcNAc after transfer of 20 (X=Cl) (10 mg/mL in 50 mM Tris-HCl pH 6.0) with 4-mercaptobenzoic acid (6.6 μL, 0.1 M in DMF) and 1 M Tris-HCl pH 7.2 (40 μL) for approximately 16 h. Subsequently, a sample was treated with DTT as described above and subsequent analyses by mass spectrometry showed the formation of the desired product (25201, expected mass 25326).

Example 29: Conjugation of Trastuzumab Mutant HC-N300Q-V366T, Glycoform Man$_5$GlcNAc after Transfer of 20 (X=Cl), with 4-Mercaptobenzoic Acid Incubation of trastuzumab mutant HC-N300Q-V366T, glycoform Man$_5$GlcNAc after transfer of 20 (X=Cl) (10 mg/mL in 50 mM Tris-HCl pH 6.0) with 4-mercaptobenzoic acid (6.6 µL, 0.1 M in DMF) and 1 M Tris-HCl pH 7.2 (40 µL) for approximately 16 h. Subsequently, a sample was treated with DTT as described above and subsequent analyses by mass spectrometry showed the formation of the desired product (51092, expected mass 51098).

Example 30: Conjugation of Trastuzumab Mutant HC-N300Q-L177N, Glycoform Man$_5$GlcNAc after Transfer of 20 (X=Cl), with 4-Mercaptobenzoic Acid Incubation of trastuzumab mutant HC-N300Q-L177N, glycoform Man$_5$GlcNAc after transfer of 20 (X=Cl) (10 mg/mL in 50 mM Tris-HCl pH 6.0) with 4-mercaptobenzoic acid (6.6 µL, 0.1 M in DMF) and 1 M Tris-HCl pH 7.2 (40 µL) for approximately 16 h. Subsequently, a sample was treated with DTT as described above and subsequent analyses by mass spectrometry showed the formation of the desired product (50943, expected mass 50951).

The invention claimed is:

1. A process for the preparation of a protein-conjugate having formula:

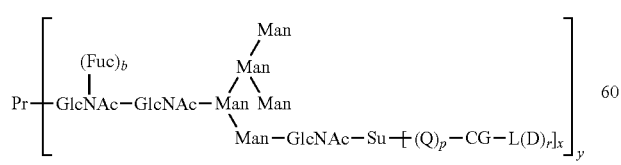

wherein:
Pr is a protein;
Su is a monosaccharide;
L is a linker;
D is a molecule of interest;
b is 0 or 1;
x is 1, 2, 3 or 4;
y is 1-20;
r is 1-20;
p is 0 or 1;
Q is $-N(H)C(O)CH_2-$ or $-CH_2-$; and
CG is a connecting group comprising:
 (a) a triazole reaction product of an azido group and a (hetero)cycloalkynyl group or an alkynyl group;
 (b) a reaction product of a thiol group and an N-maleimide group of formula

101

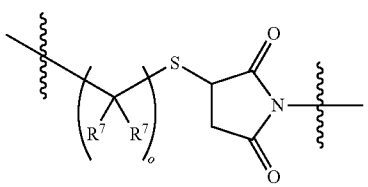

wherein N from the N-maleimide group is connected to L;
(c) a reaction product of a thiol group and a halogenated acetamido group of formula

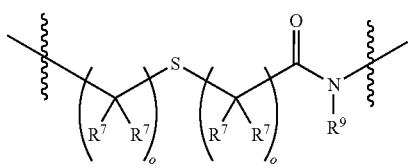

wherein N from the halogenated acetamido group is connected to L;
(d) a reaction product of a mercaptoacetamido group and an N-maleimide group of formula

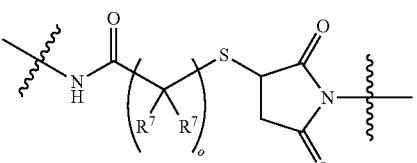

wherein N from the N-maleimide group is connected to L; or
(e) a reaction product of a mercaptoacetamido group and a halogenated acetamido group of formula

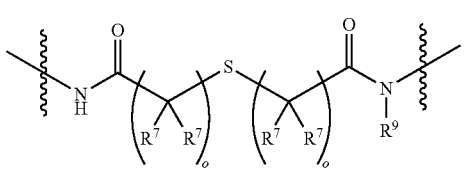

wherein N from the halogenated acetamido group is connected to L;
wherein:
$R^7$ at each occurrence is individually selected from the group consisting of hydrogen, halogen and an (optionally substituted) $C_1$-$C_{24}$ alkyl group;
$R^9$ is selected from the group consisting of $L(D)_r$, hydrogen, $C_1$-$C_{24}$ alkyl groups, $C_6$-$C_{24}$ aryl groups $C_7$-$C_{24}$ alkylaryl groups and $C_7$-$C_{24}$ arylalkyl groups, the $C_1$-$C_{24}$ alkyl groups, $C_6$-$C_{24}$ aryl groups $C_7$-$C_{24}$ alkylaryl groups and $C_7$-$C_{24}$ arylalkyl groups optionally being substituted; and
o at each occurrence is individually selected from 0-24;

102 comprising:
contacting a glycoprotein with $Su(A)_x$-P in the presence of a catalyst to prepare a modified glycoprotein; and
reacting the modified glycoprotein with a linker-conjugate;
wherein:
the glycoprotein comprises a glycan according to formula (101) and the modified glycoprotein comprise a modified glycan according to formula (102):

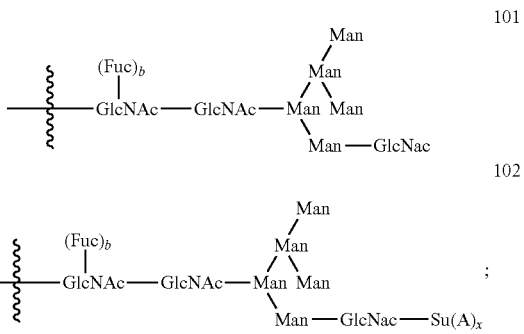

wherein:
b is as defined above;
$Su(A)_x$ is a monosaccharide sugar derivative comprising x functional groups A,
wherein:
x is as defined above, and
A is a functional group;
P is a nucleotide;
the catalyst is selected from the group consisting of β(1,4)-galactosyltransferases, β(1,3)-N-galactosyltransferases, β(1,4)-galactosyltransferases comprising a mutant catalytic domain, and β(1,3)-N-galactosyltransferases comprising a mutant catalytic domain; and
the linker-conjugate is according to formula B-L(D)r, wherein:
B is a functional group that is capable of reacting with the functional group A to provide -$(Q)_p$-CG- of the protein-conjugate; and
L, D, and are as defined above.

2. The process according to claim 1, wherein the catalyst is selected from the group consisting of a bovine β(1,4)-Gal-T1, a human β(1,4)-Gal-T1, a human β(1,4)-Gal-T2, a human β(1,4)-Gal-T4 and a human β(1,3)-Gal-T5.

3. The process according to claim 1, wherein the catalyst is a β(1,4)-galactosyltransferase comprising a mutant catalytic domain.

4. The process according to claim 3, wherein the catalyst comprises a mutant catalytic domain from a β(1,4)-galactosyltransferase selected from the group consisting of bovine β(1,4)-Gal-T1 GalT Y289L, GalT Y289N, GalT Y289I, GalT Y289F, GalT Y289M, GalT Y289V, GalT Y289G and GalT Y289A.

5. The process according to claim 1, wherein the glycoprotein is an antibody and the modified glycoprotein is a modified antibody.

6. The process according to claim 1, wherein the protein is an antibody.

7. The process according to claim 1, wherein A is an azido group.

8. A protein-conjugate having formula:

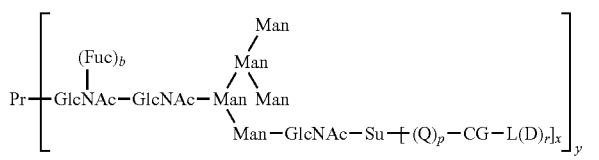

wherein:
Pr is a protein;
Su is a monosaccharide;
L is a linker;
D is a molecule of interest;
b is 0 or 1;
x is 1, 2, 3 or 4;
y is 1-20;
r is 1-20;
p is 0 or 1;
Q is —N(H)C(O)CH$_2$— or —CH$_2$—; and
CG is a connecting group comprising:
  a triazole reaction product of an azido group and a (hetero)cycloalkynyl group or an alkynyl group;
  (b) a reaction product of a thiol group and an N-maleimide group of formula

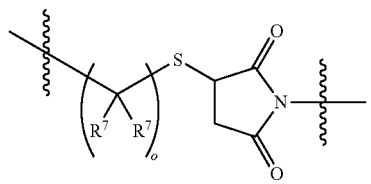

wherein N from the N-maleimide group is connected to L;
(c) a reaction product of a thiol group and a halogenated acetamido group of formula

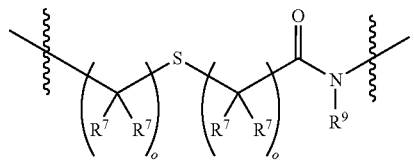

wherein N from the halogenated acetamido group is connected to L;
(d) a reaction product of a mercaptoacetamido group and an N-maleimide group of formula

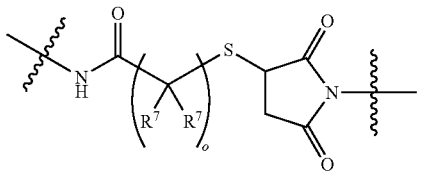

wherein N from the N-maleimide group is connected to L; or
(e) a reaction product of a mercaptoacetamido group and a halogenated acetamido group of formula

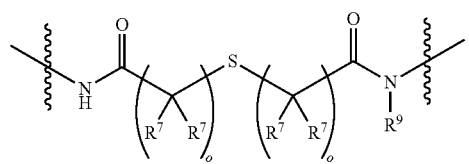

wherein N from the halogenated acetamido group is connected to L;
wherein:
  $R^7$ at each occurrence is individually selected from the group consisting of hydrogen, halogen and an (optionally substituted) $C_1$-$C_{24}$ alkyl group;
  $R^9$ is selected from the group consisting of L(D)$_r$, hydrogen, $C_1$-$C_{24}$ alkyl groups, $C_6$-$C_{24}$ aryl groups $C_7$-$C_{24}$ alkylaryl groups and $C_7$-$C_{24}$ arylalkyl groups, the $C_1$-$C_{24}$ alkyl groups, $C_6$-$C_{24}$ aryl groups $C_7$-$C_{24}$ alkylaryl groups and $C_7$-$C_{24}$ arylalkyl groups optionally being substituted; and
  o at each occurrence is individually selected from 0-24.

9. A protein-conjugate according to claim 8, wherein the protein-conjugate is according to formula (118) or (118b):

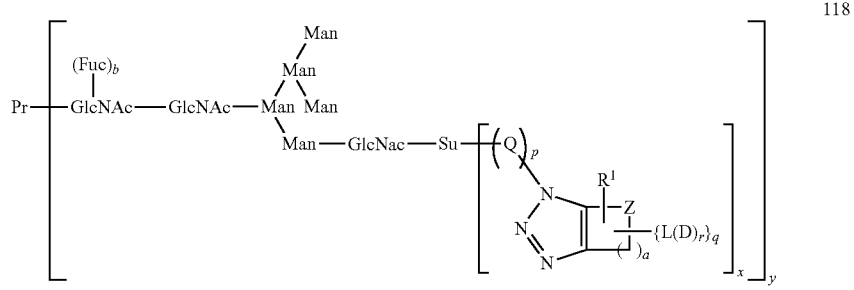

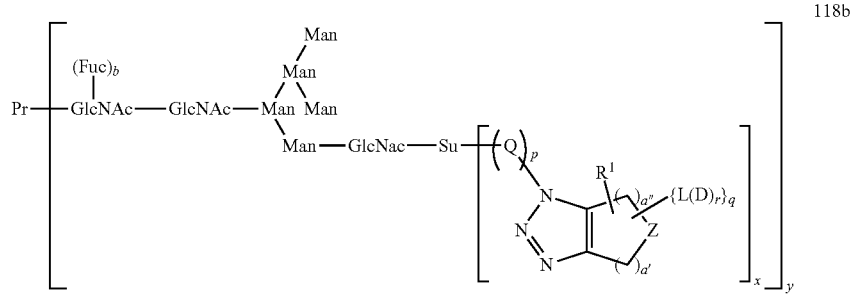

wherein:
Pr, Su, L, D, b, r, x, y, p, and Q are as defined in claim 8;
$R^1$ is independently selected from the group consisting of hydrogen, halogen, —$OR^5$, $NO_2$, —CN, —$S(O)_2R^5$, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups and wherein the alkyl groups, (hetero)aryl groups, alkyl(hetero)aryl groups and (hetero)arylalkyl groups are optionally substituted, wherein two substituents $R^1$ may be linked together to form an annelated cycloalkyl or an annelated (hetero)arene substituent, and wherein $R^5$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups;

Z is $C(R^1)_2$, O, S or $NR^2$,
  wherein $R^2$ is $R^1$ or $L(D)_r$, and wherein L, D and r are as defined above;
q is 0 or 1, with the proviso that if q is 0 then Z is N-L(D)r;
a is 1, 2, 3, 4, 5, 6, 7, 8, 9 or 10;
a' is 0, 1, 2, 3, 4, 5, 6, 7 or 8;
a" is 0, 1, 2, 3, 4, 5, 6, 7 or 8; and
a'+a"<10.

10. The protein-conjugate according to claim 8, wherein the protein-conjugate is according to formula (129) or (130):

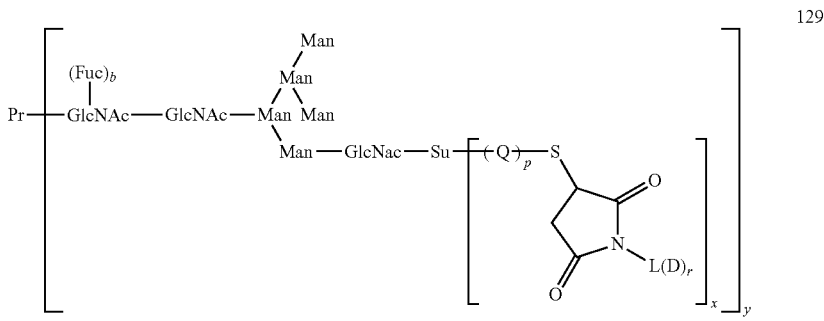

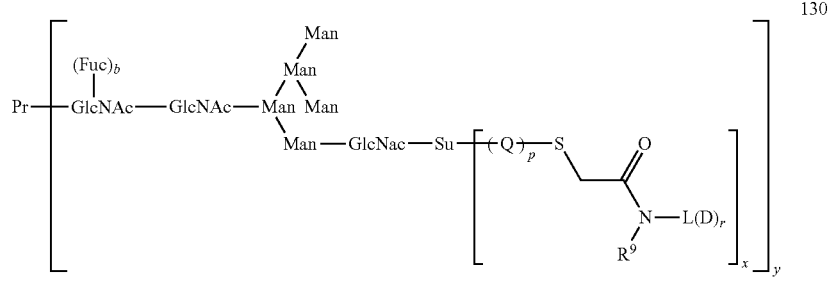

wherein:

Pr, Su, L, D, b, r, x, y, p, and Q are as defined in claim 8;

$R^9$ is selected from the group consisting of L(D)r, hydrogen, $C_1$-$C_{24}$ alkyl groups, $C_6$-$C_{24}$ aryl groups $C_7$-$C_{24}$ alkylaryl groups and $C_7$-$C_{24}$ arylalkyl groups, the $C_1$-$C_{24}$ alkyl groups, $C_6$-$C_{24}$ aryl groups $C_7$-$C_{24}$ alkylaryl groups and $C_7$-$C_{24}$ arylalkyl groups optionally being substituted.

11. The protein-conjugate according to claim 8, wherein the molecule of interest is selected from the group consisting of a reporter molecule, an active substance, an enzyme, an amino acid, a protein, a peptide, a polypeptide, an oligonucleotide, a glycan, a (poly)ethylene glycol diamine, a polyethylene glycol chain, a polyethylene oxide chain, a polypropylene glycol chain, a polypropylene oxide chain and 1,x-diaminoalkane, wherein x is the number of carbon atoms in the alkane and x is 1-200, an azide and a (hetero) cycloalkynyl moiety.

12. The protein-conjugate according to claim 11, wherein the (hetero)cycloalkynyl moiety is a bivalent or bifunctional (hetero)cycloalkynyl moiety.

13. The protein-conjugate according to claim 8, wherein the protein-conjugate is an antibody-conjugate.

14. An antibody-conjugate according to claim 13, wherein the molecule of interest is an active substance.

15. The protein-conjugate according to claim 8, wherein L is selected from the group consisting of linear or branched $C_1$-$C_{200}$ alkylene groups, $C_2$-$C_{200}$ alkenylene groups, $C_2$-$C_{200}$ alkynylene groups, $C_3$-$C_{200}$ cycloalkylene groups, $C_5$-$C_{200}$ cycloalkenylene groups, $C_8$-$C_{200}$ cycloalkenylene groups, $C_7$-$C_{200}$ alkylarylene groups, $C_7$-$C_{200}$ arylalkylene groups, $C_8$-$C_{200}$ arylalkenylene groups, and $C_9$-$C_{200}$ arylalkynylene groups, wherein the alkylene groups, alkenylene groups, alkynylene groups, cycloalkylene groups, cycloalkenylene groups, cycloalkenylene groups, alkylarylene groups, arylalkylene groups, arylalkenylene groups and arylalkynylene are optionally substituted and optionally interrupted by one or more heteroatoms selected from the group consisting of O, S and $NR^5$, wherein $R^5$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups.

16. The protein-conjugate according to claim 8, wherein the linker comprises:

a linking unit selected from (poly)ethylene glycol diamines, polyethylene glycol or polyethylene oxide chains, polypropylene glycol or polypropylene oxide chains and 1,x-diaminoalkanes, wherein x is the number of carbon atoms in the alkane; and/or a cleavable linker.

17. The protein-conjugate according to claim 11, wherein the molecule of interest is an active substance selected from the group consisting of cytotoxins, antiviral agents, antibacterial agents, peptides and oligonucleotides.

18. The protein-conjugate according to claim 17, wherein the molecule of interest is a cytotoxin selected from the group consisting of colchicine, vinca alkaloids, camptothecins, doxorubicin, daunorubicin, taxanes, calicheamycins, tubulysins, irinotecans, inhibitory peptides, amanitin, deBouganin, duocarmycins, maytansines, auristatins and pyrrolobenzodiazepines (PBDs).

19. The protein-conjugate according to claim 8, wherein Su is selected from the group consisting of galactose (Gal), mannose (Man), glucose (Glc), N-acetylneuraminic acid (NeuAc), fucose (Fuc), glucosamine ($GlcNH_2$), galactosamine ($GalNH_2$), N-acetylglucosamine (GlcNAc), glucose (Glc) and N-acetylgalactosamine (GalNAc).

* * * * *

```
                            SEQUENCE LISTING

<160> NUMBER OF SEQ ID NOS: 26

<210> SEQ ID NO 1
<211> LENGTH: 39
<212> TYPE: DNA
<213> ORGANISM: artificial
<220> FEATURE:
<223> OTHER INFORMATION: primer sequence

<400> SEQUENCE: 1
cagcgacata tgtcgctgac cgcatgccct gaggagtcc                              39

<210> SEQ ID NO 2
<211> LENGTH: 36
<212> TYPE: DNA
<213> ORGANISM: artificial
<220> FEATURE:
<223> OTHER INFORMATION: primer sequence

<400> SEQUENCE: 2
gacacctcca aagttctgca cgtaaggtag gctaaa                                 36

<210> SEQ ID NO 3
<211> LENGTH: 39
<212> TYPE: DNA
<213> ORGANISM: artificial
<220> FEATURE:
<223> OTHER INFORMATION: primer sequence

<400> SEQUENCE: 3
ctgatggatg gatccctagc tcggcgtccc gatgtccac                              39

<210> SEQ ID NO 4
<211> LENGTH: 36
<212> TYPE: DNA
<213> ORGANISM: artificial
<220> FEATURE:
<223> OTHER INFORMATION: primer sequence

<400> SEQUENCE: 4
ccttacgtgc agaactttgg aggtgtctct gctcta                                 36

<210> SEQ ID NO 5
<211> LENGTH: 36
<212> TYPE: DNA
<213> ORGANISM: artificial
<220> FEATURE:
<223> OTHER INFORMATION: primer sequence

<400> SEQUENCE: 5
gacacctcca aaaaactgca cgtaaggtag gctaaa                                 36
```

```
<210> SEQ ID NO 6
<211> LENGTH: 36
<212> TYPE: DNA
<213> ORGANISM: artificial
<220> FEATURE:
<223> OTHER INFORMATION: primer sequence

<400> SEQUENCE: 6
ccttacgtgc agtttttggt aggtgtctct gctcta                              36

<210> SEQ ID NO 7
<211> LENGTH: 36
<212> TYPE: DNA
<213> ORGANISM: artificial
<220> FEATURE:
<223> OTHER INFORMATION: primer sequence

<400> SEQUENCE: 7
gacacctcca aacatctgca cgtaaggtag gctaaa                              36

<210> SEQ ID NO 8
<211> LENGTH: 36
<212> TYPE: DNA
<213> ORGANISM: artificial
<220> FEATURE:
<223> OTHER INFORMATION: primer sequence

<400> SEQUENCE: 8
ccttacgtgc agatgtttgg aggtgtctct gctcta                              36

<210> SEQ ID NO 9
<211> LENGTH: 36
<212> TYPE: DNA
<213> ORGANISM: artificial
<220> FEATURE:
<223> OTHER INFORMATION: primer sequence

<400> SEQUENCE: 9
gacacctcca aaaatctgca cgtaaggtag gctaaa                              36

<210> SEQ ID NO 10
<211> LENGTH: 36
<212> TYPE: DNA
<213> ORGANISM: artificial
<220> FEATURE:
<223> OTHER INFORMATION: primer sequence

<400> SEQUENCE: 10
ccttacgtgc agattttggg aggtgtctct gctcta                              36

<210> SEQ ID NO 11
<211> LENGTH: 36
<212> TYPE: DNA
<213> ORGANISM: artificial
<220> FEATURE:
<223> OTHER INFORMATION: primer sequence

<400> SEQUENCE: 11
gacacctcca aacacctgca cgtaaggtag gctaaa                              36

<210> SEQ ID NO 12
<211> LENGTH: 36
<212> TYPE: DNA
<213> ORGANISM: artificial
<220> FEATURE:
<223> OTHER INFORMATION: primer sequence
```

```
<400> SEQUENCE: 12
ccttacgtgc aggtgtttgg aggtgtctct gctcta                              36

<210> SEQ ID NO 13
<211> LENGTH: 36
<212> TYPE: DNA
<213> ORGANISM: artificial
<220> FEATURE:
<223> OTHER INFORMATION: primer sequence

<400> SEQUENCE: 13
gacacctcca aacgcctgca cgtaaggtag gctaaa                              36

<210> SEQ ID NO 14
<211> LENGTH: 36
<212> TYPE: DNA
<213> ORGANISM: artificial
<220> FEATURE:
<223> OTHER INFORMATION: primer sequence

<400> SEQUENCE: 14
ccttacgtgc aggcgtttgg aggtgtctct gctcta                              36

<210> SEQ ID NO 15
<211> LENGTH: 36
<212> TYPE: DNA
<213> ORGANISM: artificial
<220> FEATURE:
<223> OTHER INFORMATION: primer sequence

<400> SEQUENCE: 15
gacacctcca aagccctgca cgtaaggtag gctaaa                              36

<210> SEQ ID NO 16
<211> LENGTH: 36
<212> TYPE: DNA
<213> ORGANISM: artificial
<220> FEATURE:
<223> OTHER INFORMATION: primer sequence

<400> SEQUENCE: 16
ccttacgtgc agggctttgg aggtgtctct gctcta                              36

<210> SEQ ID NO 17
<211> LENGTH: 402
<212> TYPE: PRT
<213> ORGANISM: Bos taurus

<400> SEQUENCE: 17

Met Lys Phe Arg Glu Pro Leu Leu Gly Gly Ser Ala Ala Met Pro Gly
1               5                   10                  15

Ala Ser Leu Gln Arg Ala Cys Arg Leu Leu Val Ala Val Cys Ala Leu
            20                  25                  30

His Leu Gly Val Thr Leu Val Tyr Tyr Leu Ala Gly Arg Asp Leu Arg
        35                  40                  45

Arg Leu Pro Gln Leu Val Gly Val His Pro Pro Leu Gln Gly Ser Ser
    50                  55                  60

His Gly Ala Ala Ala Ile Gly Gln Pro Ser Gly Glu Leu Arg Leu Arg
65                  70                  75                  80

Gly Val Ala Pro Pro Pro Leu Gln Asn Ser Ser Lys Pro Arg Ser
                85                  90                  95
```

```
Arg Ala Pro Ser Asn Leu Asp Ala Tyr Ser His Pro Gly Pro
            100                 105                 110

Gly Pro Gly Ser Asn Leu Thr Ser Ala Pro Val Pro Ser Thr Thr Thr
            115                 120                 125

Arg Ser Leu Thr Ala Cys Pro Glu Glu Ser Pro Leu Leu Val Gly Pro
            130                 135                 140

Met Leu Ile Glu Phe Asn Ile Pro Val Asp Leu Lys Leu Ile Glu Gln
145                 150                 155                 160

Gln Asn Pro Lys Val Lys Leu Gly Gly Arg Tyr Thr Pro Met Asp Cys
                165                 170                 175

Ile Ser Pro His Lys Val Ala Ile Ile Ile Leu Phe Arg Asn Arg Gln
            180                 185                 190

Glu His Leu Lys Tyr Trp Leu Tyr Tyr Leu His Pro Met Val Gln Arg
            195                 200                 205

Gln Gln Leu Asp Tyr Gly Ile Tyr Val Ile Asn Gln Ala Gly Glu Ser
            210                 215                 220

Met Phe Asn Arg Ala Lys Leu Leu Asn Val Gly Phe Lys Glu Ala Leu
225                 230                 235                 240

Lys Asp Tyr Asp Tyr Asn Cys Phe Val Phe Ser Asp Val Asp Leu Ile
                245                 250                 255

Pro Met Asn Asp His Asn Thr Tyr Arg Cys Phe Ser Gln Pro Arg His
            260                 265                 270

Ile Ser Val Ala Met Asp Lys Phe Gly Phe Ser Leu Pro Tyr Val Gln
            275                 280                 285

Tyr Phe Gly Gly Val Ser Ala Leu Ser Lys Gln Gln Phe Leu Ser Ile
            290                 295                 300

Asn Gly Phe Pro Asn Asn Tyr Trp Gly Trp Gly Gly Glu Asp Asp Asp
305                 310                 315                 320

Ile Tyr Asn Arg Leu Ala Phe Arg Gly Met Ser Val Ser Arg Pro Asn
                325                 330                 335

Ala Val Ile Gly Lys Cys Arg Met Ile Arg His Ser Arg Asp Lys Lys
            340                 345                 350

Asn Glu Pro Asn Pro Gln Arg Phe Asp Arg Ile Ala His Thr Lys Glu
            355                 360                 365

Thr Met Leu Ser Asp Gly Leu Asn Ser Leu Thr Tyr Met Val Leu Glu
370                 375                 380

Val Gln Arg Tyr Pro Leu Tyr Thr Lys Ile Thr Val Asp Ile Gly Thr
385                 390                 395                 400

Pro Ser

<210> SEQ ID NO 18
<211> LENGTH: 402
<212> TYPE: PRT
<213> ORGANISM: artificial
<220> FEATURE:
<223> OTHER INFORMATION: bos taurus GalT Y289N

<400> SEQUENCE: 18

Met Lys Phe Arg Glu Pro Leu Leu Gly Gly Ser Ala Ala Met Pro Gly
1               5                   10                  15

Ala Ser Leu Gln Arg Ala Cys Arg Leu Leu Val Ala Val Cys Ala Leu
            20                  25                  30

His Leu Gly Val Thr Leu Val Tyr Tyr Leu Ala Gly Arg Asp Leu Arg
            35                  40                  45

Arg Leu Pro Gln Leu Val Gly Val His Pro Pro Leu Gln Gly Ser Ser
```

-continued

```
                50                  55                  60
His Gly Ala Ala Ala Ile Gly Gln Pro Ser Gly Glu Leu Arg Leu Arg
 65                  70                  75                  80

Gly Val Ala Pro Pro Pro Leu Gln Asn Ser Ser Lys Pro Arg Ser
                 85                  90                  95

Arg Ala Pro Ser Asn Leu Asp Ala Tyr Ser His Pro Gly Pro Gly Pro
                100                 105                 110

Gly Pro Gly Ser Asn Leu Thr Ser Ala Pro Val Pro Ser Thr Thr Thr
                115                 120                 125

Arg Ser Leu Thr Ala Cys Pro Glu Glu Ser Pro Leu Leu Val Gly Pro
                130                 135                 140

Met Leu Ile Glu Phe Asn Ile Pro Val Asp Leu Lys Leu Ile Glu Gln
145                 150                 155                 160

Gln Asn Pro Lys Val Lys Leu Gly Gly Arg Tyr Thr Pro Met Asp Cys
                165                 170                 175

Ile Ser Pro His Lys Val Ala Ile Ile Ile Leu Phe Arg Asn Arg Gln
                180                 185                 190

Glu His Leu Lys Tyr Trp Leu Tyr Tyr Leu His Pro Met Val Gln Arg
                195                 200                 205

Gln Gln Leu Asp Tyr Gly Ile Tyr Val Ile Asn Gln Ala Gly Glu Ser
                210                 215                 220

Met Phe Asn Arg Ala Lys Leu Leu Asn Val Gly Phe Lys Glu Ala Leu
225                 230                 235                 240

Lys Asp Tyr Asp Tyr Asn Cys Phe Val Phe Ser Asp Val Asp Leu Ile
                245                 250                 255

Pro Met Asn Asp His Asn Thr Tyr Arg Cys Phe Ser Gln Pro Arg His
                260                 265                 270

Ile Ser Val Ala Met Asp Lys Phe Gly Phe Ser Leu Pro Tyr Val Gln
                275                 280                 285

Asn Phe Gly Gly Val Ser Ala Leu Ser Lys Gln Gln Phe Leu Ser Ile
                290                 295                 300

Asn Gly Phe Pro Asn Asn Tyr Trp Gly Trp Gly Gly Glu Asp Asp Asp
305                 310                 315                 320

Ile Tyr Asn Arg Leu Ala Phe Arg Gly Met Ser Val Ser Arg Pro Asn
                325                 330                 335

Ala Val Ile Gly Lys Cys Arg Met Ile Arg His Ser Arg Asp Lys Lys
                340                 345                 350

Asn Glu Pro Asn Pro Gln Arg Phe Asp Arg Ile Ala His Thr Lys Glu
                355                 360                 365

Thr Met Leu Ser Asp Gly Leu Asn Ser Leu Thr Tyr Met Val Leu Glu
                370                 375                 380

Val Gln Arg Tyr Pro Leu Tyr Thr Lys Ile Thr Val Asp Ile Gly Thr
385                 390                 395                 400

Pro Ser
```

<210> SEQ ID NO 19
<211> LENGTH: 402
<212> TYPE: PRT
<213> ORGANISM: artificial
<220> FEATURE:
<223> OTHER INFORMATION: bos taurus GalT Y289F

<400> SEQUENCE: 19

```
Met Lys Phe Arg Glu Pro Leu Leu Gly Gly Ser Ala Ala Met Pro Gly
  1               5                  10                  15
```

Ala Ser Leu Gln Arg Ala Cys Arg Leu Leu Val Ala Val Cys Ala Leu
            20                  25                  30

His Leu Gly Val Thr Leu Val Tyr Leu Ala Gly Arg Asp Leu Arg
         35                  40                  45

Arg Leu Pro Gln Leu Val Gly Val His Pro Leu Gln Gly Ser Ser
 50                  55                  60

His Gly Ala Ala Ala Ile Gly Gln Pro Ser Gly Glu Leu Arg Leu Arg
 65                  70                  75                  80

Gly Val Ala Pro Pro Pro Leu Gln Asn Ser Ser Lys Pro Arg Ser
                 85                  90                  95

Arg Ala Pro Ser Asn Leu Asp Ala Tyr Ser His Pro Gly Pro Gly Pro
             100                 105                 110

Gly Pro Gly Ser Asn Leu Thr Ser Ala Pro Val Pro Ser Thr Thr Thr
             115                 120                 125

Arg Ser Leu Thr Ala Cys Pro Glu Ser Pro Leu Leu Val Gly Pro
130                 135                 140

Met Leu Ile Glu Phe Asn Ile Pro Val Asp Leu Lys Leu Ile Glu Gln
145                 150                 155                 160

Gln Asn Pro Lys Val Lys Leu Gly Gly Arg Tyr Thr Pro Met Asp Cys
                165                 170                 175

Ile Ser Pro His Lys Val Ala Ile Ile Leu Phe Arg Asn Arg Gln
            180                 185                 190

Glu His Leu Lys Tyr Trp Leu Tyr Tyr Leu His Pro Met Val Gln Arg
        195                 200                 205

Gln Gln Leu Asp Tyr Gly Ile Tyr Val Ile Asn Gln Ala Gly Glu Ser
    210                 215                 220

Met Phe Asn Arg Ala Lys Leu Leu Asn Val Gly Phe Lys Glu Ala Leu
225                 230                 235                 240

Lys Asp Tyr Asp Tyr Asn Cys Phe Val Phe Ser Asp Val Asp Leu Ile
                245                 250                 255

Pro Met Asn Asp His Asn Thr Tyr Arg Cys Phe Ser Gln Pro Arg His
            260                 265                 270

Ile Ser Val Ala Met Asp Lys Phe Gly Phe Ser Leu Pro Tyr Val Gln
        275                 280                 285

Phe Phe Gly Gly Val Ser Ala Leu Ser Lys Gln Gln Phe Leu Ser Ile
    290                 295                 300

Asn Gly Phe Pro Asn Asn Tyr Trp Gly Trp Gly Gly Glu Asp Asp Asp
305                 310                 315                 320

Ile Tyr Asn Arg Leu Ala Phe Arg Gly Met Ser Val Ser Arg Pro Asn
                325                 330                 335

Ala Val Ile Gly Lys Cys Arg Met Ile Arg His Ser Arg Asp Lys Lys
            340                 345                 350

Asn Glu Pro Asn Pro Gln Arg Phe Asp Arg Ile Ala His Thr Lys Glu
        355                 360                 365

Thr Met Leu Ser Asp Gly Leu Asn Ser Leu Thr Tyr Met Val Leu Glu
    370                 375                 380

Val Gln Arg Tyr Pro Leu Tyr Thr Lys Ile Thr Val Asp Ile Gly Thr
385                 390                 395                 400

Pro Ser

<210> SEQ ID NO 20
<211> LENGTH: 402
<212> TYPE: PRT

<213> ORGANISM: artificial
<220> FEATURE:
<223> OTHER INFORMATION: bos taurus GalT Y289M

<400> SEQUENCE: 20

```
Met Lys Phe Arg Glu Pro Leu Leu Gly Gly Ser Ala Ala Met Pro Gly
1               5                   10                  15

Ala Ser Leu Gln Arg Ala Cys Arg Leu Leu Val Ala Val Cys Ala Leu
            20                  25                  30

His Leu Gly Val Thr Leu Val Tyr Tyr Leu Ala Gly Arg Asp Leu Arg
        35                  40                  45

Arg Leu Pro Gln Leu Val Gly Val His Pro Leu Gln Gly Ser Ser
    50                  55                  60

His Gly Ala Ala Ala Ile Gly Gln Pro Ser Gly Glu Leu Arg Leu Arg
65                  70                  75                  80

Gly Val Ala Pro Pro Pro Leu Gln Asn Ser Ser Lys Pro Arg Ser
                85                  90                  95

Arg Ala Pro Ser Asn Leu Asp Ala Tyr Ser His Pro Gly Pro Gly Pro
                100                 105                 110

Gly Pro Gly Ser Asn Leu Thr Ser Ala Pro Val Pro Ser Thr Thr Thr
            115                 120                 125

Arg Ser Leu Thr Ala Cys Pro Glu Glu Ser Pro Leu Leu Val Gly Pro
    130                 135                 140

Met Leu Ile Glu Phe Asn Ile Pro Val Asp Leu Lys Leu Ile Glu Gln
145                 150                 155                 160

Gln Asn Pro Lys Val Lys Leu Gly Gly Arg Tyr Thr Pro Met Asp Cys
                165                 170                 175

Ile Ser Pro His Lys Val Ala Ile Ile Ile Leu Phe Arg Asn Arg Gln
            180                 185                 190

Glu His Leu Lys Tyr Trp Leu Tyr Tyr Leu His Pro Met Val Gln Arg
        195                 200                 205

Gln Gln Leu Asp Tyr Gly Ile Tyr Val Ile Asn Gln Ala Gly Glu Ser
    210                 215                 220

Met Phe Asn Arg Ala Lys Leu Leu Asn Val Gly Phe Lys Glu Ala Leu
225                 230                 235                 240

Lys Asp Tyr Asp Tyr Asn Cys Phe Val Phe Ser Asp Val Asp Leu Ile
                245                 250                 255

Pro Met Asn Asp His Asn Thr Tyr Arg Cys Phe Ser Gln Pro Arg His
            260                 265                 270

Ile Ser Val Ala Met Asp Lys Phe Gly Phe Ser Leu Pro Tyr Val Gln
        275                 280                 285

Met Phe Gly Gly Val Ser Ala Leu Ser Lys Gln Gln Phe Leu Ser Ile
    290                 295                 300

Asn Gly Phe Pro Asn Asn Tyr Trp Gly Trp Gly Gly Glu Asp Asp Asp
305                 310                 315                 320

Ile Tyr Asn Arg Leu Ala Phe Arg Gly Met Ser Val Ser Arg Pro Asn
                325                 330                 335

Ala Val Ile Gly Lys Cys Arg Met Ile Arg His Ser Arg Asp Lys Lys
            340                 345                 350

Asn Glu Pro Asn Pro Gln Arg Phe Asp Arg Ile Ala His Thr Lys Glu
        355                 360                 365

Thr Met Leu Ser Asp Gly Leu Asn Ser Leu Thr Tyr Met Val Leu Glu
    370                 375                 380

Val Gln Arg Tyr Pro Leu Tyr Thr Lys Ile Thr Val Asp Ile Gly Thr
```

Pro Ser

<210> SEQ ID NO 21
<211> LENGTH: 402
<212> TYPE: PRT
<213> ORGANISM: artificial
<220> FEATURE:
<223> OTHER INFORMATION: bos taurus GalT Y289I

<400> SEQUENCE: 21

```
Met Lys Phe Arg Glu Pro Leu Leu Gly Gly Ser Ala Ala Met Pro Gly
1               5                   10                  15

Ala Ser Leu Gln Arg Ala Cys Arg Leu Leu Val Ala Val Cys Ala Leu
            20                  25                  30

His Leu Gly Val Thr Leu Val Tyr Tyr Leu Ala Gly Arg Asp Leu Arg
        35                  40                  45

Arg Leu Pro Gln Leu Val Gly Val His Pro Leu Gln Gly Ser Ser
    50                  55                  60

His Gly Ala Ala Ala Ile Gly Gln Pro Ser Gly Glu Leu Arg Leu Arg
65                  70                  75                  80

Gly Val Ala Pro Pro Pro Leu Gln Asn Ser Ser Lys Pro Arg Ser
                85                  90                  95

Arg Ala Pro Ser Asn Leu Asp Ala Tyr Ser His Pro Gly Pro Gly Pro
            100                 105                 110

Gly Pro Gly Ser Asn Leu Thr Ser Ala Pro Val Pro Ser Thr Thr Thr
        115                 120                 125

Arg Ser Leu Thr Ala Cys Pro Glu Glu Ser Pro Leu Leu Val Gly Pro
    130                 135                 140

Met Leu Ile Glu Phe Asn Ile Pro Val Asp Leu Lys Leu Ile Glu Gln
145                 150                 155                 160

Gln Asn Pro Lys Val Lys Leu Gly Gly Arg Tyr Thr Pro Met Asp Cys
                165                 170                 175

Ile Ser Pro His Lys Val Ala Ile Ile Ile Leu Phe Arg Asn Arg Gln
            180                 185                 190

Glu His Leu Lys Tyr Trp Leu Tyr Tyr Leu His Pro Met Val Gln Arg
        195                 200                 205

Gln Gln Leu Asp Tyr Gly Ile Tyr Val Ile Asn Gln Ala Gly Glu Ser
    210                 215                 220

Met Phe Asn Arg Ala Lys Leu Leu Asn Val Gly Phe Lys Glu Ala Leu
225                 230                 235                 240

Lys Asp Tyr Asp Tyr Asn Cys Phe Val Phe Ser Asp Val Asp Leu Ile
                245                 250                 255

Pro Met Asn Asp His Asn Thr Tyr Arg Cys Phe Ser Gln Pro Arg His
            260                 265                 270

Ile Ser Val Ala Met Asp Lys Phe Gly Phe Ser Leu Pro Tyr Val Gln
        275                 280                 285

Ile Phe Gly Gly Val Ser Ala Leu Ser Lys Gln Gln Phe Leu Ser Ile
    290                 295                 300

Asn Gly Phe Pro Asn Asn Tyr Trp Gly Trp Gly Gly Glu Asp Asp Asp
305                 310                 315                 320

Ile Tyr Asn Arg Leu Ala Phe Arg Gly Met Ser Val Ser Arg Pro Asn
                325                 330                 335

Ala Val Ile Gly Lys Cys Arg Met Ile Arg His Ser Arg Asp Lys Lys
            340                 345                 350
```

-continued

```
Asn Glu Pro Asn Pro Gln Arg Phe Asp Arg Ile Ala His Thr Lys Glu
            355                 360                 365

Thr Met Leu Ser Asp Gly Leu Asn Ser Leu Thr Tyr Met Val Leu Glu
    370                 375                 380

Val Gln Arg Tyr Pro Leu Tyr Thr Lys Ile Thr Val Asp Ile Gly Thr
385                 390                 395                 400

Pro Ser

<210> SEQ ID NO 22
<211> LENGTH: 402
<212> TYPE: PRT
<213> ORGANISM: artificial
<220> FEATURE:
<223> OTHER INFORMATION: bos taurus GalT Y289V

<400> SEQUENCE: 22

Met Lys Phe Arg Glu Pro Leu Leu Gly Gly Ser Ala Ala Met Pro Gly
1               5                   10                  15

Ala Ser Leu Gln Arg Ala Cys Arg Leu Val Ala Val Cys Ala Leu
                20                  25                  30

His Leu Gly Val Thr Leu Val Tyr Tyr Leu Ala Gly Arg Asp Leu Arg
            35                  40                  45

Arg Leu Pro Gln Leu Val Gly Val His Pro Leu Gln Gly Ser Ser
    50                  55                  60

His Gly Ala Ala Ala Ile Gly Gln Pro Ser Gly Glu Leu Arg Leu Arg
65                  70                  75                  80

Gly Val Ala Pro Pro Pro Leu Gln Asn Ser Ser Lys Pro Arg Ser
                85                  90                  95

Arg Ala Pro Ser Asn Leu Asp Ala Tyr Ser His Pro Gly Pro Gly Pro
            100                 105                 110

Gly Pro Gly Ser Asn Leu Thr Ser Ala Pro Val Pro Ser Thr Thr Thr
        115                 120                 125

Arg Ser Leu Thr Ala Cys Pro Glu Glu Ser Pro Leu Leu Val Gly Pro
    130                 135                 140

Met Leu Ile Glu Phe Asn Ile Pro Val Asp Leu Lys Leu Ile Glu Gln
145                 150                 155                 160

Gln Asn Pro Lys Val Lys Leu Gly Gly Arg Tyr Thr Pro Met Asp Cys
                165                 170                 175

Ile Ser Pro His Lys Val Ala Ile Ile Ile Leu Phe Arg Asn Arg Gln
            180                 185                 190

Glu His Leu Lys Tyr Trp Leu Tyr Tyr Leu His Pro Met Val Gln Arg
        195                 200                 205

Gln Gln Leu Asp Tyr Gly Ile Tyr Val Ile Asn Gln Ala Gly Glu Ser
    210                 215                 220

Met Phe Asn Arg Ala Lys Leu Leu Asn Val Gly Phe Lys Glu Ala Leu
225                 230                 235                 240

Lys Asp Tyr Asp Tyr Asn Cys Phe Val Phe Ser Asp Val Asp Leu Ile
                245                 250                 255

Pro Met Asn Asp His Asn Thr Tyr Arg Cys Phe Ser Gln Pro Arg His
            260                 265                 270

Ile Ser Val Ala Met Asp Lys Phe Gly Phe Ser Leu Pro Tyr Val Gln
        275                 280                 285

Val Phe Gly Gly Val Ser Ala Leu Ser Lys Gln Gln Phe Leu Ser Ile
    290                 295                 300
```

```
Asn Gly Phe Pro Asn Asn Tyr Trp Gly Trp Gly Glu Asp Asp Asp
305                 310                 315                 320

Ile Tyr Asn Arg Leu Ala Phe Arg Gly Met Ser Val Ser Arg Pro Asn
            325                 330                 335

Ala Val Ile Gly Lys Cys Arg Met Ile Arg His Ser Arg Asp Lys Lys
        340                 345                 350

Asn Glu Pro Asn Pro Gln Arg Phe Asp Arg Ile Ala His Thr Lys Glu
            355                 360                 365

Thr Met Leu Ser Asp Gly Leu Asn Ser Leu Thr Tyr Met Val Leu Glu
        370                 375                 380

Val Gln Arg Tyr Pro Leu Tyr Thr Lys Ile Thr Val Asp Ile Gly Thr
385                 390                 395                 400

Pro Ser

<210> SEQ ID NO 23
<211> LENGTH: 402
<212> TYPE: PRT
<213> ORGANISM: artificial
<220> FEATURE:
<223> OTHER INFORMATION: bos taurus GalT Y289A

<400> SEQUENCE: 23

Met Lys Phe Arg Glu Pro Leu Leu Gly Gly Ser Ala Ala Met Pro Gly
1               5                   10                  15

Ala Ser Leu Gln Arg Ala Cys Arg Leu Val Ala Val Cys Ala Leu
            20                  25                  30

His Leu Gly Val Thr Leu Val Tyr Tyr Leu Ala Gly Arg Asp Leu Arg
        35                  40                  45

Arg Leu Pro Gln Leu Val Gly Val His Pro Pro Leu Gln Gly Ser Ser
    50                  55                  60

His Gly Ala Ala Ala Ile Gly Gln Pro Ser Gly Glu Leu Arg Leu Arg
65                  70                  75                  80

Gly Val Ala Pro Pro Pro Leu Gln Asn Ser Ser Lys Pro Arg Ser
                85                  90                  95

Arg Ala Pro Ser Asn Leu Asp Ala Tyr Ser His Pro Gly Pro Gly Pro
            100                 105                 110

Gly Pro Gly Ser Asn Leu Thr Ser Ala Pro Val Pro Ser Thr Thr Thr
        115                 120                 125

Arg Ser Leu Thr Ala Cys Pro Glu Glu Ser Pro Leu Leu Val Gly Pro
    130                 135                 140

Met Leu Ile Glu Phe Asn Ile Pro Val Asp Leu Lys Leu Ile Glu Gln
145                 150                 155                 160

Gln Asn Pro Lys Val Lys Leu Gly Gly Arg Tyr Thr Pro Met Asp Cys
                165                 170                 175

Ile Ser Pro His Lys Val Ala Ile Ile Ile Leu Phe Arg Asn Arg Gln
            180                 185                 190

Glu His Leu Lys Tyr Trp Leu Tyr Tyr Leu His Pro Met Val Gln Arg
        195                 200                 205

Gln Gln Leu Asp Tyr Gly Ile Tyr Val Ile Asn Gln Ala Gly Glu Ser
    210                 215                 220

Met Phe Asn Arg Ala Lys Leu Leu Asn Val Gly Phe Lys Glu Ala Leu
225                 230                 235                 240

Lys Asp Tyr Asp Tyr Asn Cys Phe Val Phe Ser Asp Val Asp Leu Ile
                245                 250                 255

Pro Met Asn Asp His Asn Thr Tyr Arg Cys Phe Ser Gln Pro Arg His
```

```
            260                 265                 270
Ile Ser Val Ala Met Asp Lys Phe Gly Phe Ser Leu Pro Tyr Val Gln
        275                 280                 285

Ala Phe Gly Gly Val Ser Ala Leu Ser Lys Gln Gln Phe Leu Ser Ile
        290                 295                 300

Asn Gly Phe Pro Asn Asn Tyr Trp Gly Trp Gly Gly Glu Asp Asp Asp
305                 310                 315                 320

Ile Tyr Asn Arg Leu Ala Phe Arg Gly Met Ser Val Ser Arg Pro Asn
                325                 330                 335

Ala Val Ile Gly Lys Cys Arg Met Ile Arg His Ser Arg Asp Lys Lys
            340                 345                 350

Asn Glu Pro Asn Pro Gln Arg Phe Asp Arg Ile Ala His Thr Lys Glu
        355                 360                 365

Thr Met Leu Ser Asp Gly Leu Asn Ser Leu Thr Tyr Met Val Leu Glu
        370                 375                 380

Val Gln Arg Tyr Pro Leu Tyr Thr Lys Ile Thr Val Asp Ile Gly Thr
385                 390                 395                 400

Pro Ser

<210> SEQ ID NO 24
<211> LENGTH: 402
<212> TYPE: PRT
<213> ORGANISM: artificial
<220> FEATURE:
<223> OTHER INFORMATION: bos taurus GalT Y289G

<400> SEQUENCE: 24

Met Lys Phe Arg Glu Pro Leu Leu Gly Gly Ser Ala Ala Met Pro Gly
1               5                   10                  15

Ala Ser Leu Gln Arg Ala Cys Arg Leu Leu Val Ala Val Cys Ala Leu
            20                  25                  30

His Leu Gly Val Thr Leu Val Tyr Tyr Leu Ala Gly Arg Asp Leu Arg
        35                  40                  45

Arg Leu Pro Gln Leu Val Gly Val His Pro Pro Leu Gln Gly Ser Ser
    50                  55                  60

His Gly Ala Ala Ala Ile Gly Gln Pro Ser Gly Glu Leu Arg Leu Arg
65                  70                  75                  80

Gly Val Ala Pro Pro Pro Leu Gln Asn Ser Ser Lys Pro Arg Ser Arg
                85                  90                  95

Arg Ala Pro Ser Asn Leu Asp Ala Tyr Ser His Pro Gly Pro Gly Pro
            100                 105                 110

Gly Pro Gly Ser Asn Leu Thr Ser Ala Pro Val Pro Ser Thr Thr Thr
        115                 120                 125

Arg Ser Leu Thr Ala Cys Pro Glu Glu Ser Pro Leu Leu Val Gly Pro
    130                 135                 140

Met Leu Ile Glu Phe Asn Ile Pro Val Asp Leu Lys Leu Ile Glu Gln
145                 150                 155                 160

Gln Asn Pro Lys Val Lys Leu Gly Gly Arg Tyr Thr Pro Met Asp Cys
                165                 170                 175

Ile Ser Pro His Lys Val Ala Ile Ile Ile Leu Phe Arg Asn Arg Gln
            180                 185                 190

Glu His Leu Lys Tyr Trp Leu Tyr Tyr Leu His Pro Met Val Gln Arg
        195                 200                 205

Gln Gln Leu Asp Tyr Gly Ile Tyr Val Ile Asn Gln Ala Gly Glu Ser
    210                 215                 220
```

```
Met Phe Asn Arg Ala Lys Leu Leu Asn Val Gly Phe Lys Glu Ala Leu
225                 230                 235                 240

Lys Asp Tyr Asp Tyr Asn Cys Phe Val Phe Ser Asp Val Asp Leu Ile
                245                 250                 255

Pro Met Asn Asp His Asn Thr Tyr Arg Cys Phe Ser Gln Pro Arg His
            260                 265                 270

Ile Ser Val Ala Met Asp Lys Phe Gly Phe Ser Leu Pro Tyr Val Gln
            275                 280                 285

Gly Phe Gly Gly Val Ser Ala Leu Ser Lys Gln Gln Phe Leu Ser Ile
        290                 295                 300

Asn Gly Phe Pro Asn Asn Tyr Trp Gly Trp Gly Gly Glu Asp Asp Asp
305                 310                 315                 320

Ile Tyr Asn Arg Leu Ala Phe Arg Gly Met Ser Val Ser Arg Pro Asn
                325                 330                 335

Ala Val Ile Gly Lys Cys Arg Met Ile Arg His Ser Arg Asp Lys Lys
            340                 345                 350

Asn Glu Pro Asn Pro Gln Arg Phe Asp Arg Ile Ala His Thr Lys Glu
            355                 360                 365

Thr Met Leu Ser Asp Gly Leu Asn Ser Leu Thr Tyr Met Val Leu Glu
        370                 375                 380

Val Gln Arg Tyr Pro Leu Tyr Thr Lys Ile Thr Val Asp Ile Gly Thr
385                 390                 395                 400

Pro Ser

<210> SEQ ID NO 25
<211> LENGTH: 24
<212> TYPE: DNA
<213> ORGANISM: Artificial
<220> FEATURE:
<223> OTHER INFORMATION: primer

<400> SEQUENCE: 25
agctcatatg cgcccagcac ctgg                                          24

<210> SEQ ID NO 26
<211> LENGTH: 37
<212> TYPE: DNA
<213> ORGANISM: Artificial
<220> FEATURE:
<223> OTHER INFORMATION: primer

<400> SEQUENCE: 26
agctggatcc ctaattccag ctaggatcat agccctc                            37
```